(12) United States Patent
Picataggio et al.

(10) Patent No.: US 7,838,651 B2
(45) Date of Patent: Nov. 23, 2010

(54) CODON-OPTIMIZED GENES FOR THE PRODUCTION OF POLYUNSATURATED FATTY ACIDS IN OLEAGINOUS YEASTS

(75) Inventors: Stephen K. Picataggio, Gaithersburg, MD (US); Quinn Qun Zhu, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 125 days.

(21) Appl. No.: 12/018,222

(22) Filed: Jan. 23, 2008

(65) Prior Publication Data

US 2008/0154027 A1 Jun. 26, 2008

Related U.S. Application Data

(62) Division of application No. 10/840,478, filed on May 6, 2004, now Pat. No. 7,125,672.

(60) Provisional application No. 60/468,718, filed on May 7, 2003, provisional application No. 60/468,677, filed on May 7, 2003.

(51) Int. Cl.
C07H 21/04 (2006.01)
(52) U.S. Cl. ................. 536/24.1; 536/23.1
(58) Field of Classification Search ............... None
See application file for complete search history.

(56) References Cited

U.S. PATENT DOCUMENTS

| | | | |
|---|---|---|---|
| 4,666,701 A | 5/1987 | Horrobin et al. | |
| 4,758,592 A | 7/1988 | Horrobin et al. | |
| 4,826,877 A | 5/1989 | Stewart et al. | |
| 5,057,419 A | 10/1991 | Martin et al. | |
| 5,116,871 A | 5/1992 | Horrobin et al. | |
| 5,443,974 A | 8/1995 | Hitz et al. | |
| 5,968,809 A | 10/1999 | Knutzon et al. | |
| 5,972,664 A | 10/1999 | Knutzon et al. | |
| 6,075,183 A | 6/2000 | Knutzon et al. | |
| 6,136,574 A | 10/2000 | Knutzon et al. | |
| 6,207,373 B1* | 3/2001 | Sosnowski et al. | ............. 435/6 |
| 6,677,145 B2 | 1/2004 | Mukerji et al. | |
| 2003/0196217 A1 | 10/2003 | Mukerji et al. | |
| 2005/0266537 A1 | 12/2005 | Chen | |

FOREIGN PATENT DOCUMENTS

| | | |
|---|---|---|
| EP | 0005277 B1 | 1/1982 |
| WO | WO 91/13972 A1 | 9/1991 |
| WO | WO 93/11245 A1 | 6/1993 |
| WO | WO 94/11516 A1 | 5/1994 |
| WO | WO 00/12720 A2 | 3/2000 |
| WO | WO 02/090493 A2 | 11/2002 |
| WO | WO 03/099216 A2 | 12/2003 |

OTHER PUBLICATIONS

Genbank accession No. L35923.*
Garrett-Engele et al. Calcineurin, the Ca2+/calmodulin-dependent protein phosphatase, is essential in yeast mutants with cell integrity defects and in mutants that lack a functional vacuolar H(+)-ATPase. Mol Cell Biol. Aug. 1995;15(8):4103-14.*
Gaillardin et al. Integrative transformation of the yeast *Yarrowia lipolytica*. Current Genetics 10(1): 49-58, 1985.*
GenBank accession No. L35923, Aug. 1995.*
Dyerberg, J. et al., Fatty Acid Composition of the plasma lipids in Greenland Eskimos, Amer. J. Clin Nutr. 28: pp. 958-966, 1975.
Dyerberg, J. et al., Eicosapentaenoic Acid and Prevention of Thrombosis and Atherosclerosis?, Lancet 2(8081): pp. 117-119, Jul. 15, 1978.
Shimokawa, H., Beneficial Effects of Eicosapentaenoic Acid on Endothelial Vasodilator Functions in Animals and Humans, World Rev. Nutr. Diet, 88: pp. 100-108, 2001.
Von Schacky et al.,Fatty Acids from Eskimos to Clical Cardiology—What Took Us So Long?, World Rev. Nutr. Diet, 88: pp. 90-99, 2001.
Domergue et al., Cloning and functional characterization of Phaeodactylum tricornutuim front-end desaturases involved in eicosapentaenoic acid biosynthesis, Eur. J. Biochem. 269: 4105-4113, 2002.
Beaudoin et al., Heterologous reconstitution in yeast of the polyunsaturated fatty acid biosynthetic pathway, Proc. Natl. Acad. Sci. U.S.A. 97(12): 6421-6, 2000.
Dyer et al.,Metabolic engineering of *Saccharomyces cerevisiae* for production of novel lipid compounds, Appl. Eniv. Microbiol., 59: pp. 224-230, 2002.
Ratledge, Microbial Oils and Fats: An Assessment of their Commercial Potential, C., Prog. Ind. Microbiol. 16: 119-206, 1982.
Brenner et al., Regulatory function of Delta6 Desaturase—Key Enzyme of Polyunsaturated Fatty Acid Synthesis, Adv. Exp. Med. Biol. 83: pp. 85-101, 1976.
Horrobin et al., Fatty acid metabolism in health and sisease: the role of delta-6-desaturase Am. J. Clin. Nutr. 57, (Suppl.) 732S-737S, 1993.
Accession No. AF465281, Mortierella alpina, Feb. 4, 2002.
Accession No. AX464731, Mortierella alpina, Jul. 16, 2002.

* cited by examiner

*Primary Examiner*—Michele K Joike

(57) ABSTRACT

The present invention relates to fatty acid desaturases and elongases able to catalyze the conversion of linoleic acid (LA) to γ-linolenic acid (GLA); α-linoleic acid (ALA) to steridonic acid (STA); GLA to dihomo-γ-linoleic acid (DGLA); STA to eicosatetraenoic acid (ETA); DGLA to ETA; eicosapentaenoic acid (EPA) to docosapentaenoic acid (DPA); and arachidonic acid (ARA) to EPA. Nucleic acid sequences encoding codon-optimized desaturases and elongases, nucleic acid sequences which hybridize thereto, DNA constructs comprising the codon-optimized desaturase or elongases, and recombinant host microorganisms expressing increased levels of desaturase or elongase are described.

1 Claim, 23 Drawing Sheets

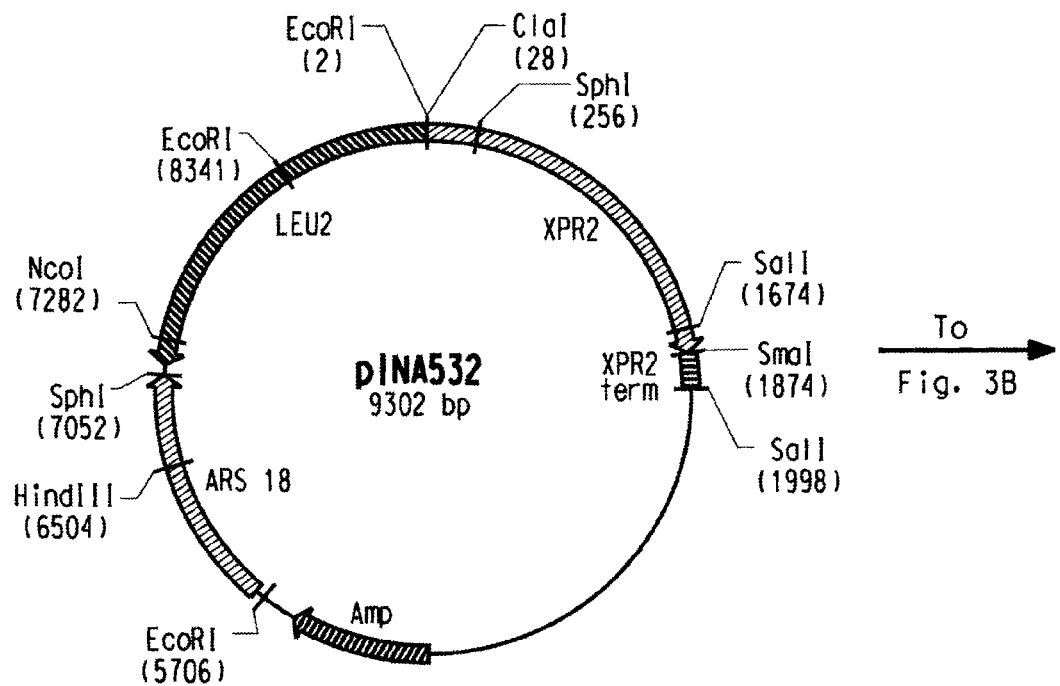
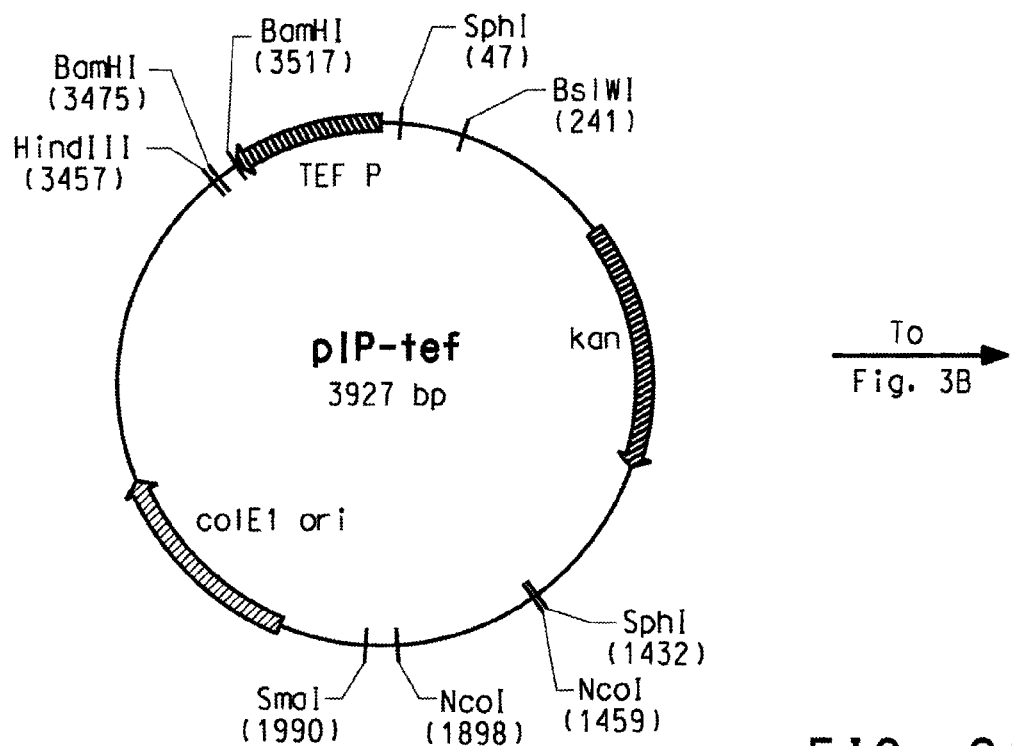
FIG. 2A

CAAAATGNCG [SEQ ID NO:122]
A CC    TC
         A

```
            CC    C  TC             C                C
         GTGAGCATGCGTTGGAGATGTTCTCGGATGTCCCAGATGAGGAGCTGACCCGCATGTGGTCGCGTTTCAT  770
          S  E  H  A  L  E  M  F  S  D  V  P  D  E  E  L  T  R  M  W  S  R  F  M

GGTCCTGAACCAGACCTGGTTTTACTTCCCCATTCTCTCGTTTGCCCGTTCTCTTGTGCCTCCAGTCC  840
          V  L  N  Q  T  W  F  Y  F  P  I  L  S  F  A  R  L  S  W  C  L  Q  S
                C                                CA  A
         ATTCTCTTTGTGCTGCCTAACGGTCAGGCCCACAAGCCCTGGGCGCTGTGCCCATCTCGTTGGTCG  910
          I  L  F  V  L  P  N  G  Q  A  H  K  P  S  G  A  R  V  P  I  S  L  V
            C       CC                  T                                  T
         AGCAGCTGTCGCTTGCACTGGAACTGGTACCTCGCCACCATGTTCCTGTTCATCAAGGATCCCGT  980
          E  Q  L  S  L  A  M  H  W  T  W  Y  L  A  T  M  F  L  F  I  K  D  P  V
            C          CC                 T        C   C                     C
         CAACATGCTGGTGTACTTTTTGGTGTCGCAGGCGGTGTGCGGAAACTTGTTGGCCATCGTGTTCTCGCTC  1050
          N  M  L  V  Y  F  L  V  S  Q  A  V  C  G  N  L  L  A  I  V  F  S  L
                                               C           T       TC
         AACCACAACGGTATGCCTGTGATCTCGAAGGAGGCGGTCGATATGGACTTCTTCACGAAGCAGATCA  1120
          N  H  N  G  M  P  V  I  S  K  E  E  A  V  D  M  D  F  F  T  K  Q  I
                      T        TCT   G      C                   CC
         TCACGGGTCGTGATGTGCACCCGGGTCTATTTGCCAACTGGTTCACGGGTGGATTGAACTATCAGATCGA  1190
          I  T  G  R  D  V  H  P  G  L  F  A  N  W  F  T  G  G  L  N  Y  Q  I  E
              T   C                                    C
         GCAACACTGTCCCTTCGATGCCTCGCATGCCTCGCACAAACTTTCAAAGATCCAGCCTGTGAGACCCTGTGC  1260
          H  H  L  F  P  S  M  P  R  H  N  F  S  K  I  Q  P  A  V  E  T  L  C
            G                                   T                 C   C      A
         AAAAAGTACAATGTCCGATACCACCACCGGTACTGATGATCGAGGAACTGCAGAGTCTTTAGCCGTCTGA  1330
          K  K  Y  N  V  R  Y  H  T  T  G  M  I  E  G  T  A  E  V  F  S  R  L
                              C                T
         ACGAGGTCTCCAAGGCTACCTCCAAGATGGGTAAGGCGCAGTAA  1374
          N  E  V  S  K  A  T  S  K  M  G  K  A  Q
```

```
                                                                            T  T
CTCACATACTCGCTCGGCTTTGCCGTCATGGGCCTCTACTACTATGCCGCTCTTTGTCTTTGCTTCGT        700
 L  T  Y  S  L  G  F  A  V  M  G  L  Y  Y  Y  A  P  L  F  V  F  A  S

T                   T  T  C             T
TCCTCGTCATTACGACCTTCTTGCACCACAACGACGAAGCCGACGGGTACGGCGACTCGGAGTGGAC         770
 F  L  V  I  T  T  F  L  H  H  N  D  E  A  T  P  W  Y  G  D  S  E  W  T

GAGCTC           A     T                                  TCT
GTACGTCAAGGGCAACCTCTCGAGCGTCGACCGCTCGTACGGCGTTCGTGGACAACCTGAGCCACCAC        840
 Y  V  K  G  N  L  S  S  V  D  R  S  Y  G  A  F  V  D  N  L  S  H  H

C                    T                 C
ATTGGCACGCACCAGGTCCACCACTTGTTCCCGATCATTCCGCACTACAAGCTCAACGAAGCCACCAAGC     910
 I  G  T  H  Q  V  H  H  L  F  P  I  I  P  H  Y  K  L  N  E  A  T  K

T  T  T          A  AC  T                               T
ACTTTGCGGCCGCCTACCCGCACCTCGTGCGCAGGAACGACGAGCCCATCATCACGGCCTTCTTCAAGAC     980
 H  F  A  A  A  Y  P  H  L  V  R  R  N  D  E  P  I  I  T  A  F  F  K  T

T                    A                T   T  T         C        T  T
CGGCACCTCTTTGTCAACTACGGCGCGTGCCCGAGAGGGGCCAGATCTTCACGCTCAAAGAGTCGGCC       1050
 A  H  L  F  V  N  Y  G  A  V  P  E  T  A  Q  I  F  T  L  K  E  S  A

T  A     AGC
GCGGGCCGCCAAGGCCAAGTCGGACTAA     1077
 A  A  A  K  A  K  S  D

```
                C     T      C       G  C     C   TG C    C           C                    A  T  T   C
          ATGGAGTCGATTGCCGCCATTCCTCCCATTCAAAGATGCCGCAAGATCTGTTTATGGACCTTGCCACCGCTATCGGTGTCCGGGGCCGGCCCTATGTCGATC      100
           M  E  S  I  A  P  F  L  P  S  K  M  P  Q  D  L  F  M  D  L  A  T  A  I  G  V  R  A  A  P  Y  V  D
           C G           T  C                   T C                          T A C         T C               T CC         T
          CTCTGGAGGTCGGCCGTGGCTGGCCCAAGGCCGAGAATACACCGGCTGTCCATCACACGGCTGGTCGCGGTGGAGTCGCCTTTGGCCCG                       200
           P  L  E  A  A  L  V  A  Q  A  E  K  Y  I  P  T  I  V  H  H  T  R  G  F  L  V  A  V  E  S  P  L  A  R
          A            CC                    C           CC                              T               C    CG                      A A
          TGAGCTGCCGTTGATGAACCCGTTCCACGTGCTGCTGTATTTGGTCGTGACGGTCTTTGTGGGCATGCAGATCATGAAGAACTTTGAGCGG                   300
           E  L  P  L  M  N  P  F  H  V  L  L  I  V  L  A  Y  L  V  V  T  V  F  V  G  M  Q  I  M  K  N  F  E  R
              C    C     C          C                                     TC                        C
          TTCGAGGTCAAGACGTTTTCGCTCCTGCACAACTTTGTCTGGATCATAGCGCCTACATGTGCGGGATCCTGTACGAGGCTTATCAGGCAACT              400
           F  E  V  K  T  F  S  L  L  H  N  F  C  L  V  S  I  S  A  Y  M  C  G  G  I  L  Y  E  A  Y  Q  A  N
                                                      A    T  TC       G                           TCT                               C
          ATGGACTGTTTGAGAACGCTGATCATACCTTCAAGGGTCTTGATCTGGCTCTTCTACTTCTCCAAGATCATGGAGTTTGTCGA                              500
           Y  G  L  F  E  N  A  A  D  H  T  F  K  G  L  P  M  A  K  M  I  W  L  F  Y  F  S  K  I  M  E  F  V  D
                                                                                                      CC              C    C   C              TC      T C
          CACCATGATCATGGTCCTCAAGAAGAATAACCGCCAGAGATCTCCTTCGTGCACGTTTACCACCATCTGGTTACCGATCCATCTGGTCACCTTT                   600
           T  M  I  M  V  L  K  K  N  N  R  Q  I  S  F  L  H  V  Y  H  H  S  S  I  F  T  I  W  L  V  T  F
             T                                           CC                                       T A C             C
          GTTGCACCCAACGGTGAAGCCTACTTCTCTGCTGCTCTGAACTCGTTCATCCATGTGATCATGTACGGCTACTTCTTGTCGGCCTTGAAGC                       700
           V  A  P  N  G  E  A  Y  F  S  A  A  L  N  S  F  I  H  V  I  M  Y  G  Y  F  L  S  A  L  G  F  K
                                                                                             C
          AGGTGTCTTCATCAAGTTCTACATCACGCGCTCCCAGATGACACAGTTCTGCATGATGTCGGTTCAGTCTTCCTGGGACATGTACGCCATGAAGGTCCTT           800
           Q  V  S  F  I  K  F  Y  I  T  R  S  Q  M  T  Q  F  C  M  M  S  V  Q  S  S  W  D  M  Y  A  M  K  V  L
                         A  T                                                                  C A   CC
          TGGCCGCCCGGATACCCCTTCTTCATCACGGCTCTGCTTGGTTCTACATGTGGACCATGCTCGGTTCTCTTACAACTTTTACAGAAAGAACGCCAAG           900
           Q  R  P  G  Y  P  F  F  I  T  A  L  L  W  F  Y  M  W  T  M  L  G  F  Y  N  F  Y  R  K  N  A  K
          C C                                                                                                                                                 T
          TTGGCCAAGCAGGCCAAGGCCGACGCTGCCAAGGAGAAGGCAAGGAAGTTGCAGTAA                            (SEQ ID NO:5)
           L  A  K  Q  A  K  A  D  A  A  K  E  K  A  R  K  L  Q                                (SEQ ID NO:6)
```

FIG. 11

957 bp of elongase gene

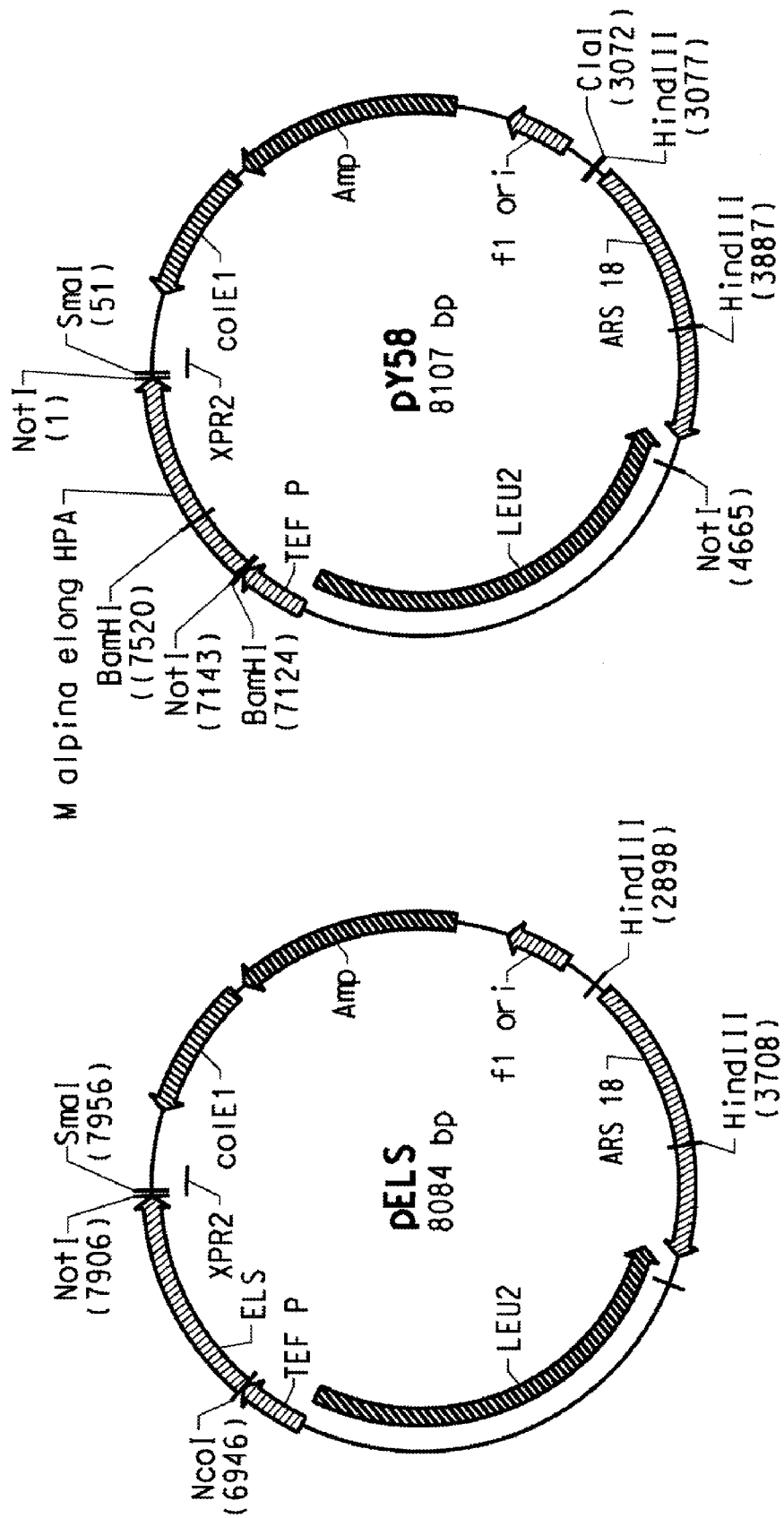

… # CODON-OPTIMIZED GENES FOR THE PRODUCTION OF POLYUNSATURATED FATTY ACIDS IN OLEAGINOUS YEASTS

This application claims the benefit of U.S. Provisional Application No. 60/468,677, filed May 7, 2003 and U.S. Provisional Application No. 60/468,718, filed May 7, 2003.

FIELD OF THE INVENTION

This invention is in the field of biotechnology. More specifically, this invention pertains to the synthesis of nucleic acid fragments encoding enzymes useful for the production of long chain polyunsaturated fatty acids (PUFAs) in oleaginous yeasts.

BACKGROUND OF THE INVENTION

It has long been recognized that certain polyunsaturated fatty acids, or PUFAs, are important biological components of healthy cells. For example, such PUFAs are recognized as:
  "Essential" fatty acids that can not be synthesized de novo in mammals and instead must be obtained either in the diet or derived by further desaturation and elongation of linoleic acid (LA) or α-linolenic acid (ALA);
  Constituents of plasma membranes of cells, where they may be found in such forms as phospholipids or triglycerides;
  Necessary for proper development, particularly in the developing infant brain and for tissue formation and repair; and,
  Precursors to several biologically active eicosanoids of importance in mammals, including prostacyclins, eicosanoids, leukotrienes and prostaglandins.

In the 1970's, observations of Greenland Eskimos linked a low incidence of heart disease and a high intake of long-chain ω-3 PUFAs (Dyerberg, J. et al., *Amer. J. Clin Nutr.* 28:958-966 (1975); Dyerberg, J. et al., *Lancet* 2(8081):117-119 (Jul. 15, 1978)). More recent studies have confirmed the cardiovascular protective effects of ω-3 PUFAs (Shimokawa, H., *World Rev Nutr Diet,* 88:100-108 (2001); von Schacky, C., and Dyerberg, J., *World Rev Nutr Diet,* 88:90-99 (2001)). Further, it has been discovered that several disorders respond to treatment with ω-3 fatty acids, such as the rate of restenosis after angioplasty, symptoms of inflammation and rheumatoid arthritis, asthma, psoriasis and eczema. γ-linolenic acid (GLA, an ω-6 PUFA) has been shown to reduce increases in blood pressure associated with stress and to improve performance on arithmetic tests. GLA and dihomo-γ-linolenic acid (DGLA, another ω-6 PUFA) have been shown to inhibit platelet aggregation, cause vasodilation, lower cholesterol levels and inhibit proliferation of vessel wall smooth muscle and fibrous tissue (Brenner et al., *Adv. Exp. Med. Biol.* 83: 85-101 (1976)). Administration of GLA or DGLA, alone or in combination with eicosapentaenoic acid (EPA, an ω-3 PUFA), has been shown to reduce or prevent gastrointestinal bleeding and other side effects caused by non-steroidal anti-inflammatory drugs (U.S. Pat. No. 4,666,701). Further, GLA and DGLA have been shown to prevent or treat endometriosis and premenstrual syndrome (U.S. Pat. No. 4,758,592) and to treat myalgic encephalomyelitis and chronic fatigue after viral infections (U.S. Pat. No. 5,116,871). Other evidence indicates that PUFAs may be involved in the regulation of calcium metabolism, suggesting that they may be useful in the treatment or prevention of osteoporosis and kidney or urinary tract stones. Finally, PUFAs can be used in the treatment of cancer and diabetes (U.S. Pat. No. 4,826,877; Horrobin et al., *Am. J. Clin. Nutr.* 57 (Suppl.): 732S-737S (1993)).

PUFAs are generally divided into two major classes (consisting of the ω-6 and the ω-3 fatty acids) that are derived by desaturation and elongation of the essential fatty acids, LA and ALA, respectively (FIG. 1). Despite a variety of commercial sources of PUFAs from natural sources (e.g., seeds of evening primrose, borage and black currants; filamentous fungi (*Mortierella*), *Porphyridium* (red alga), fish oils and marine plankton (*Cyclotella, Nitzschia, Crypthecodinium*)), there are several disadvantages associated with these methods of production. First, natural sources such as fish and plants tend to have highly heterogeneous oil compositions. The oils obtained from these sources therefore can require extensive purification to separate or enrich one or more of the desired PUFAs. Natural sources are also subject to uncontrollable fluctuations in availability (e.g., due to weather, disease, or over-fishing in the case of fish stocks); and, crops that produce PUFAs often are not competitive economically with hybrid crops developed for food production. Large-scale fermentation of some organisms that naturally produce PUFAs (e.g., *Porphyridium, Mortierella*) can also be expensive and/or difficult to cultivate on a commercial scale.

As a result of the limitations described above, extensive work has been conducted toward: 1.) the development of recombinant sources of PUFAs that are easy to produce commercially; and 2.) modification of fatty acid biosynthetic pathways, to enable production of desired PUFAs. For example, advances in the isolation, cloning and manipulation of fatty acid desaturase and elongase genes from various organisms have been made over the last several years. Knowledge of these gene sequences offers the prospect of producing a desired fatty acid and/or fatty acid composition in novel host organisms that do not naturally produce PUFAs. The literature reports a number of examples in *Saccharomyces cerevisiae*, such as:

1. Domergue, F. et al. (*Eur. J. Biochem.* 269:4105-4113 (2002)), wherein two desaturases from the marine diatom *Phaeodactylum tricornutum* were cloned into *S. cerevisiae*, leading to the production of EPA;
2. Beaudoin F., et al. (*Proc. Natl. Acad. Sci. U.S.A.* 97(12): 6421-6 (2000)), wherein the ω-3 and ω-6 PUFA biosynthetic pathways were reconstituted in *S. cerevisiae*, using genes from *Caenorhabditis elegans*;
3. Dyer, J. M. et al. (*Appl. Eniv. Microbiol.,* 59:224-230 (2002)), wherein plant fatty acid desaturases (FAD2 and FAD3) were expressed in *S. cerevisiae*, leading to the production of ALA; and,
4. U.S. Pat. No. 6,136,574 (Knutzon et al., Abbott Laboratories), wherein one desaturase from *Brassica napus* and two desaturases from the fungus *Mortierella alpina* were cloned into *S. cerevisiae*, leading to the production of LA, GLA, ALA and STA.

There remains a need, however, for an appropriate microbial system in which these types of genes can be expressed to provide for economical production of commercial quantities of one or more PUFAs. Additionally, a need exists for oils enriched in specific PUFAs, notably EPA and DHA.

One class or microorganisms that has not been previously examined as a production platform for PUFAs are the oleaginous yeasts. These organisms can accumulate oil up to 80% of their dry cell weight. The technology for growing oleaginous yeast with high oil content is well developed (for example, see EP 0 005 277 B1; Ratledge, C., *Prog. Ind. Microbiol.* 16:119-206 (1982)), and may offer a cost advantage compared to commercial micro-algae fermentation for production of ω-3 or ω-6 PUFAs. Whole yeast cells may also represent a convenient way of encapsulating ω-3 or ω-6 PUFA-enriched oils for use in functional foods and animal feed supplements.

Despite the advantages noted above, oleaginous yeast are naturally deficient in ω-6 and ω-3 PUFAs, since naturally produced PUFAs in these organisms are limited to 18:2 fatty acids (and less commonly, 18:3 fatty acids). Thus, the problem to be solved is to develop an oleaginous yeast that accumulates oils enriched in ω-3 and/or ω-6 fatty acids. Toward this end, it is necessary to introduce desaturases and elongases that allow for the synthesis and accumulation of ω-3 and/or ω-6 fatty acids in oleaginous yeasts. Despite availability of a variety of desaturase and elongase genes from numerous sources, these genes are not expressed with optimal efficiency in alternate hosts such as oleaginous yeast, since the codons in the genes do not reflect the typical codon usage of the alternate host organism. Thus, one must overcome problems associated with codon usage to optimize expression of PUFA genes in oleaginous yeast, to enable high-level production and accumulation of ω-3 and/or ω-6 fatty acids in these particular host organisms.

Applicants have solved the stated problem by developing means to codon-optimize desaturase and elongase genes suitable for expression in the oleaginous host, *Yarrowia lipolytica*. Exemplary genes optimized herein are those genes encoding a Δ6 desaturase, Δ17 desaturase and high affinity PUFA elongase, wherein codon-optimization improved the percent substrate conversion of LA to GLA (Δ6 desaturase) by approximately 40%, ARA to EPA by about 2-fold (Δ17 desaturase), and GLA to DGLA (elongase) by about 57% in *Y. lipolytica*.

SUMMARY OF THE INVENTION

The present invention relates to the optimization of various genes in the ω-3/ω-6 fatty acid biosynthetic pathway for optimal expression in *Yarrowia* sp. Accordingly, the invention provides an isolated nucleic acid molecule selected from the group consisting of:
  a) an isolated nucleic acid molecule as set forth in SEQ ID NO:25 which encodes a Δ6 desaturase enzyme; or
  b) an isolated nucleic acid molecule that is completely complementary to (a).

Similarly the invention provides an isolated nucleic acid molecule which encodes a Δ6 desaturase enzyme as set forth in SEQ ID NO:2 wherein at least 144 codons are codon-optimized for expression in *Yarrowia* sp.

In another embodiment the invention provides an isolated nucleic acid molecule selected from the group consisting of:
  a) an isolated nucleic acid molecule encoding a Δ17 desaturase enzyme as set forth in SEQ ID NO:62; or
  b) an isolated nucleic acid molecule that is completely complementary to (a).

In another embodiment the invention provides an isolated nucleic acid molecule which encodes a Δ17 desaturase enzyme as set forth in SEQ ID NO:4 wherein at least 117 codons are codon-optimized for expression in *Yarrowia* sp.

Similarly the invention provides an isolated nucleic acid molecule, selected from the group consisting of:
  a) an isolated nucleic acid molecule encoding an elongase enzyme as set forth in SEQ ID NO:91; or
  b) an isolated nucleic acid molecule that is completely complementary to (a).

Alternatively the invention provides an isolated nucleic acid molecule which encodes an elongase enzyme as set forth in SEQ ID NO:6 wherein at least 85 codons are codon-optimized for expression in *Yarrowia* sp.

Additionally the invention provides genetic chimera of the genes of the present invention and host cells transformed with the same.

In specific embodiments the invention provides for the production of specific ω-3 and ω-6 fatty acids such γ-linolenic acid (GLA), dihomo-γ-linoleic acid (DGLA), stearidonic acid (STA), eicosatetraenoic acid (ETA), eicosapentaenoic acid (EPA) and docosapentaenoic acid (DPA) by single step enzymatic reactions from the appropriate precursors using the codon-optimized genes of the invention in *Yarrowia* sp.

In another embodiment the invention provides a method of optimizing a gene for expression in an oleaginous yeast comprising the steps of:
  a) obtaining the sequences of nucleotide coding regions and corresponding polypeptides for the oleaginous yeast species to form a database of codons;
  b) analyzing the database of codons to determine which codons preferentially encode each amino acid;
  c) obtaining the sequence of a gene to be expressed in an oleaginous yeast species;
  d) replacing non-preferred codons in the sequence of step (c) with those preferred codons of step (b) wherein the gene is codon-optimized for expression in an oleaginous yeast species.

In an alternate embodiment the invention provides an isolated nucleic acid molecule comprising a *Yarrowia* translation initiation site as set forth in SEQ ID NO:122. Additionally provided are methods for optimizing the expression of a gene in a *Yarrowia* host comprising:
  a) providing a foreign gene to be expressed in *Yarrowia*;
  b) operably linking the gene of step (a) with a *Yarrowia* translation initiation site as set forth in SEQ ID NO:122 wherein the foreign gene is optimized for expression in *Yarrowia*.

BRIEF DESCRIPTION OF THE DRAWINGS AND SEQUENCE DESCRIPTIONS

FIG. 4 illustrates the favored consensus sequences around the translation initiation codon 'ATG' in *Y. lipolytica*.

FIG. 5 shows a comparison of the DNA sequence of the *Mortierella alpina* Δ6 desaturase gene and the synthetic gene codon-optimized for expression in *Y. lipolytica*.

FIG. 8 show a comparison of the DNA sequence of the *Saprolegnia diclina* Δ17 desaturase gene and the synthetic gene codon-optimized for expression in *Y. lipolytica*.

FIG. 11 shows a comparison of the DNA sequence of the *Mortierella alpina* elongase gene and the synthetic gene codon-optimized for expression in *Y. lipolytica*.

FIG. 13 shows plasmids for expression of the codon-optimized and wildtype elongase genes in *Y. lipolytica*.

Figure 14A:
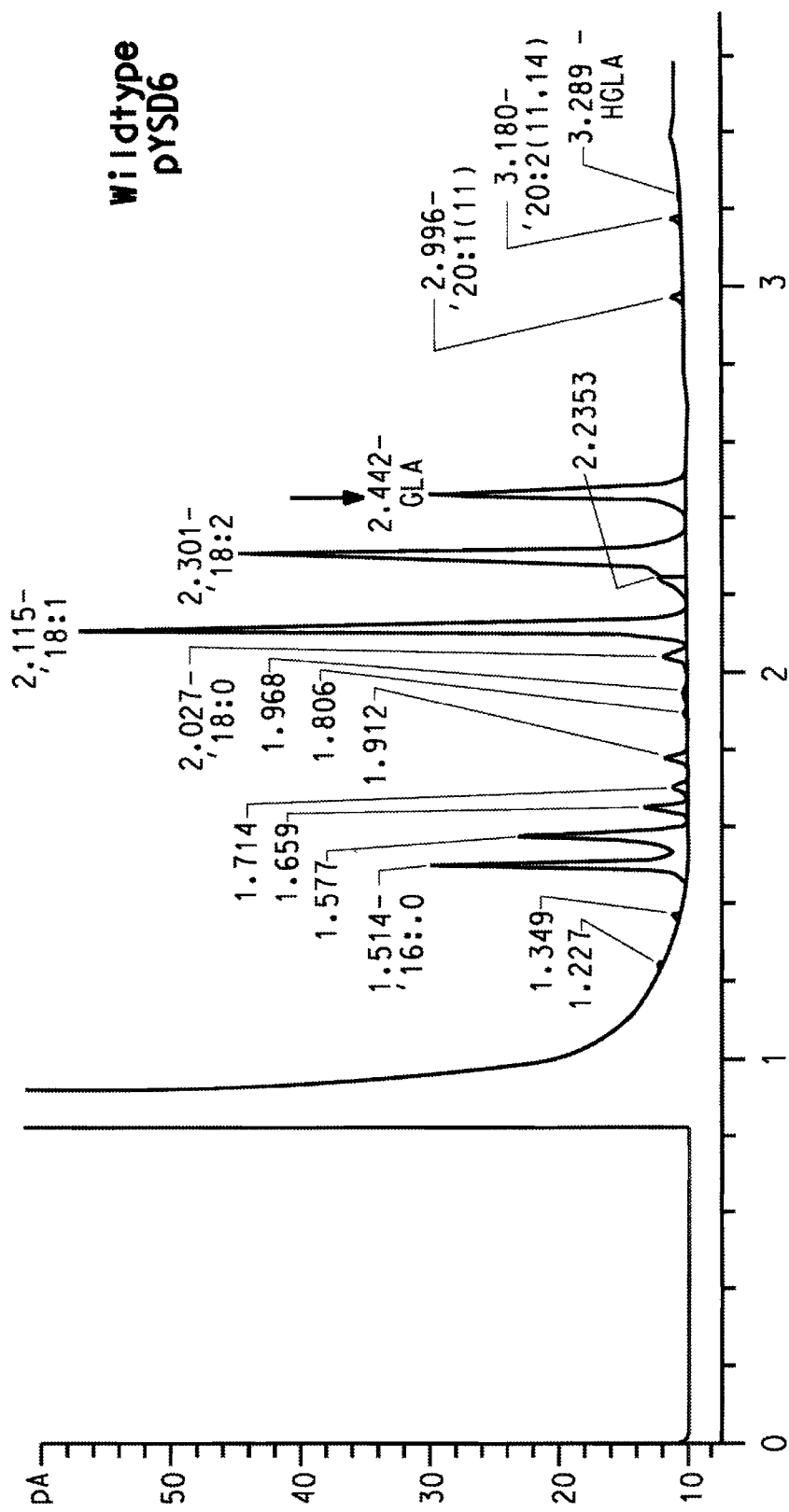
Figure 14B:
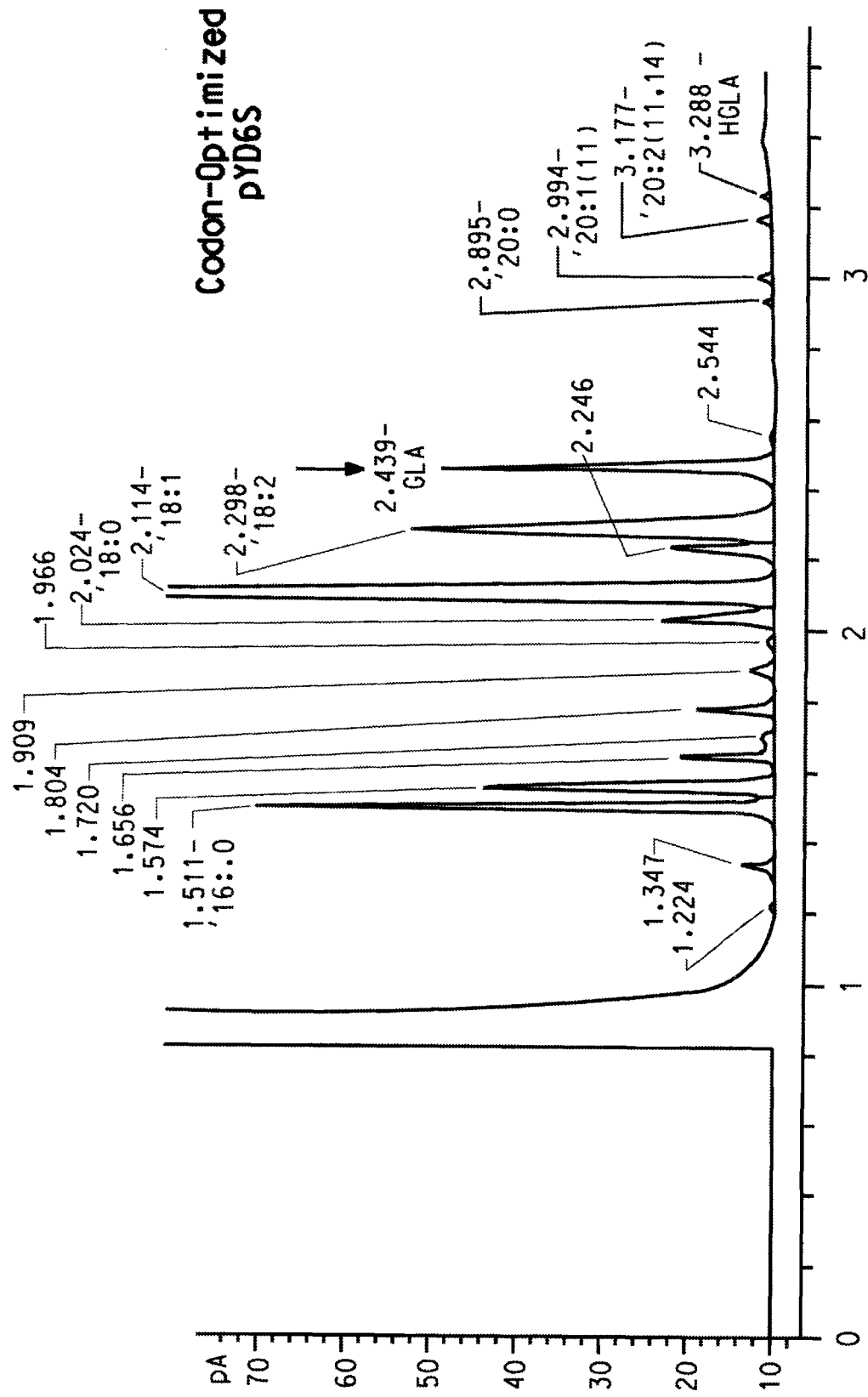

FIG. 14A shows the results of gas chromatographic analyses of fatty acids produced in *Y. lipolytica* transformed with the codon-optimized and wildtype Δ6 desaturase genes showing ~30% substrate LA to GLA; and FIG. 14B shows the results of gas chromatographic analyses of fatty acids produced in *Y. lipolytica* transformed with the codon-optimized and wildtype Δ6 desaturase genes showing ~42% LA to GLA.

Figure 15A:
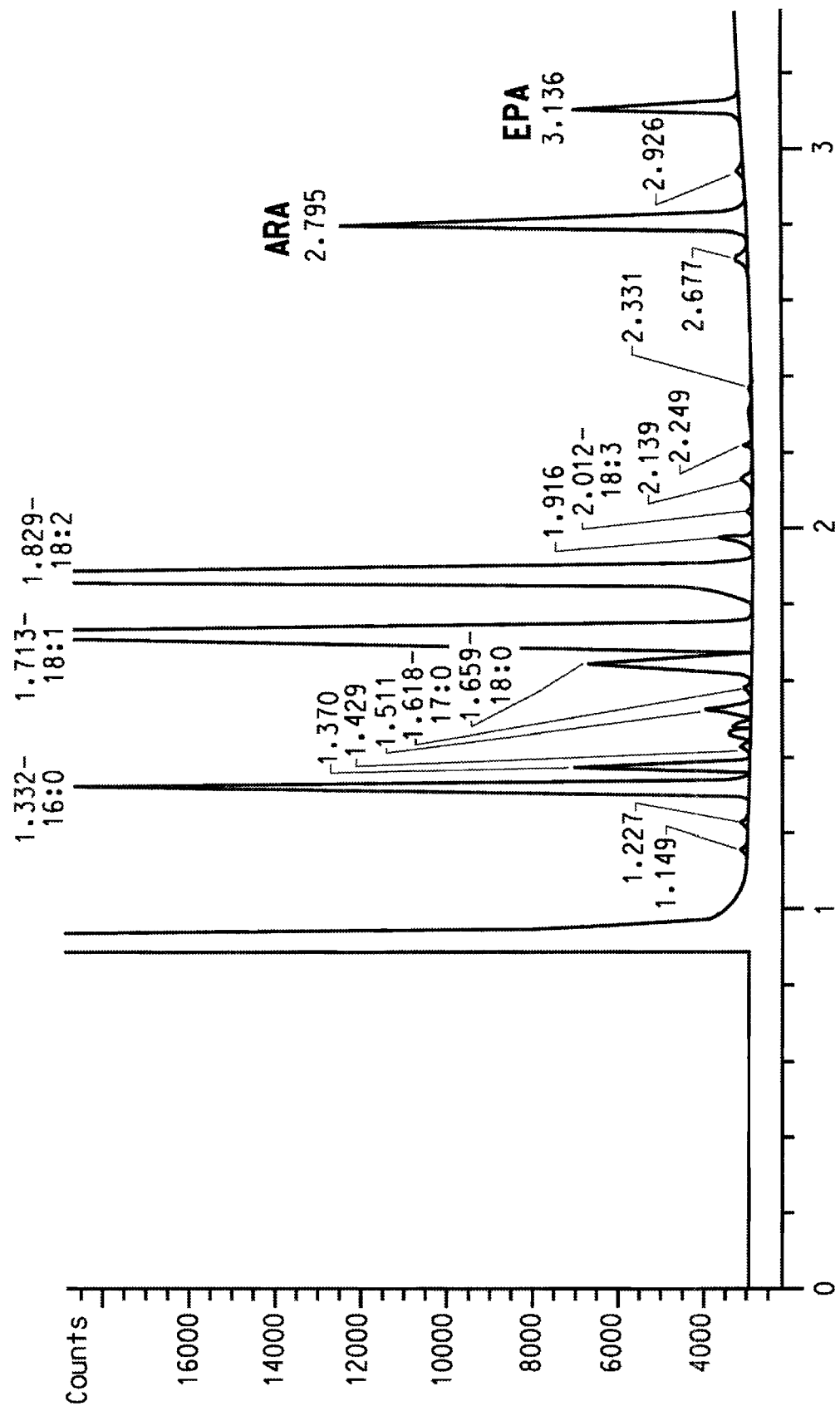
Figure 15B:
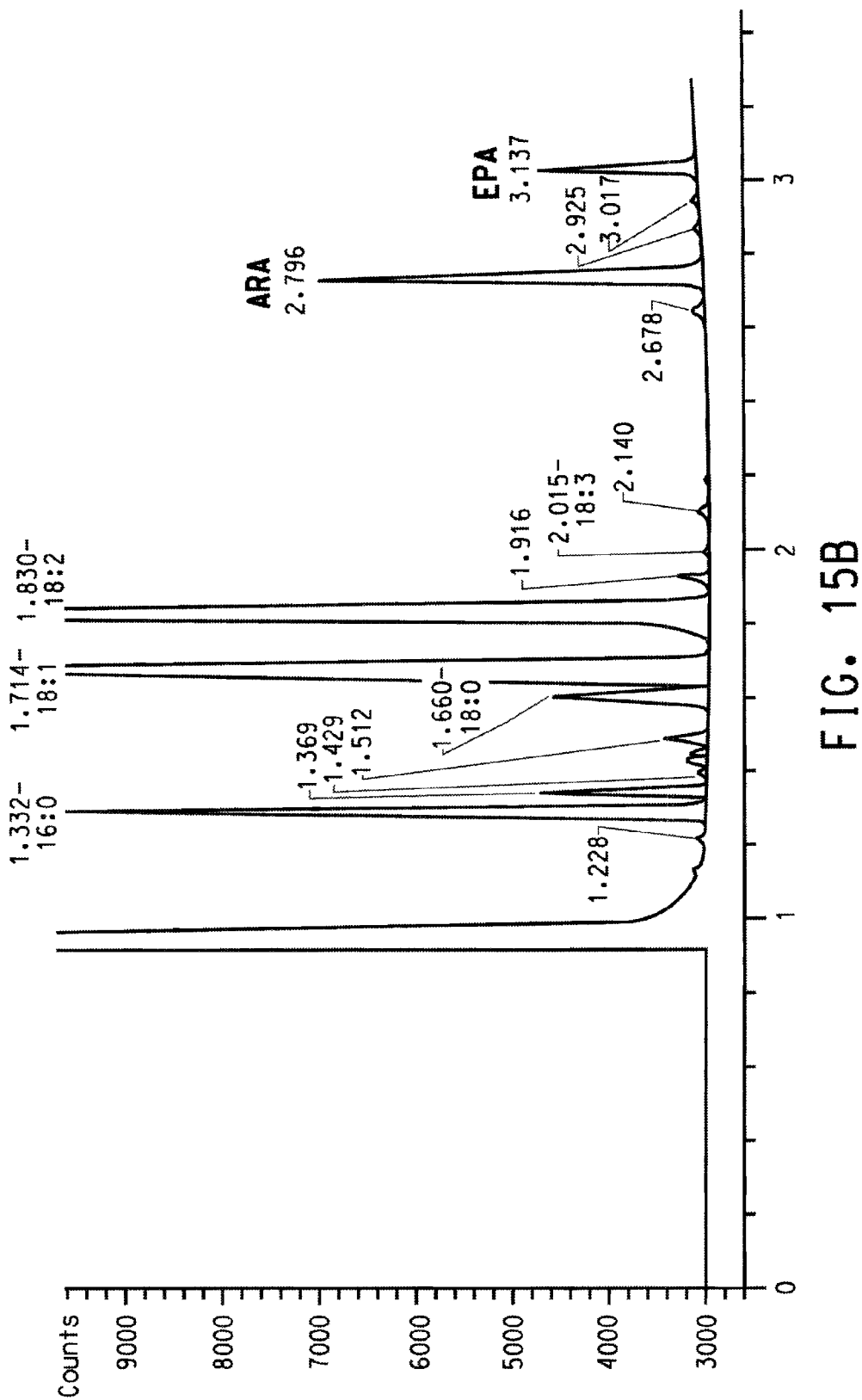

FIG. 15 shows the results of gas chromatographic analyses of fatty acids produced in *Y. lipolytica* transformed with the codon-optimized and wildtype Δ17 desaturase genes showing about 23% of intracellular ARA to EPA; and FIG. 15B shows the results of gas chromatographic analyses of fatty acids produced in *Y. lipolytica* transformed with the codon-optimized and wildtype Δ17 desaturase genes showing about 45% of intracellular ARA to EPA.

Figure 16A:
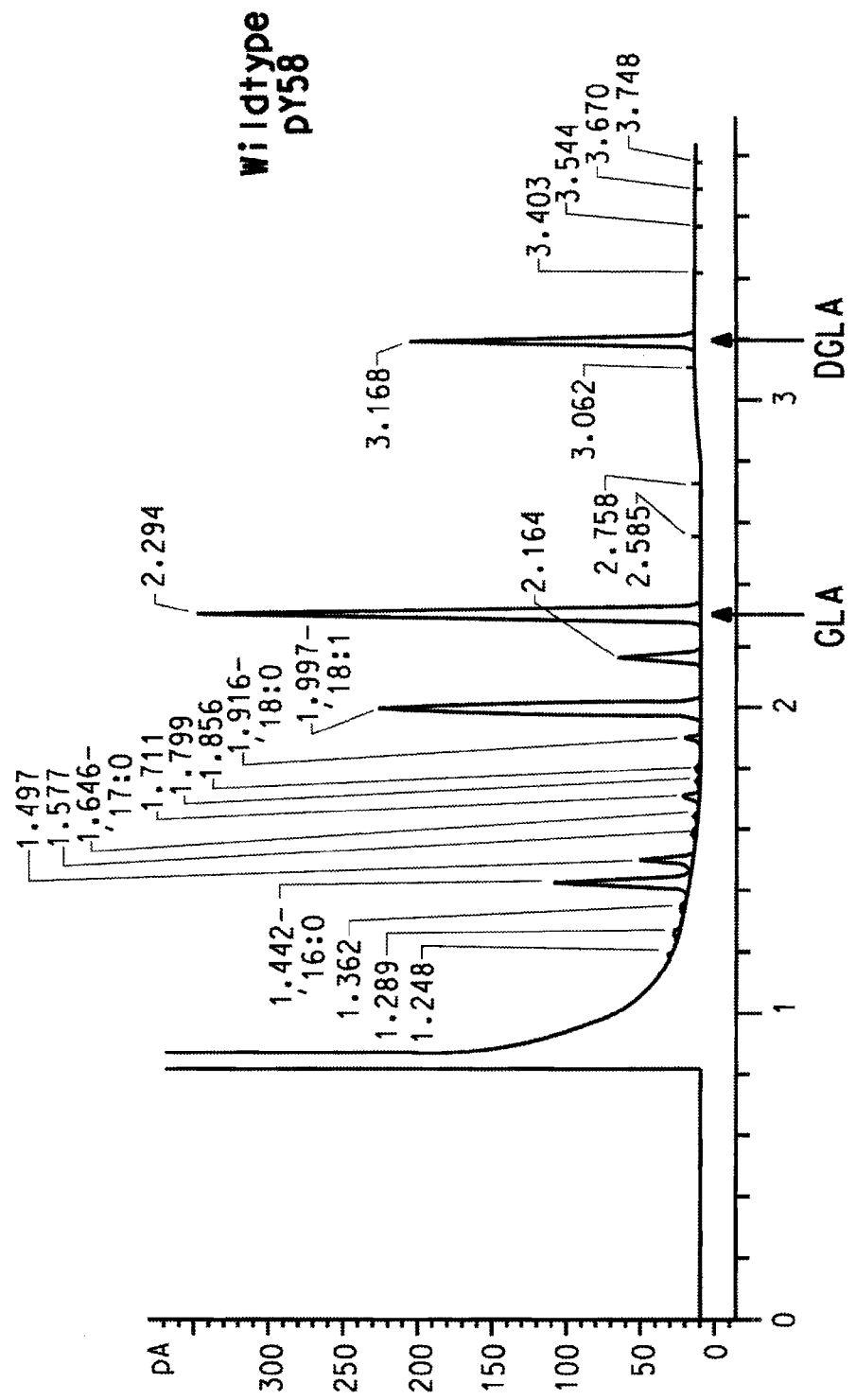
Figure 16B:
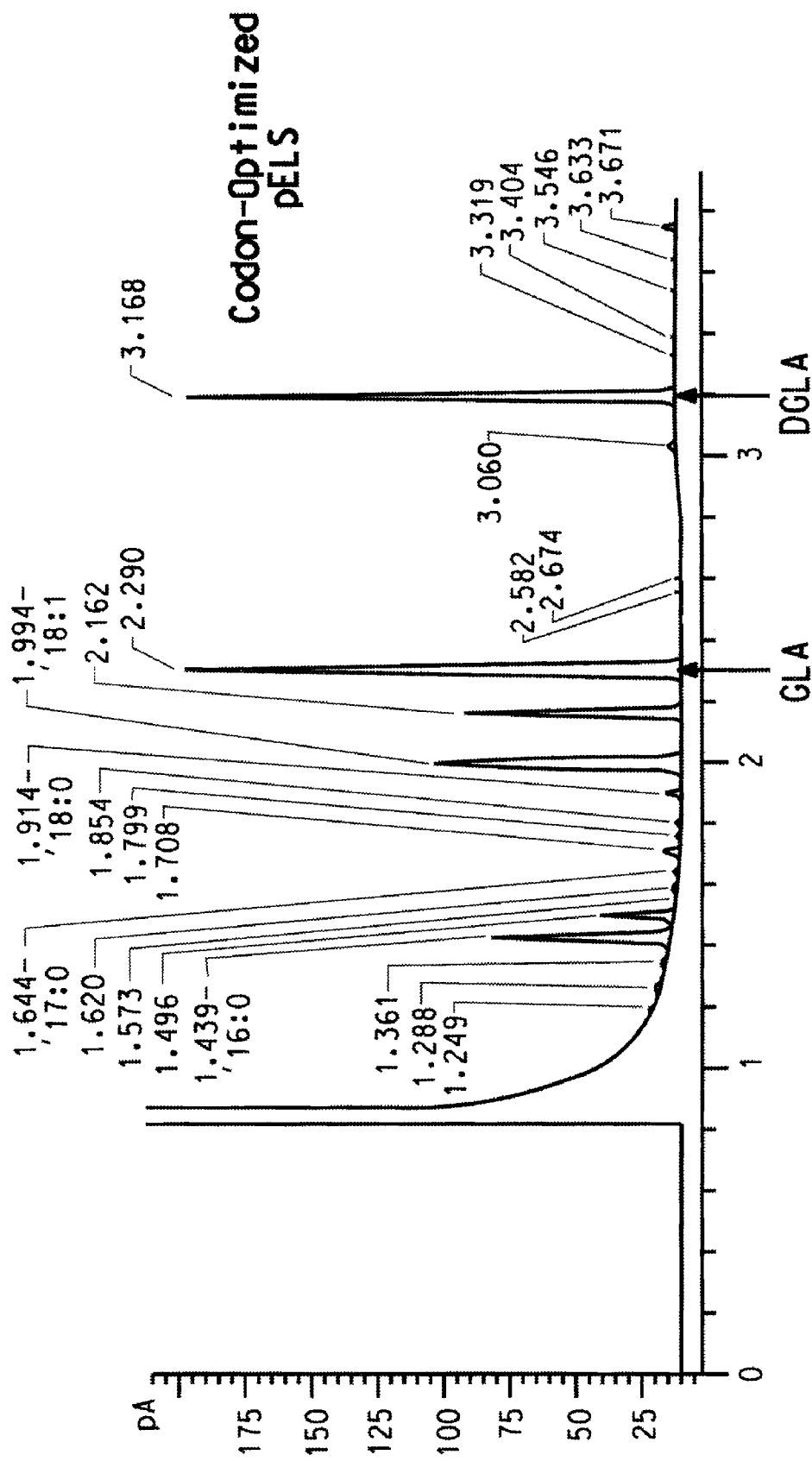

FIG. 16 shows the results of gas chromatographic analyses of fatty acids produced in *Y. lipolytica* transformed with the codon-optimized and wildtype elongase genes showing ~30% substrate GLA to DGLA; and FIG. 16B shows the results of gas chromatographic analyses of fatty acids produced in *Y. lipolytica* transformed with the codon-optimized and wildtype elongase genes showing ~47% GLA to DGLA.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 shows the DNA sequence of the *Mortierella alpina* Δ6 desaturase gene, while SEQ ID NO:2 shows the amino acid sequence of the *M. alpina* Δ6 desaturase.

SEQ ID NO:3 shows the DNA sequence of the *Saprolegnia diclina* Δ17 desaturase gene, while SEQ ID NO:4 shows the corresponding amino acid sequence of the *S. diclina* Δ17 desaturase.

SEQ ID NO:5 shows the DNA sequence of the *Mortierella alpina* high affinity elongase gene, while SEQ ID NO:6 shows the amino acid sequence of the *M. alpina* high affinity elongase.

SEQ ID NOs:7 and 8 correspond to primers TEF5' and TEF3', respectively, used to isolate the TEF promoter.

SEQ ID NOs:9 and 10 correspond to primers XPR5' and XPR3', respectively, used to isolate the XPR2 transcriptional terminator.

SEQ ID NOs:11-24 correspond to primers YL1, YL2, YL3, YL4, YL23, YL24, YL5, YL6, YL9, YL10, YL7, YL8, YL61 and YL62, respectively, used for plasmid construction.

SEQ ID NO:25 shows the DNA sequence of the synthetic Δ6 desaturase gene codon-optimized for expression in *Yarrowia lipolytica*.

SEQ ID NOs:26-53 correspond to the 14 pairs of oligonucleotides which together comprise the entire codon-optimized coding region of the *M. alpina* Δ6 desaturase gene (e.g., D6-1A, D6-1B, D6-2A, D6-2B, D6-3A, D6-3B, D6-4A, D6-4B, D6-5A, D6-5B, D6-6A, D6-6B, D6-7A, D6-7B, D6-8A, D6-8B, D6-9A, D6-9B, D6-10A, D6-10B, D6-11A, D6-11B, D6-12A, D6-12B, D6-13A, D6-13B, D6-14A and D6-14B, respectively).

SEQ ID NOs:54-61 correspond to primers D6-1, D6-4R, D6-5, D6-7R, D6-8, D6-10R, D6-11 and D6-14R, respectively, used for PCR amplification during synthesis of the codon-optimized Δ6 desaturase gene.

SEQ ID NO:62 shows the DNA sequence of the synthetic Δ17 desaturase gene codon-optimized for expression in *Yarrowia lipolytica*.

SEQ ID NOs:63-84 correspond to the 11 pairs of oligonucleotides which together comprise the entire codon-optimized coding region of the *S. diclina* Δ17 desaturase gene (e.g., D17-1A, D17-1B, D17-2A, D17-2B, D17-3A, D17-3B, D17-4A, D17-4B, D17-5A, D17-5B, D17-6A, D17-6B, D17-7A, D17-7B, D17-8A, D17-8B, D17-9A, D17-9B, D17-10A, D17-10B, D17-11A and D17-11B, respectively).

SEQ ID NOs:85-90 correspond to primers D17-1, D17-4R, D17-5, D17-8D, D17-8U and D17-11, respectively, used for PCR amplification during synthesis of the codon-optimized Δ17 desaturase gene.

SEQ ID NO:91 shows the DNA sequence of the synthetic high affinity elongase gene codon-optimized for expression in *Yarrowia lipolytica*.

SEQ ID NOs:92-111 correspond to the 10 pairs of oligonucleotides which together comprise the entire codon-optimized coding region of the *M. alpina* high affinity elongase gene (e.g., EL-1A, EL-1B, EL-2A, EL-2B, EL-3A, EL-3B, EL-4A, EL-4B, EL-5A, EL-5B, EL-6A, EL-6B, EL-7A, EL-7B, EL-8A, EL-8B, EL-9A, EL-9B, EL-10A and EL-10B, respectively).

SEQ ID NOs:112-115 correspond to primers EL-1, EL-5R, EL-6 and EL-10R, respectively, used for PCR amplification during synthesis of the codon-optimized elongase gene.

SEQ ID NOs:116 and 117 correspond to primers EL-M1 and EL-M2, used for site-directed mutagenesis to generate pELS.

SEQ ID NOs:118 and 119 correspond to primers YL21A and YL22, used for amplifying the wild type Δ17 desaturase gene of *S. diclina* from plasmid pRSP19.

SEQ ID NOs:120 and 121 correspond to primers YL53 and YL54, used for site-directed mutagenesis to generate pYSD17M.

SEQ ID NO:122 corresponds to the codon-optimized translation initiation site for genes optimally expressed in *Yarrowia* sp.

DETAILED DESCRIPTION OF THE INVENTION

In accordance with the subject invention, Applicants have determined the codon usage of structural genes in the oleaginous yeast, *Yarrowia lipolytica*. Codon-optimized genes encoding a Δ6 desaturase (SEQ ID NO:25), a Δ17 desaturase (SEQ ID NO:62) and a high affinity elongase (SEQ ID NO:91) are presented, as well as DNA cassettes for expression of said genes in host cells of *Y. lipolytica*. Additionally, methods and compositions are provided which permit modification of the long chain polyunsaturated fatty acid (PUFA) content of oleaginous yeasts, such as *Y. lipolytica*.

The subject invention finds many applications. PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolic progeny. For example, treatment with arachidonic acid (ARA) can result not only in increased levels of ARA, but also downstream products of ARA such as prostaglandins. Complex regulatory mechanisms can make it desirable to combine various PUFAs, or add different conjugates of PUFAs, in order to prevent, control or overcome such mechanisms to achieve the desired levels of specific PUFAs in an individual.

DEFINITIONS

In this disclosure, a number of terms and abbreviations are used. The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

The term "fatty acids" refers to long chain aliphatic acids (alkanoic acids) of varying chain length, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" are cis-isomers that have "double bonds" along their carbon backbones. "Monounsaturated fatty acids" have only one "double bond" along the carbon backbone (e.g., usually between the $9^{th}$ and $10^{th}$ carbon atom as for palmitoleic acid (16:1) and oleic acid (18:1)), while "polyunsaturated fatty acids" (or "PUFAs") have at least two double bonds along the carbon backbone (e.g., between the $9^{th}$ and $10^{th}$ and $12^{th}$ and $13^{th}$ carbon atoms for linoleic acid (18:2); and between the $9^{th}$ and $10^{th}$, $12^{th}$ and $13^{th}$, and $15^{th}$ and $16^{th}$ for α-linolenic acid (18:3)).

"PUFAs" can be classified into two major families (depending on the position (n) of the first double bond nearest the methyl end of the fatty acid carbon chain). Thus, the "omega-6 fatty acids" (ω-6 or n-6) have the first unsaturated double bond six carbon atoms from the omega (methyl) end of the molecule and additionally have a total of two or more double bonds, with each subsequent unsaturation occurring 3 additional carbon atoms toward the carboxyl end of the molecule. In contrast, the "omega-3 fatty acids" (ω-3 or n-3) have the first unsaturated double bond three carbon atoms away from the omega end of the molecule and additionally have a total of three or more double bonds, with each subsequent unsaturation occurring 3 additional carbon atoms toward the carboxyl end of the molecule.

For the purposes of the present disclosure, the omega-reference system will be used to indicate the number of carbons, the number of double bonds and the position of the double bond closest to the omega carbon, counting from the omega carbon (which is numbered 1 for this purpose). This nomenclature is shown below in Table 1, in the column titled "Shorthand Notation". The remainder of the Table summarizes the common names of ω-3 and ω-6 fatty acids, the abbreviations that will be used throughout the specification, and each compounds' chemical name.

TABLE 1

Nomenclature Of Polyunsaturated Fatty Acids

| Common Name | Abbreviation | Chemical Name | Shorthand Notation |
| --- | --- | --- | --- |
| Linoleic | LA | cis-9,12-octadecadienoic | 18:2 ω-6 |
| γ-Linoleic | GLA | cis-6,9,12-octadecatrienoic | 18:3 ω-6 |
| Dihomo-γ-Linoleic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatetraenoic | ETA | cis-8,11,14,17-eicosatetraenoic | 20:4 ω-3 |
| Eicosapentaenoic | EPA | cis-5,8,11,14,17-eicosapentaenoic | 20:5 ω-3 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

The term "essential fatty acid" refers to a particular PUFA that an individual must ingest in order to survive, being unable to synthesize the particular essential fatty acid de novo. For example, mammals can not synthesize the essential fatty acid linoleic acid (18:2, ω-6). Other essential fatty acids include GLA (ω-6), DGLA (ω-6), ARA (ω-6), EPA (ω-3) and DHA (ω-3).

The term "fat" refers to a lipid substance that is solid at 25° C. and usually saturated.

The term "oil" refers to a lipid substance that is liquid at 25° C. and usually polyunsaturated. PUFAs are found in the oils of some algae, oleaginous yeasts and filamentous fungi. "Microbial oils" or "single cell oils" are those oils naturally produced by microorganisms during their lifespan. Such oils can contain long chain PUFAs.

The term "PUFA biosynthetic pathway enzyme" refers to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase and/or an elongase.

Figure 1:
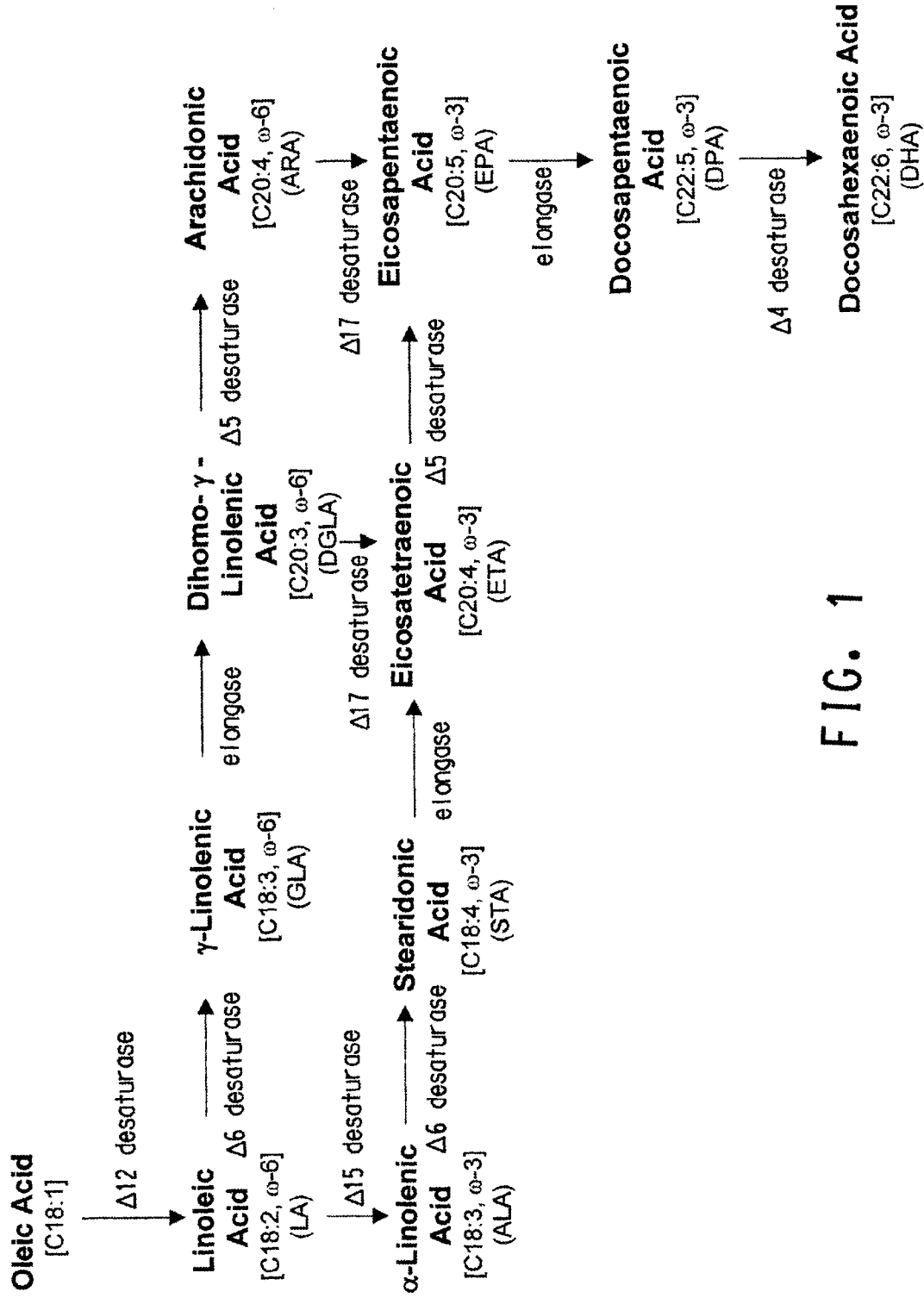
FIG. 1 illustrates the ω-3 and ω-6 fatty acid biosynthetic pathways.

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode some or all of the following enzymes: Δ12 desaturase, Δ6 desaturase, elongase, Δ5 desaturase, Δ17 desaturase, Δ15 desaturase, Δ9 desaturase and Δ4 desaturase. A representative pathway is illustrated in FIG. 1, providing for the conversion of oleic acid through various intermediates to DHA and which demonstrates how both ω-3 and ω-6 fatty acids may be produced from a common source.

The term "desaturase" refers to a polypeptide component of a multi-enzyme complex that can desaturate one or more fatty acids to produce a mono- or polyunsaturated fatty acid or precursor of interest. Despite use of the omega-reference system throughout the specification in reference to specific fatty acids, it is more convenient to indicate the activity of a desaturase by counting from the carboxyl end of the substrate using the delta-system. Of particular interest herein are: 1.) Δ17 desaturases that desaturate a fatty acid between the $17^{th}$ and $18^{th}$ carbon atom numbered from the carboxyl-terminal end of the molecule and which, for example, catalyze the conversion of ARA to EPA and/or DGLA to ETA; 2.) Δ6 desaturases that catalyze the conversion of LA to GLA and/or ALA to STA; 3.) Δ5 desaturases that catalyze the conversion of DGLA to ARA and/or ETA to EPA; 4.) Δ4 desaturases that catalyze the conversion of DPA to DHA; 5.) Δ12 desaturases that catalyze the conversion of oleic acid to LA; 6.) Δ15 desaturases that catalyze the conversion of LA to ALA; and 7.) Δ9 desaturases that catalyze the conversion of palmitate to palmitoleic acid (16:1) and/or stearate to oleic acid (18:1).

The term "elongase" refers to a polypeptide component of a multi-enzyme complex that can elongate a fatty acid carbon chain to produce a mono- or polyunsaturated fatty acid that is 2 carbons longer than the fatty acid substrate that the elongase acts upon. This process of elongation occurs in a multi-step mechanism in association with fatty acid synthase, whereby CoA is the acyl carrier (Lassner et al., *The Plant Cell* 8:281-292 (1996)). Briefly, malonyl-CoA is condensed with a long-chain acyl-CoA to yield $CO_2$ and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongases are the conversion of GLA to DGLA, STA to ETA and EPA to DPA. Accordingly, elongases can have different specificities (e.g., a $C_{16/18}$ elongase will prefer a $C_{16}$ substrate, a $C_{18/20}$ elongase will prefer a $C_{18}$ substrate and a $C_{20/22}$ elongase will prefer a $C_{20}$ substrate).

The term "high affinity elongase" refers to an elongase whose substrate specificity is preferably for GLA (with DGLA as a product of the elongase reaction). One such elongase is described in WO 00/12720.

The terms "conversion efficiency" and "percent substrate conversion" refer to the efficiency by which a particular enzyme (e.g., a desaturase or elongase) can convert substrate to product. The conversion efficiency is measured according to the following formula: ([product]/[substrate+product])*100, where 'product' includes the immediate product and all products in the pathway derived from it.

The term "oleaginous" refers to those organisms that tend to store their energy source in the form of lipid (Weete, In: Fungal Lipid Biochemistry, $2^{nd}$ ed., Plenum, 1980). Generally, the cellular PUFA content of these microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)).

The term "oleaginous yeast" refers to those microorganisms classified as yeasts that can accumulate at least 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The term "fermentable carbon source" means a carbon source that a microorganism will metabolize to derive energy. Typical carbon sources of the invention include, but are not limited to: monosaccharides, oligosaccharides, polysaccharides, alkanes, fatty acids, esters of fatty acids, monoglycerides, diglycerides, triglycerides, carbon dioxide, methanol, formaldehyde, formate and carbon-containing amines.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Within the context of the present invention, genes and DNA coding regions are codon-optimized for optimal expression in *Yarrowia* sp. using the information collected in Table 4.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993). In general, a "substantial portion" of a nucleotide sequence comprises enough of the sequence (e.g., 20-30 contiguous nucleotides) to specifically identify and/or isolate a nucleic acid fragment comprising the sequence. The instant specification teaches partial or complete nucleotide sequences encoding one or more particular proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures; or automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "3' non-coding sequences" or "transcription terminator" refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment(s) of the invention. Expression may also refer to translation of mRNA into a polypeptide.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be (but are not limited to) intracellular localization signals.

"Transformation" refers to the transfer of a nucleic acid molecule into a host organism, resulting in genetically stable inheritance. The nucleic acid molecule may be a plasmid that replicates autonomously, for example; or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

"Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "altered biological activity" will refer to an activity, associated with a protein encoded by a nucleotide sequence which can be measured by an assay method, where that activity is either greater than or less than the activity associated with the native sequence. "Enhanced biological activity" refers to an altered activity that is greater than that associated with the native sequence. "Diminished biological activity" is an altered activity that is less than that associated with the native sequence.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215:403-410 (1990)); 3.) DNASTAR (DNASTAR, Inc., Madison, Wis.); and 4.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual,* 2nd ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Microbial Biosynthesis of Fatty Acids

In general, lipid accumulation in oleaginous microorganisms is triggered in response to the overall carbon to nitrogen ratio present in the growth medium. When cells have exhausted available nitrogen supplies (e.g., when the carbon to nitrogen ratio is greater than about 40), the depletion of cellular adenosine monophosphate (AMP) leads to the cessation of AMP-dependent isocitrate dehydrogenase activity in the mitochondria and the accumulation of citrate, transport of citrate into the cytosol and subsequent cleavage of the citrate by ATP-citrate lyase to yield acetyl-CoA. Acetyl-CoA is the principle building block for de novo biosynthesis of fatty acids. Although any compound that can effectively be metabolized to produce acetyl-CoA can serve as a precursor of fatty acids, glucose is the primary source of carbon in this type of reaction. Glucose is converted to pyruvate via glycolysis and pyruvate is then transported into the mitochondria where it can be converted to acetyl-CoA by pyruvate dehydrogenase. Since acetyl-CoA cannot be transported directly across the mitochondrial membrane into the cytoplasm, the two carbons from acetyl-CoA condense with oxaloacetate to yield citrate (catalyzed by citrate synthase). Citrate is transported directly into the cytoplasm, where it is cleaved by ATP-citrate lyase to regenerate acetyl-CoA and oxaloacetate. The oxaloacetate reenters the tricarboxylic acid cycle, via conversion to malate.

The synthesis of malonyl-CoA is the first committed step of fatty acid biosynthesis, which takes place in the cytoplasm. Malonyl-CoA is produced via carboxylation of acetyl-CoA by acetyl-CoA carboxylase. Fatty acid synthesis is catalyzed by a multi-enzyme fatty acid synthase complex ("FAS") and occurs by the condensation of eight two-carbon fragments (acetyl groups from acetyl-CoA) to form a 16-carbon saturated fatty acid, palmitate. More specifically, FAS catalyzes a series of 7 reactions, which involve the following (Smith, S. *FASEB J*, 8(15):1248-59 (1994)):

1. Acetyl-CoA and malonyl-CoA are transferred to the acyl carrier peptide (ACP) of FAS. The acetyl group is then transferred to the malonyl group, forming β-ketobutyryl-ACP and releasing $CO_2$.
2. The β-ketobutyryl-ACP undergoes reduction (via β-ketoacyl reductase) and dehydration (via β-hydroxyacyl dehydratase) to form a trans-monounsaturated fatty acyl group.
3. The double bond is reduced by NADPH, yielding a saturated fatty-acyl group two carbons longer than the initial one. The butyryl-group's ability to condense with a new malonyl group and repeat the elongation process is then regenerated.
4. When the fatty acyl group becomes 16 carbons long, a thioesterase activity hydrolyses it, releasing free palmitate.

Palmitate (16:0) is the precursor of longer chain saturated and unsaturated fatty acids (e.g., stearic (18:0), palmitoleic (16:1) and oleic (18:1) acids) through the action of elongases and desaturases present in the endoplasmic reticulum membrane. Palmitate and stearate are converted to their unsatuared derivatives, palmitoleic (16:1) and oleic (18:1) acids, respectively, by the action of a Δ9 desaturase.

Triacylglycerols (the primary storage unit for fatty acids) are formed by the esterification of two molecules of acyl-CoA to glycerol-3-phosphate to yield 1,2-diacylglycerol phosphate (commonly identified as phosphatidic acid). The phosphate is then removed, by phosphatidic acid phosphatase, to yield 1,2-diacylglycerol. Triacylglycerol is formed upon the addition of a third fatty acid by the action of a diacylglycerol-acyl transferase.

Biosynthesis of Omega Fatty Acids

Simplistically, the metabolic process that converts LA to GLA, DGLA and ARA (the ω-6 pathway) and ALA to STA, ETA, EPA, DPA and DHA (the ω-3 pathway) involves elongation of the carbon chain through the addition of carbon atoms and desaturation of the molecule through the addition of double bonds (FIG. 1). This requires a series of special desaturation and elongation enzymes present in the endoplasmic reticulim membrane.

ω-6 Fatty Acids

Oleic acid is converted to LA (18:2), the first of the ω-6 fatty acids, by the action of a Δ12 desaturase. Subsequent ω-6 fatty acids are produced as follows: 1.) LA is converted to GLA by the activity of a Δ6 desaturase; 2.) GLA is converted to DGLA by the action of an elongase; and 3.) DGLA is converted to ARA by the action of a Δ5 desaturase.

ω-3 Fatty Acids

Linoleic acid (LA) is converted to ALA, the first of the ω-3 fatty acids, by the action of a Δ15 desaturase. Subsequent ω-3 fatty acids are produced in a series of steps similar to that for the ω-6 fatty acids. Specifically: 1.) ALA is converted to STA by the activity of a Δ6 desaturase; 2.) STA is converted to ETA by the activity of an elongase; and 3.) ETA is converted to EPA by the activity of a Δ5 desaturase. Alternatively, ETA and EPA can be produced from DGLA and ARA, respectively, by the activity of a Δ17 desaturase. EPA can be further converted to DHA by the activity of an elongase and a Δ4 desaturase.

Genes Involved in Omega Fatty Acid Production

Many microorganisms, including algae, bacteria, molds and yeasts, can synthesize PUFAs and omega fatty acids in the ordinary course of cellular metabolism. Particularly well-studied are fungi including *Schizochytrium aggregatm*, species of the genus *Thraustochytrium* and *Morteriella alpina*. Additionally, many dinoflagellates (Dinophyceaae) naturally produce high concentrations of PUFAs. As such, a variety of genes involved in oil production have been identified through genetic means and the DNA sequences of some of these genes are publicly available (non-limiting examples are shown below in Table 2):

TABLE 2

Some Publicly Available Genes Involved In PUFA Production

| GenBank Accession No. | Description |
|---|---|
| AY131238 | *Argania spinosa* Δ6 desaturase |
| Y055118 | *Echium pitardii* var. *pitardii* Δ6 desaturase |
| AY055117 | *Echium gentianoides* Δ6 desaturase |
| AF296076 | *Mucor rouxii* Δ6 desaturase |
| AF007561 | *Borago officinalis* Δ6 desaturase |
| L11421 | *Synechocystis* sp. Δ6 desaturase |
| NM_031344 | *Rattus norvegicus* Δ6 fatty acid desaturase |
| AF465283, AF465281, AF110510 | *Mortierella alpina* Δ6 fatty acid desaturase |
| AF465282 | *Mortierella isabellina* Δ6 fatty acid desaturase |
| AF419296 | *Pythium irregulare* Δ6 fatty acid desaturase |
| AB052086 | *Mucor circinelloides* D6d mRNA for Δ6 fatty acid desaturase |
| AJ250735 | *Ceratodon purpureus* mRNA for Δ6 fatty acid desaturase |
| AF126799 | *Homo sapiens* Δ6 fatty acid desaturase |
| AF126798 | *Mus musculus* Δ6 fatty acid desaturase |
| AF199596, AF226273 | *Homo sapiens* Δ5 desaturase |
| AF320509 | *Rattus norvegicus* liver Δ5 desaturase |
| AB072976 | *Mus musculus* D5D mRNA for Δ5 desaturase |
| AF489588 | *Thraustochytrium* sp. ATCC21685 Δ5 fatty acid desaturase |
| AJ510244 | *Phytophthora megasperma* mRNA for Δ5 fatty acid desaturase |
| AF419297 | *Pythium irregulare* Δ5 fatty acid desaturase |
| AF07879 | *Caenorhabditis elegans* Δ5 fatty acid desaturase |
| AF067654 | *Mortierella alpina* Δ5 fatty acid desaturase |
| AB022097 | *Dictyostelium discoideum* mRNA for Δ5 fatty acid desaturase |
| AF489589.1 | *Thraustochytrium* sp. ATCC21685 Δ4 fatty acid desaturase |
| AY332747 | *Pavlova lutheri* Δ4 fatty acid desaturase (des1) mRNA |
| AAG36933 | *Emericella nidulans* oleate Δ12 desaturase |
| AF110509, AB020033 | *Mortierella alpina* Δ12 fatty acid desaturase mRNA |
| AAL13300 | *Mortierella alpina* Δ12 fatty acid desaturase |
| AF417244 | *Mortierella alpina* ATCC 16266 Δ12 fatty acid desaturase gene |
| AF161219 | *Mucor rouxii* Δ12 desaturase mRNA |
| X86736 | *Spiruline platensis* Δ12 desaturase |
| AF240777 | *Caenorhabditis elegans* Δ12 desaturase |
| AB007640 | *Chlamydomonas reinhardtii* Δ12 desaturase |
| AB075526 | *Chlorella vulgaris* Δ12 desaturase |
| AP002063 | *Arabidopsis thaliana* microsomal Δ12 desaturase |
| NP_441622, BAA18302, BAA02924 | *Synechocystis* sp. PCC 6803 Δ15 desaturase |
| AAL36934 | *Perilla frutescens* Δ15 desaturase |
| AF338466 | *Acheta domesticus* Δ9 desaturase 3 mRNA |
| AF438199 | *Picea glauca* desaturase Δ9 (Des9) mRNA |
| E11368 | *Anabaena* Δ9 desaturase |
| E11367 | *Synechocystis* Δ9 desaturase |
| D83185 | *Pichia angusta* DNA for Δ9 fatty acid desaturase |
| U90417 | *Synechococcus vulcanus* Δ9 acyl-lipid fatty acid desaturase (desC) gene |
| AF085500 | *Mortierella alpina* Δ9 desaturase mRNA |
| AY504633 | *Emericella nidulans* Δ9 stearic acid desaturase (sdeB) gene |
| NM_069854 | *Caenorhabditis elegans* essential fatty acid desaturase, stearoyl-CoA desaturase (39.1 kD) (fat-6) complete mRNA |
| AF230693 | *Brassica oleracea* cultivar Rapid Cycling stearoyl-ACP desaturase (Δ9-BO-1) gene, exon sequence |
| AX464731 | *Mortierella alpina* elongase gene (also WO 02/08401) |
| NM_119617 | *Arabidopsis thaliana* fatty acid elongase 1 (FAE1) (At4g34520) mRNA |
| NM_134255 | *Mus musculus* ELOVL family member 5, elongation of long chain fatty acids (yeast) (Elovl5), mRNA |
| NM_134383 | *Rattus norvegicus* fatty acid elongase 2 (rELO2), mRNA |
| NM_134382 | *Rattus norvegicus* fatty acid elongase 1 (rELO1), mRNA |
| NM_068396, NM_068392, NM_070713, NM_068746, NM_064685 | *Caenorhabditis elegans* fatty acid ELOngation (elo-6), (elo-5), (elo-2), (elo-3), and (elo-9) mRNA |

Additionally, the patent literature provides many additional DNA sequences of genes (and/or details concerning several of the genes above and their methods of isolation) involved in PUFA production. See, for example: U.S. Pat. No. 5,968,809 (Δ6 desaturases); U.S. 2003/0196217 A1 (Δ17 desaturase); U.S. Pat. No. 5,972,664 and U.S. Pat. No. 6,075,183 (Δ5 desaturases); WO 91/13972 and U.S. Pat. No. 5,057,419 (Δ9 desaturases); WO 93/11245 (Δ15 desaturases); WO 94/11516, U.S. Pat. No. 5,443,974 and WO 03/099216 (Δ12 desaturases); WO 02/090493 (Δ4 desaturases); and, WO 00/12720 and U.S. 2002/0139974A1 (elongases). Each of these patents and applications are herein incorporated by reference in their entirety.

As will be obvious to one skilled in the art, the particular functionalities required to be introduced into a host organism for production of a particular PUFA final product will depend on the host cell (and its native PUFA profile and/or desaturase profile), the availability of substrate and the desired end product(s). As described in U.S. Provisional Application 60/467, 677 (incorporated entirely herein by reference) and as shown in FIG. 1, LA, GLA, DGLA, ARA, ALA, STA, ETA, EPA, DPA and DHA may all be produced in oleaginous yeasts, by introducing various combinations of the following PUFA enzyme functionalities: a Δ4 desaturase, a Δ5 desaturase, a Δ6 desaturase, a Δ12 desaturase, a Δ15 desaturase, a Δ17 desaturase, a Δ9 desaturase and/or an elongase. One skilled in the art will be able to identify various candidate genes encoding each of the above enzymes, according to publicly available literature (e.g., GenBank), the patent literature, and experimental analysis of microorganisms having the ability to produce PUFAs. The sequences may be derived from any source, e.g., isolated from a natural source (from bacteria, algae, fungi, plants, animals, etc.), produced via a semi-synthetic route, or synthesized de novo. However, as will be obvious to one of skill in the art, heterologous genes will be expressed with variable efficiencies in an alternate host. Thus, ω-3 and/or ω-6 PUFA production may be optimized by selection of a particular desaturase or elongase whose level of expression in a heterologous host is preferred relative to the expression of an alternate desaturase or elongase in the host organism of interest.

Although the particular source of the desaturase and elongase gene introduced into the host is not critical, considerations for choosing a specific polypeptide having desaturase or elongase activity include: 1.) the substrate specificity of the polypeptide; 2.) whether the polypeptide or a component thereof is a rate-limiting enzyme; 3.) whether the desaturase or elongase is essential for synthesis of a desired PUFA; and/or 4.) co-factors required by the polypeptide. The expressed polypeptide preferably has parameters compatible with the biochemical environment of its location in the host cell. For example, the polypeptide may have to compete for substrate with other enzymes in the host cell. Analyses of the $K_M$ and specific activity of the polypeptide are therefore considered in determining the suitability of a given polypeptide for modifying PUFA production in a given host cell. The polypeptide used in a particular host cell is one that can function under the biochemical conditions present in the intended host cell but otherwise can be any polypeptide having desaturase or elongase activity capable of modifying the desired PUFA.

For the purposes of the work herein, however, wherein the ultimate goal is the development of an oleaginous yeast that accumulates oils enriched in ω-3 and/or ω-6 fatty acids, it was desirable to identify polypeptides having desaturase and elongase activity that function relatively efficiently in oleaginous yeast. Thus, various desaturases and elongases were expressed in an oleaginous yeast and screened for their ability to produce ω-3 and/or ω-6 fatty acids in substrate-feeding trials. Once suitable enzymes had been identified (based on overall percent substrate conversion), these genes were then subjected to the codon-optimization techniques described infra to further optimize the expression of each enzyme in the alternate oleaginous yeast host. This enabled maximal production of ω-3 and/or ω-6 fatty acids.

One skilled in the art will appreciate that the specific PUFA genes selected for codon-optimization herein are only exemplary and not intended to be limiting to the invention herein; numerous other heterologous desaturases (having Δ4, Δ5, Δ6, Δ9, Δ12, Δ15 and/or Δ17 desaturase activity) and elongases from variable sources could be codon-optimized to improve their expression in an oleaginous yeast host.

Codon-Optimization of Omega Fatty Acid Genes for Expression in Oleaginous Yeast

As is well known to one of skill in the art, use of host-preferred codons can substantially enhance the expression of the foreign gene encoding the polypeptide. In general, host-preferred codons can be determined within a particular host species of interest by examining codon usage in proteins (preferably those expressed in the largest amount) and determining which codons are used with highest frequency. Then, the coding sequence for a polypeptide of interest having desaturase or elongase activity can be synthesized in whole or in part using the codons preferred in the host species. Thus, the method of optimizing a gene for expression in a particular host organism of interest generally requires the following steps:

a) obtaining the sequences of nucleotide coding regions and corresponding polypeptides for the particular host organism of interest to form a database of codons;

b) analyzing the database of codons to determine which codons preferentially encode each amino acid;

c) obtaining the sequence of a gene (e.g., a desaturase or elongase) to be expressed in the particular host organism of interest;

d) replacing non-preferred codons in the sequence of step (c) with those preferred codons of step (b) wherein the gene is codon-optimized for expression in the particular host organism of interest.

All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

For the purposes of the present invention, it was desirable to modify a portion of the codons encoding particular polypeptides having PUFA desaturase and elongase activity that were to be expressed in a foreign host, such that the modified polypeptides used codons that were preferred by the alternate host (i.e., oleaginous yeasts). Specifically, it was desirable to modify a portion of the codons encoding the polypeptides having Δ17 desaturase activity, Δ6 desaturase activity and elongase activity to enhance the expression of the genes in *Yarrowia lipolytica*. Thus, the *Y. lipolytica* codon usage profile was determined, as shown in Table 4 (Example 3). In addition, nucleotide sequences surrounding the translational initiation codon 'ATG' have been found to affect expression in yeast cells. If a polypeptide is poorly expressed in yeast, the nucleotide sequences of exogenous genes can be modified to include an efficient yeast translation initiation sequence to obtain optimal gene expression. Thus, for further optimization of gene expression in *Y. lipolytica*, the consensus sequence around the 'ATG' initiation codon was also determined (FIG. 4; SEQ ID NO:122).

Based on the *Y. lipolytica* codon usage profile and the consensus sequence around the 'ATG' initiation codon, the nucleic acid sequence of a Δ17 desaturase gene, a Δ6 desaturase gene and an elongase gene were modified to employ host-preferred codons. More specifically, the *Mortierella alpina* (ATCC #16266) Δ6 desaturase (GenBank Accession No. AF465281; U.S. Pat. No. 5,968,809) was chosen to introduce the enzymatic capability for converting LA to GLA and/or ALA to STA. This wildtype desaturase has 457 amino acids (SEQ ID NO:2) and a predicted molecular weight of 51.8 kD; in the codon-optimized gene created herein, 152 bp of the 1374 bp coding region (corresponding to 144 codons) were codon-optimized and the translation initiation site was modified. In like manner, the wildtype *Saprolegnia diclina* (ATCC #56851) Δ17 desaturase (SEQ ID NO:4; U.S. 2003/0196217 A1) was chosen to introduce the enzymatic capability for converting DGLA to ETA and/or ARA to EPA; however, the translation initiation site was modified and 127 bp of the 1077 bp coding region (comprising 117 codons) were codon-optimized. Finally, the wildtype *M. alpina* high affinity PUFA elongase (GenBank Accession No. AX464731; WO 00/12720), having 318 amino acids (SEQ ID NO:6) and a predicted molecular weight of 40.5 kD, was selected for optimization of its expression in oleaginous yeasts for conversion of GLA to DGLA, STA to ETA and/or EPA to DPA. Specifically, 94 bp of the 957 bp coding region (corresponding to 85 codons) were codon-optimized and the translation initiation site was modified. Thus, the present invention comprises the complete sequences of the synthetic codon-optimized genes as reported in the accompanying Sequence Listing, the complement of those complete sequences, and substantial portions of those sequences.

The skilled artisan will appreciate that the optimization method described herein will be equally applicable to other genes (e.g., genes in the ω-3/ω-6 fatty acid biosynthetic pathway), and that modulation of the *S. diclina* Δ17 desaturase and *M. alpina* Δ6 desaturase and *M. alpina* elongase are only exemplary.

Optimization of Codon-Optimized Genes Via Gene Mutation

Although codon-optimization is a useful means to produce a polypeptide having desaturase or elongase activity, respectively, in vivo with more desirable physical and kinetic parameters for function in an oleaginous yeast, additional means are available to further enhance a polypeptide's activity in a host cell. Specifically, methods for synthesizing sequences and bringing sequences together are well established in the literature. For example, in vitro mutagenesis and selection, site-directed mutagenesis, error prone PCR (Melnikov et al., *Nucleic Acids Research*, 27(4):1056-1062 (Feb. 15, 1999)), "gene shuffling" or other means can be employed to obtain mutations of naturally occurring or codon-optimized desaturase or elongase genes. This could permit production of a desaturase or elongase polypeptide, respectively, having e.g., a longer half-life or a higher rate of production of a desired PUFA in vivo.

If desired, the regions of a codon-optimized desaturase or elongase polypeptide important for enzymatic activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after the 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site-directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis also can be used for identifying regions of a desaturase or elongase polypeptide important for activity. A mutated construct is expressed, and the ability of the resulting altered protein to function as a desaturase or elongase is assayed. Such structure-function analysis can determine which regions may be deleted, which regions tolerate insertions, and which point mutations allow the mutant protein to function in substantially the same way as the native (or codon-optimized) desaturase or elongase.

Microbial Production of ω-3 and/or ω-6 Fatty Acids

Microbial production of ω-3 and/or ω-6 fatty acids has several advantages over purification from natural sources such as fish or plants. For example:

1.) Many microbes are known with greatly simplified oil compositions compared with those of higher organisms, making purification of desired components easier;
2.) Microbial production is not subject to fluctuations caused by external variables, such as weather and food supply;
3.) Microbially produced oil is substantially free of contamination by environmental pollutants;
4.) Microbes can provide PUFAs in particular forms which may have specific uses; and,
5.) Microbial oil production can be manipulated by controlling culture conditions, notably by providing particular substrates for microbially expressed enzymes, or by addition of compounds or genetic engineering approaches to suppress undesired biochemical pathways.

In addition to these advantages, production of ω-3 and/or ω-6 fatty acids from recombinant microbes provides the ability to alter the naturally occurring microbial fatty acid profile by providing new biosynthetic pathways in the host or by suppressing undesired pathways, thereby increasing levels of desired PUFAs, or conjugated forms thereof, and decreasing levels of undesired PUFAs. For example, it is possible to modify the ratio of ω-3 to ω-6 fatty acids so produced, produce either ω-3 or ω-6 fatty acids exclusively while eliminating production of the alternate omega fatty acid, or engineer production of a specific PUFA without significant accumulation of other PUFA downstream or upstream products.

Expression Systems, Cassettes and Vectors

The codon-optimized genes and gene products of the instant sequences described herein may be produced in heterologous microbial host cells, particularly in the cells of oleaginous yeasts (e.g., *Yarrowia lipolytica*). Expression in recombinant microbial hosts may be useful for the production of various PUFA pathway intermediates, or for the modulation of PUFA pathways already existing in the host for the synthesis of new products heretofore not possible using the host.

Microbial expression systems and expression vectors containing regulatory sequences that direct high level expression of foreign proteins are well known to those skilled in the art. Any of these could be used to construct chimeric genes for production of any of the gene products of the instant codon-optimized sequences. These chimeric genes could then be introduced into appropriate microorganisms via transformation to provide high-level expression of the encoded enzymes.

Accordingly, it is expected that introduction of chimeric genes encoding the PUFA biosynthetic pathway (e.g., the codon-optimized Δ6 desaturase, Δ17 desaturase, and elongase described herein), under the control of the appropriate promoters will result in increased production of ω-3 and/or ω-6 fatty acids. It is contemplated that it will be useful to express various combinations of the instant codon-optimized genes together in a host microorganism.

Additionally, it is contemplated that a vector may also comprise one or more genes that encode other enzymes, in addition to one or more of the codon-optimized genes described herein. For example, it may be desirable for an expression cassette to be constructed comprising genes encoding one or more of the following enzymatic activities: a Δ4 desaturase, a Δ5 desaturase, a Δ6 desaturase, a Δ12 desaturase, a Δ15 desaturase, a Δ17 desaturase, a Δ9 desaturase and/or an elongase (wherein any of these genes may optionally be codon-optimized for enhanced expression in a particular host organism). As is well known to one skilled in the art, the particular genes included within a particular expression cassette will depend on the host cell (and its PUFA profile and/or desaturase profile), the availability of substrate and the desired end product(s).

As such, the present invention encompasses a method of producing PUFAs comprising exposing a fatty acid substrate to the PUFA enzyme(s) described herein, such that the substrate is converted to the desired fatty acid product. Thus, each PUFA gene and corresponding enzyme product described herein can be used directly or indirectly for the production of PUFAs. Direct production of PUFAs occurs wherein the fatty acid substrate is converted directly into the desired fatty acid product without any intermediate steps or pathway intermediates. For example, production of EPA would occur in a host cell which produces or which is provided ARA, by adding or introducing into said cell an expression cassette that provides Δ17 desaturase activity.

In contrast, multiple genes encoding the PUFA biosynthetic pathway may be used in combination, such that a series of reactions occur to produce a desired PUFA. For example, expression cassette(s) encoding elongase, Δ5 desaturase, Δ17 desaturase and Δ4 desaturase activity (wherein each gene is optionally codon-optimized for expression in the host) would enable a host cell that naturally produces GLA, to instead produce DHA (such that GLA is converted to DGLA by an elongase; DGLA may then be converted to ARA by a Δ5 desaturase; ARA is then converted to EPA by a Δ17 desaturase, which may in turn be converted to DPA by an elongase; and DPA would be converted to DHA by a Δ4 desaturase). In a preferred embodiment, wherein the host cell is an oleaginous yeast, expression cassettes encoding each of the enzymes necessary for PUFA biosynthesis will need to be introduced into the organism, since naturally produced PUFAs in these organisms are limited to 18:2 fatty acids (i.e., LA), and less commonly, 18:3 fatty acids (i.e., ALA). Alternatively, substrate feeding may be required.

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker, and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

Initiation control regions or promoters which are useful to drive expression of desaturase and/or elongase ORFs in the desired host cell are numerous and familiar to those skilled in the art. Virtually any promoter capable of directing expression of these genes in the selected host cell is suitable for the present invention. Expression in a host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species. The transcriptional initiation regulatory regions can be obtained, for example, from: 1.) genes in the glycolytic pathway, such as alcohol dehydrogenase, glyceraldehyde-3-phosphate-dehydrogenase (see U.S. Patent Application No. 60/482,263), phosphoglycerate mutase (see U.S. Patent Application No. 60/482,263), fructose-bisphosphate aldolase (see U.S. Patent Application No. 60/519,971), phosphoglucose-isomerase, phosphoglycerate kinase, etc.; or, 2.) regulatable genes such as acid phosphatase, lactase, metallothionein, glucoamylase, the translation elongation factor EF1-α (TEF) protein (U.S. Pat. No. 6,265,185), ribosomal protein S7 (U.S. Pat. No. 6,265,185), etc. Any one of a number of regulatory sequences can be used, depending upon whether constitutive or induced transcription is desired, the efficiency of the promoter in expressing the ORF of interest, the ease of construction and the like.

Optimal gene expression in yeast can be obtained by modifying the nucleotide sequences surrounding the translational initiation codon 'ATG' of exogenous genes such that they include an efficient yeast translation initiation sequence. Specifically, the expression of an inefficiently expressed gene can be increased by site-directed mutagenesis, wherein the inefficiently expressed gene is fused in-frame to an endogenous yeast gene, preferably a highly expressed gene. Alternatively, as demonstrated in the invention herein in *Yarrowia lipolytica*, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation in the host organism; and 5.) the intrinsic stability of the cloned gene protein within the host cell. Each of these types of modifications are encompassed in the present invention, as means to further optimize expression of codon-optimized PUFA biosynthetic pathway enzymes.

Transformation of Microbial Hosts

Once the DNA encoding a codon-optimized desaturase or elongase polypeptide suitable for expression in an oleaginous yeast has been obtained, it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology*, 194:186-187 (1991)]), protoplast fusion, bolistic impact, electroporation, microinjection, or any other method that introduces the gene of interest into the host cell. More specific teachings applicable for oleaginous yeasts (i.e., *Yarrowia lipolytica*) include U.S. Pat. Nos. 4,880,741 and 5,071,764 and Chen, D. C. et al. (*Appl Microbiol Biotechnol.* 48(2):232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. The marker protein may be expressed alone or as a fusion to another protein. The marker protein can be detected by: 1.) its enzymatic activity (e.g., β-galactosidase can convert the substrate X-gal [5-bromo-4-chloro-3-indolyl-β-D-galactopyranoside] to a colored product; luciferase can convert luciferin to a light-emitting product); or 2.) its light-producing or modifying characteristics (e.g., the green fluorescent protein of *Aequorea victoria* fluoresces when illuminated with blue light). Alternatively, antibodies can be used to detect the marker protein or a molecular tag on, for example, a protein of interest. Cells expressing the marker protein or tag can be selected, for example, visually, or by techniques such as FACS or panning using antibodies. For selection of yeast transformants, any marker that functions in yeast may be used. Desirably, resistance to kanamycin, hygromycin and the amino glycoside G418 are of interest, as well as ability to grow on media lacking uracil or leucine.

Following transformation, substrates suitable for the gene products of the instant codon-optimized sequences (and optionally other PUFA enzymes that are expressed within the host cell) may be produced by the host either naturally or transgenically, or they may be provided exogenously.

Metabolic Engineering of ω-3 and/or ω-6 Fatty Acid Biosynthesis in Microbes

Knowledge of the codon-optimized sequences of the present genes and the methodology necessary to optimize other PUFA genes for expression in oleaginous yeasts will be useful for manipulating ω-3 and/or ω-6 fatty acid biosynthesis in oleaginous yeasts, and particularly, in *Yarrowia lipolytica*. This may require metabolic engineering directly within the PUFA biosynthetic pathway or additional manipulation of pathways that contribute carbon to the PUFA biosynthetic pathway. Methods useful for manipulating biochemical pathways are well known to those skilled in the art.

Techniques to Up-Regulate Desirable Biosynthetic Pathways

Additional copies of desaturase and elongase genes may be introduced into the host to increase the output of ω-3 and/or ω-6 fatty acid biosynthetic pathways. Expression of the desaturase or elongase genes also can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141). Yet another approach to increase expression of the desaturase or elongase genes, as demonstrated in the instant invention, is to increase the translational efficiency of the encoded mRNAs by replacement of codons in the native gene with those for optimal gene expression in the selected host microorganism.

Techniques to Down-Regulate Undesirable Biosynthetic Pathways

Conversely, biochemical pathways competing with the ω-3 and/or ω-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA). For gene disruption, a foreign DNA fragment (typically a selectable marker gene) is inserted into the structural gene to be disrupted in order to interrupt its coding sequence and thereby functionally inactivate the gene. Transformation of the disruption cassette into the host cell results in replacement of the functional native gene by homologous recombination with the non-functional disrupted gene (see, for example: Hamilton et al. *J. Bacteriol.* 171:4617-4622 (1989); Balbas et al. *Gene* 136:211-213 (1993); Gueldener et al. *Nucleic Acids Res.* 24:2519-2524 (1996); and Smith et al. *Methods Mol. Cell. Biol.* 5:270-277 (1996)).

Antisense technology is another method of down-regulating genes when the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based. For example, cells may be exposed to UV radiation and then screened for the desired phenotype. Mutagenesis with chemical agents is also effective for generating mutants and commonly used substances include chemicals that affect nonreplicating DNA (e.g., $HNO_2$ and $NH_2OH$), as well as agents that affect replicating DNA (e.g., acridine dyes, notable for causing frameshift mutations). Specific methods for creating mutants using radiation or chemical agents are well documented in the art. See, for example: Thomas D. Brock in *Biotechnology: A Textbook of Industrial Microbiology*, $2^{nd}$ ed. (1989) Sinauer Associates: Sunderland, Mass.; or Deshpande, Mukund V., *Appl. Biochem. Biotechnol.*, 36:227 (1992).

Another non-specific method of gene disruption is the use of transposable elements or transposons. Transposons are genetic elements that insert randomly into DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available [see, for example: 1.) The Primer Island Transposition Kit, available from Perkin Elmer Applied Biosystems, Branchburg, N.J., based upon the yeast Ty1 element; 2.) The Genome Priming System, available from New England Biolabs, Beverly, Mass., based upon the bacterial transposon Tn7; and 3.) the EZ::TN Transposon Insertion Systems, available from Epicentre Technologies, Madison, Wis., based upon the Tn5 bacterial transposable element].

Within the context of the present invention, it may be useful to modulate the expression of the fatty acid biosynthetic pathway by any one of the methods described above. For example, the present invention provides codon-optimized genes encoding key enzymes in the biosynthetic pathways leading to the production of ω-3 and/or ω-6 fatty acids. These codon-optimized genes include a Δ6 desaturase, Δ17 desaturase and PUFA elongase. It will be particularly useful to express these genes in oleaginous yeasts that do not naturally possess ω-3 and/or ω-6 fatty acid biosynthetic pathways and modulate the expression of these and other PUFA biosynthetic genes, to maximize production of preferred PUFA products using various means for metabolic engineering of the host organism. Likewise, to maximize PUFA production with these genes, it may be necessary to disrupt pathways that compete for the carbon flux directed toward PUFA biosynthesis.

Preferred Microbial Hosts for Recombinant Expression of Codon-Optimized Genes

Host cells for expression of the instant codon-optimized genes and nucleic acid fragments may include microbial hosts that grow on a variety of feedstocks, including simple or complex carbohydrates, organic acids and alcohols, and/or hydrocarbons over a wide range of temperature and pH values. Although the genes described in the instant invention have been codon-optimized for expression in an oleaginous yeast, and in particular *Yarrowia lipolytica*, it is contemplated that because transcription, translation and the protein biosynthetic apparatus is highly conserved, any bacteria, yeast and/or filamentous fungus will be a suitable host for expression of the present nucleic acid fragment(s).

Preferred microbial hosts are oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon and Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis*, and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 82(1):43-9 (2002)).

Fermentation Processes for PUFA Production

The transformed microbial host cell is grown under conditions that optimize desaturase and elongase activities and produce the greatest and the most economical yield of the preferred PUFAs. In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids, and various commercial sources of fatty acids including vegetable oils (e.g., soybean oil) and animal fats. Additionally, the carbon source may include one-carbon sources (e.g., carbon dioxide, methanol, formaldehyde, formate and carbon-containing amines) for which metabolic conversion into key biochemical intermediates has been demonstrated. Hence it is contemplated that the source of carbon utilized in the present invention may encompass a wide variety of carbon-containing sources and will only be limited by the choice of the host organism. Although all of the above mentioned carbon sources and mixtures thereof are expected to be suitable in the present invention, preferred carbon sources are sugars and/or fatty acids. Most preferred is glucose and/or fatty acids containing between 10-22 carbons.

Nitrogen may be supplied from an inorganic (e.g., $(NH_4)_2SO_4$) or organic source (e.g., urea or glutamate). In addition to appropriate carbon and nitrogen sources, the fermentation media must also contain suitable minerals, salts, cofactors, buffers, vitamins, and other components known to those skilled in the art suitable for the growth of the microorganism and promotion of the enzymatic pathways necessary for PUFA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast. In this approach, the first stage of the fermentation is dedicated to the generation and accumulation of cell mass and is characterized by rapid cell growth and cell division. In the second stage of the fermentation, it is preferable to establish conditions of nitrogen deprivation in the culture to promote high levels of lipid accumulation. The effect of this nitrogen deprivation is to reduce the effective concentration of AMP in the cells, thereby reducing the activity of the NAD-dependent isocitrate dehydrogenase of mitochondria. When this occurs, citric acid will accumulate, thus forming abundant pools of acetyl-CoA in the cytoplasm and priming fatty acid synthesis. Thus, this phase is characterized by the cessation of cell division followed by the synthesis of fatty acids and accumulation of oil.

Although cells are typically grown at about 30° C., some studies have shown increased synthesis of unsaturated fatty acids at lower temperatures (Yongmanitchai and Ward, *Appl. Environ. Microbiol.* 57:419-25 (1991)). Based on process economics, this temperature shift should likely occur after the first phase of the two-stage fermentation, when the bulk of the organisms' growth has occurred.

It is contemplated that a variety of fermentation process designs may be applied, where commercial production of omega fatty acids using the instant codon-optimized genes is desired. For example, commercial production of PUFAs from a recombinant microbial host may be produced by a batch, fed-batch or continuous fermentation process.

A batch fermentation process is a closed system wherein the media composition is set at the beginning of the process and not subject to further additions beyond those required for maintenance of pH and oxygen level during the process. Thus, at the beginning of the culturing process the media is inoculated with the desired organism and growth or metabolic activity is permitted to occur without adding additional sources (i.e., carbon and nitrogen sources) to the medium. In batch processes the metabolite and biomass compositions of the system change constantly up to the time the culture is terminated. In a typical batch process, cells proceed through a static lag phase to a high-growth log phase and finally to a stationary phase, wherein the growth rate is diminished or halted. Left untreated, cells in the stationary phase will eventually die. A variation of the standard batch process is the fed-batch process, wherein the carbon source is continually added to the fermentor over the course of the fermentation process. A fed-batch process is also suitable in the present invention. Fed-batch processes are useful when catabolite repression is apt to inhibit the metabolism of the cells or where it is desirable to have limited amounts of source in the media at any one time. Measurement of the carbon source concentration in fed-batch systems is difficult and therefore may be estimated on the basis of the changes of measurable factors such as pH, dissolved oxygen and the partial pressure of waste gases (e.g., $CO_2$). Batch and fed-batch culturing methods are common and well known in the art and examples may be found in Thomas D. Brock in *Biotechnology: A Textbook of Industrial Microbiology*, 2nd ed., (1989) Sinauer Associates: Sunderland, Mass.; or Deshpande, Mukund V., *Appl. Biochem. Biotechnol.*, 36:227 (1992), herein incorporated by reference.

Commercial production of omega fatty acids using the instant codon-optimized genes may also be accomplished by a continuous fermentation process wherein a defined media is continuously added to a bioreactor while an equal amount of culture volume is removed simultaneously for product recovery. Continuous cultures generally maintain the cells in the log phase of growth at a constant cell density. Continuous or semi-continuous culture methods permit the modulation of one factor or any number of factors that affect cell growth or end product concentration. For example, one approach may limit the carbon source and allow all other parameters to moderate metabolism. In other systems, a number of factors affecting growth may be altered continuously while the cell concentration, measured by media turbidity, is kept constant. Continuous systems strive to maintain steady state growth and thus the cell growth rate must be balanced against cell loss due to media being drawn off the culture. Methods of modulating nutrients and growth factors for continuous culture processes, as well as techniques for maximizing the rate of product formation, are well known in the art of industrial microbiology and a variety of methods are detailed by Brock, supra.

Purification of PUFAs

The PUFAs may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463-491 (1992)). A brief review of downstream processing is also available by A. Singh and O. Ward (*Adv. Appl. Microbiol.* 45:271-312 (1997)).

In general, means for the purification of PUFAs may include extraction with organic solvents, sonication, supercritical fluid extraction (e.g., using carbon dioxide), saponification and physical means such as presses, or combinations thereof. Of particular interest is extraction with methanol and chloroform in the presence of water (E. G. Bligh & W. J. Dyer, *Can. J. Biochem. Physiol.* 37:911-917 (1959)). Where desirable, the aqueous layer can be acidified to protonate negatively-charged moieties and thereby increase partitioning of desired products into the organic layer. After extraction, the organic solvents can be removed by evaporation under a stream of nitrogen. When isolated in conjugated forms, the products may be enzymatically or chemically cleaved to release the free fatty acid or a less complex conjugate of interest, and can then be subject to further manipulations to produce a desired end product. Desirably, conjugated forms of fatty acids are cleaved with potassium hydroxide.

If further purification is necessary, standard methods can be employed. Such methods may include extraction, treatment with urea, fractional crystallization, HPLC, fractional distillation, silica gel chromatography, high-speed centrifugation or distillation, or combinations of these techniques. Protection of reactive groups, such as the acid or alkenyl groups, may be done at any step through known techniques (e.g., alkylation, iodination). Methods used include methylation of the fatty acids to produce methyl esters. Similarly, protecting groups may be removed at any step. Desirably, purification of fractions containing GLA, STA, ARA, DHA and EPA may be accomplished by treatment with urea and/or fractional distillation.

DESCRIPTION OF PREFERRED EMBODIMENTS

The ultimate goal of the work described herein is the development of an oleaginous yeast that accumulates oils enriched in ω-3 and/or ω-6 fatty acids. Toward this end, desaturases and elongases of ω-3 and/or ω-6 fatty acid biosynthetic pathways must be identified that function efficiently in oleaginous yeasts, to enable synthesis and accumulation of omega fatty acids in these hosts.

In the present invention, Applicants have demonstrated techniques suitable for codon-optimization of desaturase and elongase genes, wherein the resulting synthetic codon-optimized gene functions with increased conversion efficiency in oleaginous yeast such as *Yarrowia lipolytica*. These methods are embodied in the teachings herein, specifically targeted to the synthesis of a codon-optimized Δ6 desaturase (which has the enzymatic capability of converting LA to GLA and/or ALA to STA), a codon-optimized Δ17 desaturase (responsible for converting DGLA to ETA and/or ARA to EPA) and a codon-optimized high affinity PUFA elongase (capable of transforming GLA to DGLA, STA to ETA and/or EPA to DPA). One skilled in the art would readily be able to apply the techniques described herein to optimize other genes in the ω-3 and/or ω-6 biosynthetic fatty acid pathway to create synthetic genes that would be expected to have increased conversion efficiency when expressed in *Yarrowia*. Thus, the teachings herein would have great utility in the development of an oleaginous yeast that accumulates oils enriched in ω-3 and/or ω-6 fatty acids.

Applicants selected three exemplary wildtype genes for codon-optimization in the model oleaginous yeast, *Yarrowia lipolytica*. Each of these wildtype genes was obtained in plasmids from Ross Products (Columbus, Ohio), as described below in Table 3.

TABLE 3

Genes And Source Plasmids Obtained From Ross Products

| Gene | Organism | Plasmid Comprising Said Gene | Reference |
| --- | --- | --- | --- |
| Δ6 desaturase | *M. alpina* | pCGR5 | U.S. Pat. No. 5,968,809 |
| Elongase | *M. alpina* | pRPB2 | WO 00/12720 |
| Δ17 desaturase | *S. diclina* | pRSP19 | U.S. 2003/0196217 A1 |

Following confirmation of each wildtype enzyme's activity in the microbial host (by substrate-feeding trials), each gene was codon-optimized (wherein at least 9% of the native codons were modified to employ host-preferred codons).

Codon-optimization of the Δ6 desaturase, Δ17 desaturase and high affinity PUFA elongase genes first required determination of the codon usage and signature of structural genes in *Yarrowia lipolytica*. Then codon-optimized genes were designed and synthesized in vitro using a protocol that substantially shortens the amount of time necessary to synthesize a full-length gene sequence. This protocol is not limited to the particular genes synthesized herein and thus should be broadly applicable for a variety of general uses. The basic steps involved for in vitro gene synthesis consisted of the following:

1. Multiple pairs of oligonucleotides (each about 100 bp in length) are synthesized. Each oligonucleotide sequence corresponds with a portion of the full-length gene sequence that is to be synthesized; and, each sense-strand oligonucleotide sequence has a ~4 bp overlap with the corresponding antisense-strand oligonucleotide at the 5' end of the sequence.
2. The 5' and 3' end of all oligonucleotides are phosphorylated in a kinase reaction and then each pair of sense and antisense oligonucleotides are subjected to an individual annealing reaction, to produce short (~100 bp) fragments of double-stranded DNA.
3. Pools of the short (~100 bp) fragments of double-stranded DNA are then ligated together, using the ~4 bp overlap that was designed upon synthesis of the oligonucleotides, to yield longer (~300-400 bp) fragments of DNA.
4. Following ligation, the longer fragments are amplified by PCR, the products of which are cloned into an appropriate vector and transformed into host cells.
5. Plasmid DNA containing each PCR product is purified from the host cells and then subjected to restriction enzyme digestion for isolation of the PCR product corresponding to each ~300-400 bp fragment of the gene to be synthesized.
6. The ~300-400 bp fragments of the gene to be synthesized are ligated together and then subjected to PCR amplification to produce the entire full-length synthetic sequence.

Upon synthesis of the codon-optimized Δ6 desaturase, Δ17 desaturase and high affinity PUFA elongase genes, each was individually transformed into *Yarrowia lipolytica*. Feeding experiments (using the appropriate substrate) determined that the codon-optimized genes were more efficiently expressed in *Y. lipolytica* than the corresponding native wildtype genes. Specifically, the codon-optimized Δ6 desaturase converted approximately 40% more LA to GLA than its wild-type counterpart, the codon-optimized Δ17 desaturase converted about 2-fold more ARA to EPA than the wildtype enzyme and the codon-optimized high affinity PUFA elongase converted approximately 57% more GLA to DGLA when expressed in *Y. lipolytica* under the same biological conditions.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by:

1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology*, 2$^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified.

*E. coli* TOP10 cells and *E. coli* electromax DH10B cells were obtained from Invitrogen (Carlsbad, Calif.). Max Efficiency competent cells of *E. coli* DH5α were obtained from GIBCO/BRL (Gaithersburg, Md.). *E. coli* (XL1-Blue) competent cells were purchased from the Stratagene Company (San Diego, Calif.). *E. coli* strains were typically grown at 37° C. on Luria Bertani (LB) plates.

A leucine autotrophic strain of *Yarrowia lipolytica* was purchased from the American Type Culture Collection (Rockville, Md.; ATCC #76982) and used for functional assays. *Y. lipolytica* strains were usually grown at 28° C. on YPD agar (1% yeast extract, 2% bactopeptone, 2% glucose, 2% agar). For selection of transformants, minimal medium (0.17% yeast nitrogen base (DIFCO Laboratories, Detroit, Mich.) without ammonium sulfate or amino acids, 2% glucose, 0.1% proline, pH 6.1) was used. Supplements of adenine, leucine, lysine and/or uracil were added to a final concentration of 0.01%.

General molecular cloning was performed according to standard methods (Sambrook et al., supra). Oligonucleotides were synthesized by Sigma-Genosys (Spring, Tex.). Site-directed mutagenesis was performed using Stratagene's QuickChange™ Site-Directed Mutagenesis kit, per the manufacturers' instructions. When polymerase chain reaction (PCR) or site-directed mutagenesis was involved in subcloning, the constructs were sequenced to confirm that no errors had been introduced to the sequence. PCR products were cloned into Promega's pGEM-T-easy vector (Madison, Wis.).

Manipulations of genetic sequences were accomplished using the suite of programs available from the Genetics Computer Group Inc. (Wisconsin Package Version 9.0, Genetics Computer Group (GCG), Madison, Wis.). The GCG program "Pileup" was used with the gap creation default value of 12, and the gap extension default value of 4. The GCG "Gap" or "Bestfit" programs were used with the default gap creation penalty of 50 and the default gap extension penalty of 3. Unless otherwise stated, in all other cases GCG program default parameters were used.

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Example 1

Construction of Plasmids Suitable for Heterologous Gene Expression in *Yarrowia lipolytica*

The plasmid pY5, a derivative of pINA532 (a gift from Dr. Claude Gaillardin, Insitut National Agronomics, Centre de biotechnologie Agro-Industrielle, laboratoire de Genetique Moleculaire et Cellularie INRA-CNRS, F-78850 Thiverval-Grignon, France), was constructed for expression of heterologous genes in *Yarrowia lipolytica*, as diagrammed in FIG. 2.

First, the partially-digested 3598 bp EcoRI fragment containing the ARS18 sequence and LEU2 gene of pINA532 was subcloned into the EcoRI site of pBluescript (Strategene, San Diego, Calif.) to generate pY2.

The TEF promoter (Muller S., et al. *Yeast*, 14: 1267-1283 (1998)) was amplified from *Yarrowia lipolytica* genomic DNA by PCR using TEF5' (SEQ ID NO:7) and TEF3' (SEQ ID NO:8) as primers. PCR amplification was carried out in a 50 μl total volume containing: 100 ng *Yarrowia* genomic DNA, PCR buffer containing 10 mM KCl, 10 mM (NH$_4$)$_2$SO$_4$, 20 mM Tris-HCl (pH 8.75), 2 mM MgSO$_4$, 0.1% Triton X-100, 100 μg/mL BSA (final concentration), 200 μM each deoxyribonucleotide triphosphate, 10 pmole of each primer and 1 μl of PfuTurbo DNA polymerase (Stratagene, San Diego, Calif.). Amplification was carried out as follows: initial denaturation at 95° C. for 3 min, followed by 35 cycles of the following: 95° C. for 1 min, 56° C. for 30 sec, 72° C. for 1 min. A final extension cycle of 72° C. for 10 min was carried out, followed by reaction termination at 4° C. The 418 bp PCR product was ligated into pCR-Blunt to generate pIP-tef. The BamHI/EcoRV fragment of pIP-tef was subcloned into the BamHI/SmaI sites of pY2 to generate pY4.

The XPR2 transcriptional terminator was amplified by PCR using pINA532 as template and XPR5' (SEQ ID NO:9) and XPR3' (SEQ ID NO:10) as primers. The PCR amplification was carried out in a 50 μl total volume, using the components and conditions described above. The 179 bp PCR product was digested with SacII and then ligated into the SacII site of pY4 to generate pY5. Thus, pY5 (shown in FIGS. 2 and 3) is useful as a *Yarrowia-E. coli* shuttle plasmid containing:

1.) a *Yarrowia* autonomous replication sequence (ARS18);

2.) a ColE1 plasmid origin of replication;

3.) an ampicillin-resistance gene (Amp$^R$), for selection in *E. coli*;

4.) a *Yarrowia* LEU2 gene, for selection in *Yarrowia*;

5.) the translation elongation promoter (TEF P), for expression of heterologous genes in *Yarrowia*; and 6.) the extracellular protease gene terminator (XPR2) for transcriptional termination of heterologous gene expression in *Yarrowia*.

pY5-4 and pY5-13 (FIG. 3) were constructed as derivatives of pY5 to faciliate subcloning and heterologous gene expression in *Yarrowia lipolytica*.

Specifically, pY5-4 was constructed by three rounds of site-directed mutagenesis using pY5 as template. A NcoI site located inside the LEU2 reporter gene was eliminated from pY5 using oligonucleotides YL1 and YL2 (SEQ ID NOs:11 and 12) to generate pY5-1. A NcoI site was introduced into pY5-1 between the TEF promoter and XPR2 transcriptional terminator by site-directed mutagenesis using oligonucleotides YL3 and YL4 (SEQ ID NOs:13 and 14) to generate pY5-2. A PacI site was then introduced into pY5-2 between the TEF promoter and XPR2 transcriptional terminator using oligonucleotides YL23 and YL24 (SEQ ID NOs:15 and 16) to generate pY5-4.

pY5-13 was constructed by 6 rounds of site-directed mutagenesis using pY5 as template. Both SalI and ClaI sites were eliminated from pY5 by site-directed mutagenesis using oligonucleotides YL5 and YL6 (SEQ ID NOs:17 and 18) to generate pY5-5. A SalI site was introduced into pY5-5 between the LEU2 gene and the TEF promoter by site-directed mutagenesis using oligonucleotides YL9 and YL10 (SEQ ID NOs:19 and 20) to generate pY5-6. A PacI site was introduced into pY5-6 between the LEU2 gene and ARS18 using oligonucleotides YL7 and YL8 (SEQ ID NOs:21 and 22) to generate pY5-8. A NcoI site was introduced into pY5-8 around the translation start codon of the TEF promoter using oligonucleotides YL3 and YL4 (SEQ ID NOs:13 and 14) to generate pY5-9. The NcoI site inside the LEU2 gene of pY5-9 was eliminated using YL1 and YL2 oligonucleotides (SEQ ID NOs:11 and 12) to generate pY5-12. Finally, a BsiWI site was introduced into pY5-12 between the ColE1 and XPR2 region using oligonucleotides YL61 and YL62 (SEQ ID NOs:23 and 24) to generate pY5-13.

Example 2

Analysis of Conversion Efficiency of Wildtype Δ6 and Δ17 Desaturases and High Affinity PUFA Elongase in *Yarrowia lipolytica*

To ensure functionality of the wildtype Δ6 desaturase, elongase and Δ17 desaturase in *Yarrowia lipolytica* (prior to codon-optimization), conversion efficiency of each wildtype protein was measured. Specifically, the *Mortierella alpina* Δ6 desaturase, *Saprolegnia diclina* Δ17 desaturase and *M. alpina* high affinity PUFA elongase were expressed in the alternate host and screened for activity in substrate-feeding trials. Each enzyme was found to be capable of converting at least 23% of substrate to product.

Wild Type *Mortierella alpina* (Accession #AF465281) Δ6 Desaturase

The 1384 bp NcoI/NotI fragment of pCGR5 (U.S. Pat. No. 5,968,809), which contains the *M. alpina* Δ6 desaturase gene (SEQ ID NO:1), was inserted into the NcoI/NotI sites of pY5-2 (Example 1) to generate pY54.

Wild Type *Saprolegnia diclina* (ATCC #56851) Δ17 Desaturase

The wild type Δ17 desaturase gene of *S. diclina* was amplified from plasmid pRSP19 (US 2003/0196217A1) by PCR using oligonucleotides YL21A (SEQ ID NO:118) and YL22 (SEQ ID NO:119) as primers. The PCR amplification was carried out in a 50 µl total volume, comprising PCR buffer containing: 10 ng template, 10 mM KCl, 10 mM $(NH_4)_2SO_4$, 20 mM Tris-HCl (pH 8.75), 2 mM $MgSO_4$, 0.1% Triton X-100, 100 µg/mL BSA (final concentration), 200 µM each deoxyribonucleotide triphosphate, 10 pmole of each primer and 1 µl of PfuTurbo DNA polymerase (Stratagene, San Diego, Calif.). Amplification was carried out as follows: initial denaturation at 95° C. for 3 min, followed by 35 cycles of the following: 95° C. for 1 min, 56° C. for 30 sec, 72° C. for 1 min. A final extension cycle of 72° C. for 10 min was carried out, followed by reaction termination at 4° C. The PCR products were digested with NcoI/PacI and then ligated to NcoI/PacI-digested pY5-4 (FIG. 3; described in Example 1) to generate pYSD17.

Wild Type *Mortierella alpina* (Accession #AX464731) High Affinity Elongase

Figure 2B:
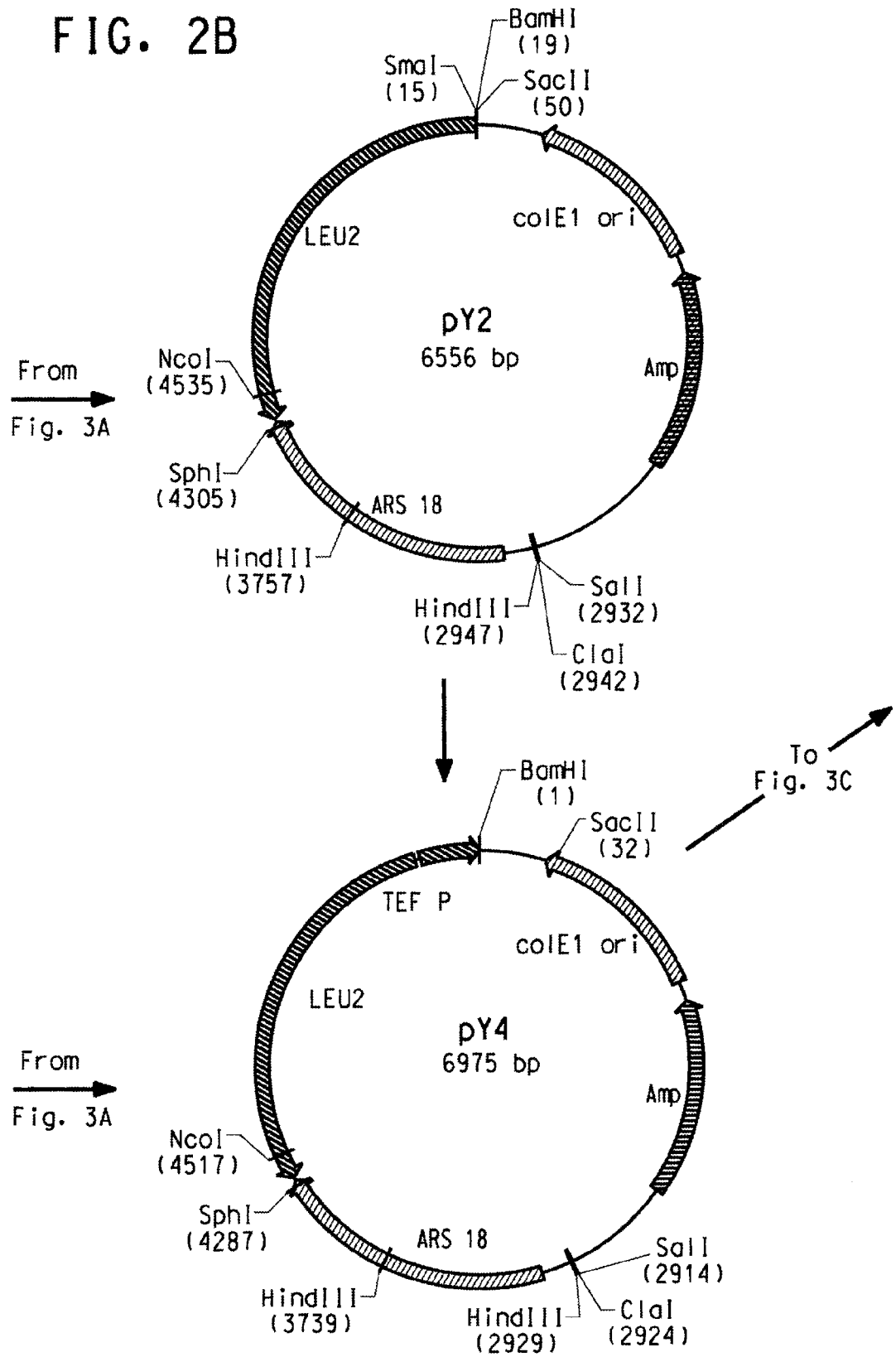
FIG. 2 illustrates the construction of the plasmid vector pY5 for use in *Yarrowia lipolytica*.
Figure 2C:
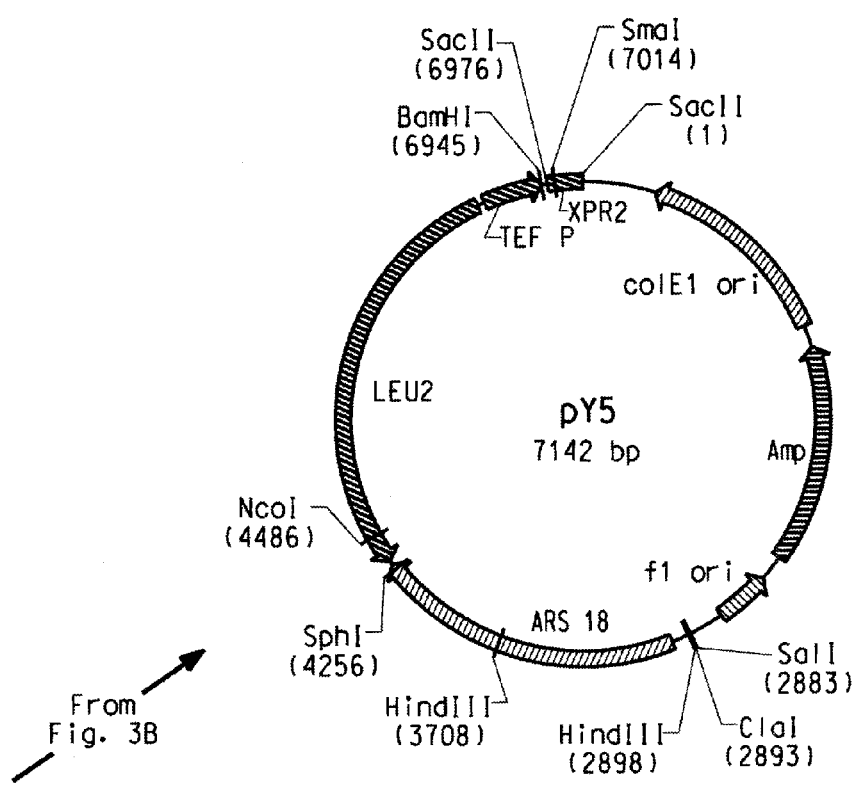
Figure 3:
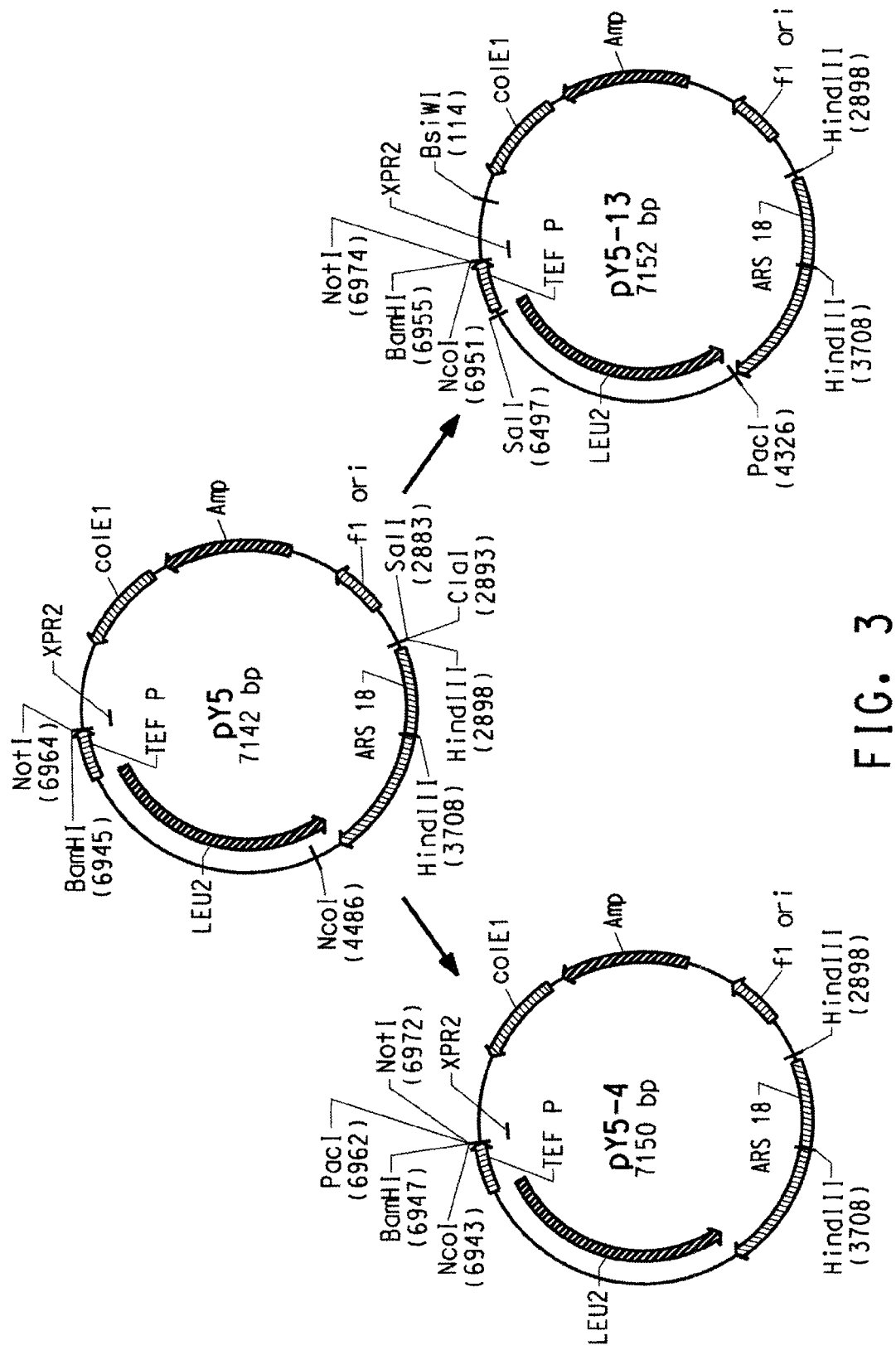
FIG. 3 illustrates the construction of plasmid vectors pY5-13 and pY5-4 for gene expression in *Y. lipolytica*.

The 973 bp NotI fragment of pRPB2 (WO 00/12720), containing the coding region of the *M. alpina* high affinity PUFA elongase gene (SEQ ID NO:5), was inserted into the NotI site of pY5 (Example 1; FIGS. 2 and 3) to generate pY58 (FIG. 13B).

Transformation of *Yarrowia lipolytica*

The plasmids pY54, pYSD17 and pY58 were transformed separately into *Y. lipolytica* ATCC #76982 according to the method of Chen, D. C. et al. (*Appl Microbiol Biotechnol.* 48(2):232-235-(1997)).

Briefly, a leucine auxotroph of *Yarrowia* was streaked onto a YPD plate and grown at 30° C. for approximately 18 hr. Several large loopfuls of cells were scraped from the plate and resuspended in 1 mL of transformation buffer containing:

2.25 mL of 50% PEG, average MW 3350;
0.125 mL of 2 M Li acetate, pH 6.0;
0.125 mL of 2M DTT; and
50 µg sheared salmon sperm DNA.

About 500 ng of plasmid DNA were incubated in 100 µl of resuspended cells, and maintained at 39° C. for 1 hr with vortex mixing at 15 min intervals. The cells were plated onto minimal media plates lacking leucine and maintained at 30° C. for 2 to 3 days.

Determination of Percent Substrate Conversion

Single colonies of transformant *Y. lipolytica* containing pY54, pYSD17 or pY58 were each grown in 3 mL minimal media (20 g/L glucose, 1.7 g/L yeast nitrogen base without amino acids, 1 g/L L-proline, 0.1 g/L L-adenine, 0.1 g/L L-lysine, pH 6.1) at 30° C. to an $OD_{600}$~1.0. For substrate feeding, 100 µl of cells were then subcultured in 3 mL minimal media containing 10 µg of substrate for about 24 hr at 30° C. Cells were subsequently collected by centrifugation and lipids were extracted as described in Bligh, E. G. & Dyer, W. J. (*Can. J. Biochem. Physiol.* 37:911-917 (1959)). Fatty acid methyl esters were prepared by transesterification of the lipid extract with sodium methoxide (Roughan, G., and Nishida I. *Arch Biochem Biophys.* 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min. Percent substrate conversion was determined as: ([product]/[substrate+product])*100).

Percent Substrate Conversion of Wild Type *M. alpina* Δ6 Desaturase

The *M. alpina* Δ6 desaturase converts LA to GLA and/or ALA to STA. *Y. lipolytica* strains containing pY54 were grown as described above (no substrate feeding required) and lipids were analyzed. The results showed that *Yarrowia* strains with pY54 converted about 30% LA to GLA.

Percent Substrate Conversion of Wild Type *S. diclina* Δ17 Desaturase

The *S. diclina* Δ17 desaturase converts ARA to EPA and/or DGLA to ETA. *Y. lipolytica* strains containing pYSD17 were grown from single colonies, subcultured in minimal media containing 10 μg of ARA and subjected to lipid analysis as described above. The results of the ARA feeding experiments showed that *Yarrowia* strains with pYSD17 converted about 23% of intracellular ARA to EPA.

Percent Substrate Conversion of Wild Type *M. alpina* High Affinity Elongase

The *M. alpina* high affinity PUFA elongase converts GLA to DGLA, STA to ETA and/or EPA to DPA. *Y. lipolytica* strains containing pY58 were grown from single colonies, subcultured in minimal media containing 10 μg of GLA and subjected to lipid analysis as described above. The results of the GLA feeding experiments showed that *Yarrowia* strains with pY58 converted about 30% of intracellular GLA to DGLA.

Example 3

Determining the Preferred Codon Usage in *Yarrowia lipolytica*

Approximately 100 genes of *Y. lipolytica* were found in the National Center for Biotechnology Information public database. The coding regions of these genes, comprising 121, 167 bp, were translated by the Editseq program of DNAStar to the corresponding 40,389 amino acids and were tabulated to determine the *Y. lipolytica* codon usage profile shown in Table 4. The column titled "No." refers to the number of times a given codon encodes a particular amino acid in the sample of 40,389 amino acids. The column titled "%" refers to the frequency that a given codon encodes a particular amino acid. Entries shown in bold text represent the codons favored in *Y. lipolytica*.

TABLE 4

Codon Usage In *Yarrowia lipolytica*

| Codon | Amino Acid | No. | % |
|---|---|---|---|
| GCA | Ala (A) | 359 | 11.4 |
| GCC | Ala (A) | 1523 | 48.1 |
| GCG | Ala (A) | 256 | 8.1 |
| GCU | Ala (A) | 1023 | 32.3 |
| AGA | Arg (R) | 263 | 13.2 |
| AGG | Arg (R) | 91 | 4.6 |
| CGA | Arg (R) | 1133 | 56.8 |
| CGC | Arg (R) | 108 | 5.4 |
| CGG | Arg (R) | 209 | 1.0 |
| CGU | Arg (R) | 189 | 9.5 |
| AAC | Ans (N) | 1336 | 84.0 |
| AAU | Ans (N) | 255 | 16.0 |
| GAC | Asp (D) | 1602 | 66.8 |
| GAU | Asp (D) | 795 | 33.2 |
| UGC | Cys (C) | 268 | 53.2 |
| UGU | Cys (C) | 236 | 46.8 |
| CAA | Gln (Q) | 307 | 17.0 |
| CAG | Gln (Q) | 1490 | 83.0 |
| GAA | Glu (E) | 566 | 23.0 |
| GAG | Glu (E) | 1893 | 77.0 |
| GGA | Gly (G) | 856 | 29.7 |
| GGC | Gly (G) | 986 | 34.2 |
| GGG | Gly (G) | 148 | 5.1 |
| GGU | Gly (G) | 893 | 31.0 |
| CAC | His (H) | 618 | 65.5 |
| CAU | His (H) | 326 | 34.5 |
| AUA | Ile (I) | 42 | 2.1 |
| AUC | Ile (I) | 1106 | 53.7 |
| AUU | Ile (I) | 910 | 44.2 |
| CUA | Leu (L) | 166 | 4.7 |
| CUC | Leu (L) | 1029 | 29.1 |
| CUG | Leu (L) | 1379 | 38.9 |

TABLE 4-continued

Codon Usage In *Yarrowia lipolytica*

| Codon | Amino Acid | No. | % |
|---|---|---|---|
| CUU | Leu (L) | 591 | 16.7 |
| UUA | Leu (L) | 54 | 1.5 |
| UUG | Leu (L) | 323 | 9.1 |
| AAA | Lys (K) | 344 | 14.8 |
| AAG | Lys (K) | 1987 | 85.2 |
| AUG | Met (M) | 1002 | 100 |
| UUC | Phe (F) | 996 | 61.1 |
| UUU | Phe (F) | 621 | 38.9 |
| CCA | Pro (P) | 207 | 9.6 |
| CCC | Pro (P) | 1125 | 52.0 |
| CCG | Pro (P) | 176 | 8.2 |
| CCU | Pro (P) | 655 | 30.2 |
| AGC | Ser (S) | 335 | 11.3 |
| AGU | Ser (S) | 201 | 6.8 |
| UCA | Ser (S) | 221 | 7.5 |
| UCC | Ser (S) | 930 | 31.5 |
| UCG | Ser (S) | 488 | 16.5 |
| UCU | Ser (S) | 779 | 26.4 |
| UAA | Term | 38 | 46.9 |
| UAG | Term | 30 | 37.0 |
| UGA | Term | 13 | 16.1 |
| ACA | Thr (T) | 306 | 12.7 |
| ACC | Thr (T) | 1245 | 51.6 |
| ACG | Thr (T) | 269 | 11.1 |
| ACU | Thr (T) | 595 | 24.6 |
| UGG | Trp (W) | 488 | 100 |
| UAC | Tyr (Y) | 988 | 83.2 |
| UAU | Tyr (Y) | 200 | 16.8 |
| GUA | Val (V) | 118 | 4.2 |
| GUC | Val (V) | 1052 | 37.3 |
| GUG | Val (V) | 948 | 33.6 |
| GUU | Val (V) | 703 | 24.9 |

For further optimization of gene expression in *Y. lipolytica*, the consensus sequence around the 'ATG' initiation codon of 79 genes was examined. In FIG. 4, the first 'A' of the underlined ATG translation initiation codon is considered to be +1. Seventy seven percent of the genes analyzed had an "A" in the −3 position, indicating a strong preference for "A" at this position. There was also preference for 'A' or 'C' at the −4, −2 and −1 positions, an 'A', 'C' or 'T' at position +5, and a 'G' or 'C' at position +6. Thus, the preferred consensus sequence of the codon-optimized translation initiation site for optimal expression of genes in *Y. lipolytica* is 'MAMMATGNHS' (SEQ ID NO:122), wherein the nucleic acid degeneracy code used is as follows: M=A/C; S=C/G; H=A/C/T; and N=A/C/G/T.

Example 4

Synthesis of a Codon-Optimized Δ6 Desaturase Gene

The Δ6 desaturase gene from *Mortierella alpina* (SEQ ID NO:1) is 1374 bp in length (U.S. Pat. No. 5,968,809; GenBank#AF465281). A codon-optimized Δ6 desaturase gene was designed, based on the *M. alpina* DNA sequence, according to the *Yarrowia* codon usage pattern, the consensus sequence around the ATG translation initiation codon, and the general rules of RNA stability (Guhaniyogi, G. and J. Brewer, Gene 265(1-2):11-23 (2001)). In addition to modifying the translation initiation site, 152 bp of the 1374 bp coding region (corresponding to 144 codons) were also codon-optimized. A comparison between this codon-optimized gene (SEQ ID NO:25) and the full-length wildtype sequence from *M. alpina* (SEQ ID NO:1) is shown in FIG. 5, wherein nucleotides in bold text correspond to nucleotides that were modified in the codon-optimized gene. None of the modifications in the codon-optimized gene changed the amino acid sequence of the encoded protein (SEQ ID NO:2).

Figure 6:
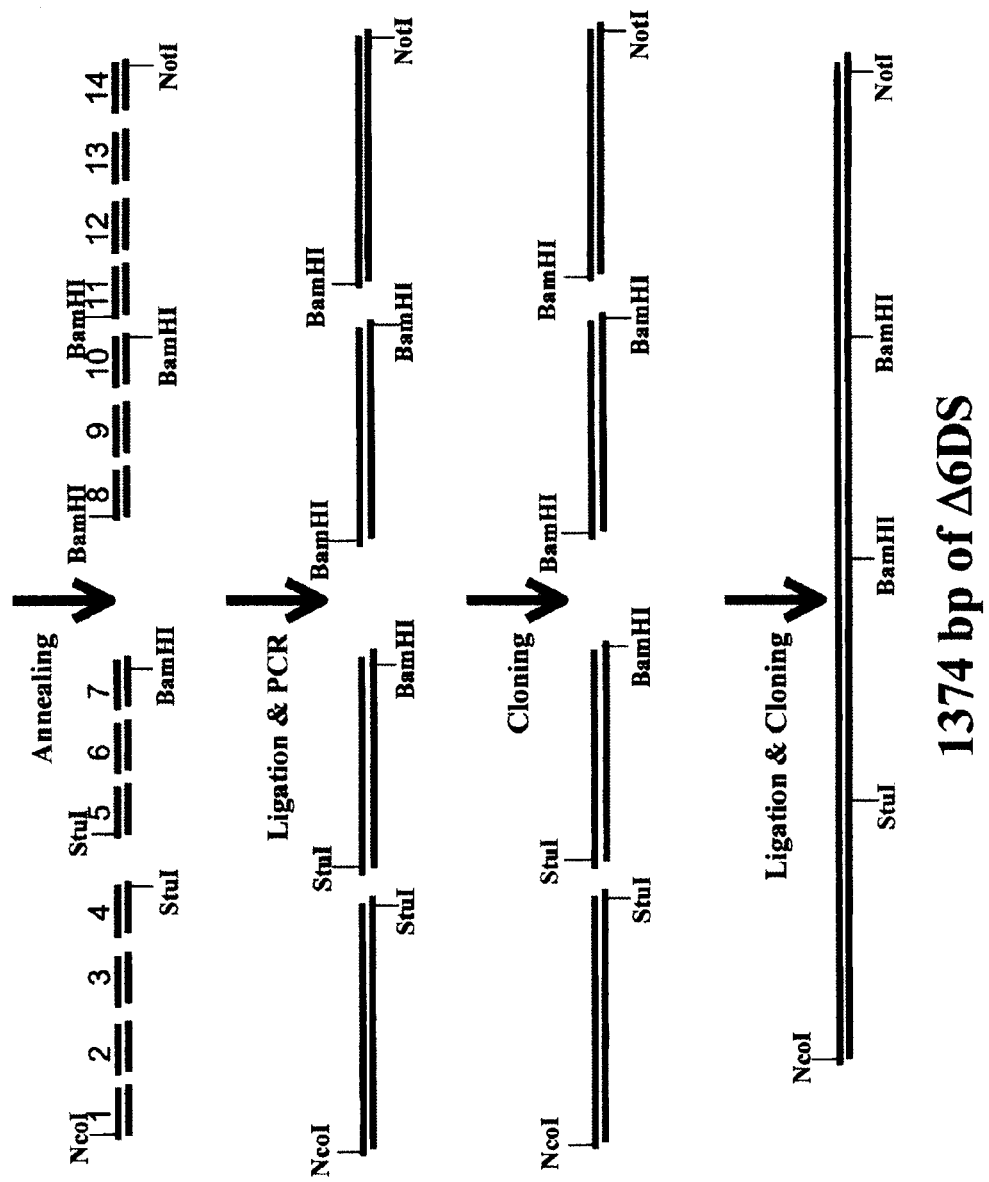
FIG. 6 illustrates the strategy utilized for in vitro synthesis of the codon-optimized Δ6 desaturase gene.

The method used to synthesize the codon-optimized Δ6 desaturase gene is illustrated in FIG. 6. First, fourteen pairs of oligonucleotides were designed to extend the entire length (i.e., 1374 bp) of the codon-optimized coding region of the M. alpina Δ6 desaturase gene (e.g., D6-1A, D6-1B, D6-2A, D6-2B, D6-3A, D6-3B, D6-4A, D6-4B, D6-5A, D6-5B, D6-6A, D6-6B, D6-7A, D6-7B, D6-8A, D6-8B, D6-9A, D6-9B, D6-10A, D6-10B, D6-11A, D6-11B, D6-12A, D6-12B, D6-13A, D6-13B, D6-14A and D6-14B, corresponding to SEQ ID NOs:26-53). Each pair of sense (A) and anti-sense (B) oligonucleotides were complementary, with the exception of a 4 bp overhang at each 5'-end. Primer D6-1A contained a NcoI site at its 5' end; primers D6-4B and D6-5A contained a StuI site; and primers D6-7B, D6-8A, and D6-10B each contained BamHI sites for subsequent subcloning. 100 ng of each oligonucleotide was phosphorylated at 37° C. for 1 hr in a volume of 20 μl containing 50 mM Tris-HCl (pH 7.5), 10 mM MgCl$_2$, 10 mM DTT, 0.5 mM spermidine, 0.5 mM ATP and 10 units of T4 polynucleotide kinase. Each pair of sense and antisense oligonucleotides was mixed and annealed in a thermocycler using the following parameters: 95° C. (2 min), 85° C. (2 min), 65° C. (15 min), 37° C. (15 min), 24° C. (15 min), and 4° C. (15 min). Thus, D6-1A (SEQ ID NO:26) was annealed to D6-1B (SEQ ID NO:27) to produce the double-stranded product "D6-1AB". Similarly, D6-2A (SEQ ID NO:28) was annealed to D6-2B (SEQ ID NO:29) to produce the double-stranded product "D6-2AB", etc.

Four separate pools of annealed, double-stranded oligonucleotides were then ligated together, as shown below:
Pool 1: comprised D6-1AB, D6-2AB, D6-3AB, and D6-4AB;
Pool 2: comprised D6-5AB, D6-6AB, and D6-7AB;
Pool 3: comprised D6-8AB, D6-9AB, and D6-10AB; and
Pool 4: comprised D6-11AB, D6-12AB, D6-13AB, and D6-14AB.

Each pool of annealed oligonucleotides was mixed in a volume of 20 μl with 10 units of T4 DNA ligase and the ligation reaction was incubated overnight at 16° C.

The product of each ligation reaction was then amplified by PCR. Specifically, using the ligated "Pool 1" mixture (i.e., D6-1AB, D6-2AB, D6-3AB and D6-4AB) as template, and oligonucleotides D6-1 (SEQ ID NO:54) and D6-4R (SEQ ID NO:55) as primers, the first portion of the codon-optimized Δ6 desaturase gene was amplified by PCR. The PCR amplification was carried out in a 50 μl total volume, comprising PCR buffer containing 10 mM KCl, 10 mM (NH$_4$)$_2$SO$_4$, 20 mM Tris-HCl (pH 8.75), 2 mM MgSO$_4$, 0.1% Triton X-100, 100 μg/mL BSA (final concentration), 200 μM each deoxyribonucleotide triphosphate, 10 pmole of each primer and 1 μl of PfuTurbo DNA polymerase (Stratagene, San Diego, Calif.). Amplification was carried out as follows: initial denaturation at 95° C. for 3 min, followed by 35 cycles of the following: 95° C. for 1 min, 56° C. for 30 sec, 72° C. for 40 sec. A final extension cycle of 72° C. for 10 min was carried out, followed by reaction termination at 4° C. The 380 bp PCR fragment was subcloned into the pGEM-T easy vector (Promega) to generate pT6(1-4).

Using the ligated "Pool 2" mixture (i.e., D6-5AB, D6-6AB and D6-7AB) as template, and oligonucleotides D6-5 (SEQ ID NO:56) and D6-7R (SEQ ID NO:57) as primers, the second portion of the codon-optimized Δ6 desaturase gene was amplified similarly by PCR and cloned into pGEM-T-easy vector to generate pT6(5-7). Using the "Pool 3" ligation mixture (i.e., D6-8AB, D6-9AB, and D6-10AB) as template, and oligonucleotides D6-8 (SEQ ID NO:58) and D6-10R (SEQ ID NO:59) as primers, the third portion of the codon-optimized Δ6 desaturase gene was amplified similarly by PCR and cloned into pGEM-T-easy vector to generate pT6 (8-10). Finally, using the "Pool 4" ligation mixture (i.e., D6-11AB, D6-12AB, D6-13AB and D6-14AB) as template, and oligonucleotides D6-11 (SEQ ID NO:60) and D6-14R (SEQ ID NO:61) as primers, the forth portion of the codon-optimized Δ6 desaturase gene was amplified similarly by PCR and cloned into pGEM-T-easy vector to generate pT6 (11-14).

Figure 7:
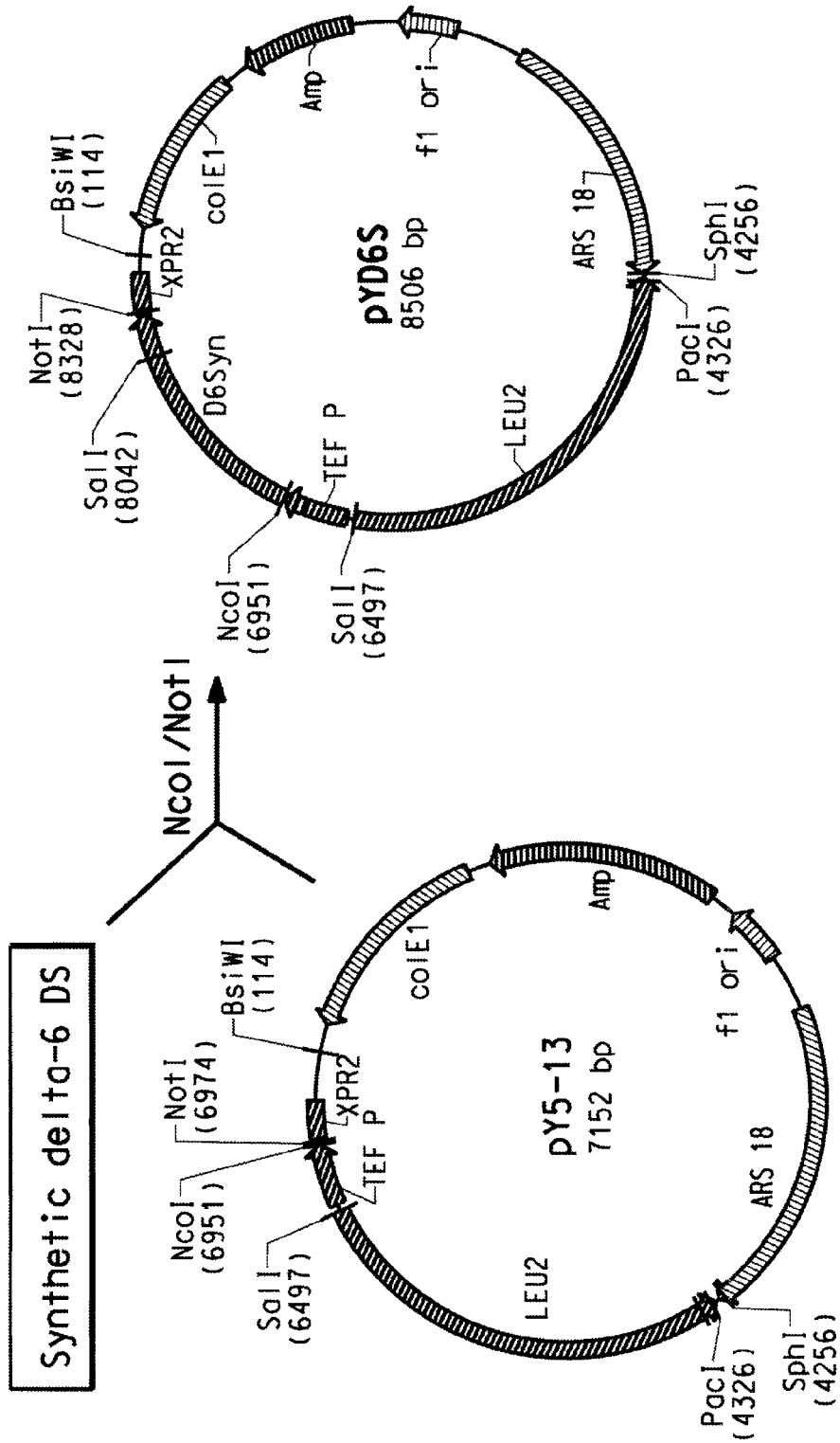
FIG. 7 shows plasmids for expression of the codon-optimized Δ6 desaturase gene in *Y. lipolytica*.

E. coli was transformed separately with pT6(1-4), pT6(5-7), pT6(8-10) and pT6(11-14), and the plasmid DNA isolated from ampicillin-resistant transformants was purified and digested with the appropriate restriction endonucleases to liberate the 380 bp NcoI/StuI fragment of pT6(1-4), the 310 bp StuI/BamHI fragment of pT6(5-7), the 320 bp BamHI fragment of pT6(8-10), and the 410 bp BamHI/NotI fragment of pT6(11-14). These fragments were then combined, ligated together in correct orientation and inserted into the NcoI/NotI sites of pY5-13 to generate pYD6S (FIG. 7).

Example 5

Synthesis of a Codon-Optimized Δ17 Desaturase Gene

The Δ17 desaturase gene from *Saprolegnia diclina* (SEQ ID NO:3) is 1077 bp in length. A codon-optimized Δ17 desaturase gene was designed, based on the *S. diclina* DNA sequence, according to the *Yarrowia* codon usage pattern, the consensus sequence around the ATG translation initiation codon, and the general rules of RNA stability (Guhaniyogi and Brewer, supra). In addition to modification to the translation initiation site, 127 bp of the 1077 bp coding region (comprising 117 codons) were codon-optimized. A comparison between this codon-optimized DNA sequence (SEQ ID NO:62) and the *S. diclina* Δ17 desaturase gene DNA sequence (SEQ ID NO:3) is shown in FIG. 8, wherein nucleotides in bold text correspond to nucleotides that were modified in the codon-optimized gene. None of the modifications in the codon-optimized gene changed the amino acid sequence of the encoded protein (SEQ ID NO:4).

Figure 9:
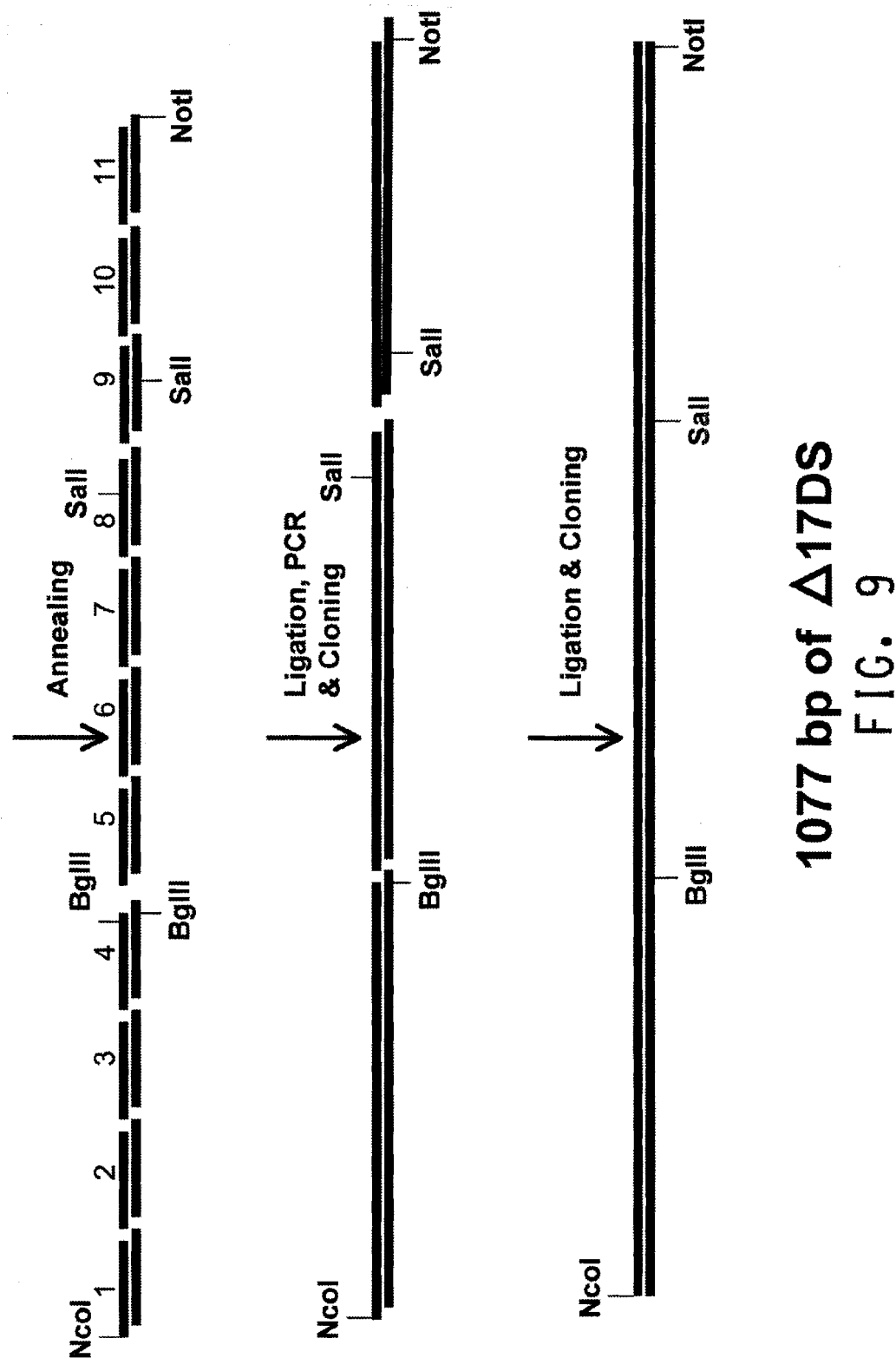
FIG. 9 illustrates the strategy utilized for in vitro synthesis of the codon-optimized Δ17 desaturase gene.

The method used to synthesize the codon-optimized Δ17 desaturase gene is illustrated in FIG. 9. First, eleven pairs of oligonucleotides were designed to extend the entire length of the codon-optimized coding region of the *S. diclina* Δ17 desaturase gene (e.g., D17-1A, D17-1B, D17-2A, D17-2B, D17-3A, D17-3B, D17-4A, D17-4B, D17-5A, D17-5B, D17-6A, D17-6B, D17-7A, D17-7B, D17-8A, D17-8B, D17-9A, D17-9B, D17-10A, D17-10B, D17-11A and D17-11B, corresponding to SEQ ID NOs:63-84). Each pair of sense (A) and anti-sense (B) oligonucleotides were complementary, with the exception of a 4 bp overhang at each 5'-end. Additionally, primers D17-1A, D17-4B, D17-5A, D17-8A and D17-8B also introduced NcoI, BglII and SalI restriction sites for subsequent subcloning, respectively.

Following the methodology used in Example 4,100 ng of each oligonucleotide was phosphorylated with T4 polynucleotide kinase. Each pair of sense and antisense oligonucleotides was then mixed and annealed. Thus, D17-1A (SEQ ID NO:63) was annealed to D17-1B (SEQ ID NO:64) to produce the double-stranded product "D17-1AB". Similarly, D17-2A (SEQ ID NO:65) was annealed to D17-2B (SEQ ID NO:66) to produce the double-stranded product "D17-2AB", etc.

Three separate pools of annealed, double-stranded oligonucleotides were then ligated together, as shown below:

Pool 1: comprised D17-1AB, D17-2AB, D17-3AB and D17-4AB;

Pool 2: comprised D17-5AB, D17-6AB, D17-7AB and D17-8AB; and

Pool 3: comprised D17-9AB, D17-10AB and D17-11AB.

Each pool of annealed oligonucleotides was ligated overnight in a volume of 20 μl at 16° C.

The product of each ligation reaction was then amplified by PCR. Specifically, using the ligated "Pool 1" mixture (i.e., D17-1AB, D17-2AB, D17-3AB and D17-4AB) as template, and oligonucleotides D17-1 (SEQ ID NO:85) and D17-4R (SEQ ID NO:86) as primers, the first portion of the codon-optimized Δ17 desaturase gene was amplified by PCR. The PCR amplification was carried out in a 50 μl total volume, using the PCR conditions and thermocycling program described in Example 4. The 430 bp PCR fragment was subcloned into the pGEM-T easy vector (Promega) to generate pT17(1-4).

Using the ligated "Pool 2" mixture (i.e., D17-5AB, D17-6AB, D17-7AB and D17-8AB) as template, and oligonucleotides D17-5 (SEQ ID NO:87) and D17-8D (SEQ ID NO:88) as primers, the second portion of the codon-optimized Δ17 desaturase gene was amplified similarly by PCR and cloned into pGEM-T-easy vector to generate pT17(5-8). Finally, using the "Pool 3" ligation mixture (i.e., D17-9AB, D17-10AB and D17-11AB) as template, and oligonucleotides D17-8U (SEQ ID NO:89) and D17-11 (SEQ ID NO:90) as primers, the third portion of the codon-optimized Δ17 desaturase gene was amplified similarly by PCR and cloned into pGEM-T-easy vector to generate pT17(9-11).

E. coli was transformed separately with pT17(1-4), pT17(5-8) and pT17(9-11) and the plasmid DNA was isolated from ampicillin-resistant transformants. Plasmid DNA was purified and digested with the appropriate restriction endonucleases to liberate the 420 bp NcoI/BglII fragment of pT17(1-4), the 400 bp BglII/SalI fragment of pT17(5-8) and the 300 bp SalI/NotI fragment of pT17(9-11). These fragments were then combined, ligated together and used as template for amplification of the entire synthetic Δ17 desaturase gene using D17-1 (SEQ ID NO:85) and D17-11 (SEQ ID NO:90) as primers. The PCR amplification was carried out in a 50 μl total volume, using the conditions described above for each portion of the Δ17 desaturase gene and the thermocycling program as follows: initial denaturation at 95° C. for 3 min, followed by 35 cycles of the following: 95° C. for 1 min, 56° C. for 30 sec, 72° C. for 1.1 min. A final extension cycle of 72° C. for 10 min was carried out, followed by reaction termination at 4° C. The 1.1 kB PCR product was digested with NcoI/NotI and subcloned into NcoI/NotI-digested pY5-13 to generate pYSD17S (FIG. 10A).

Figures 10A, 10B:
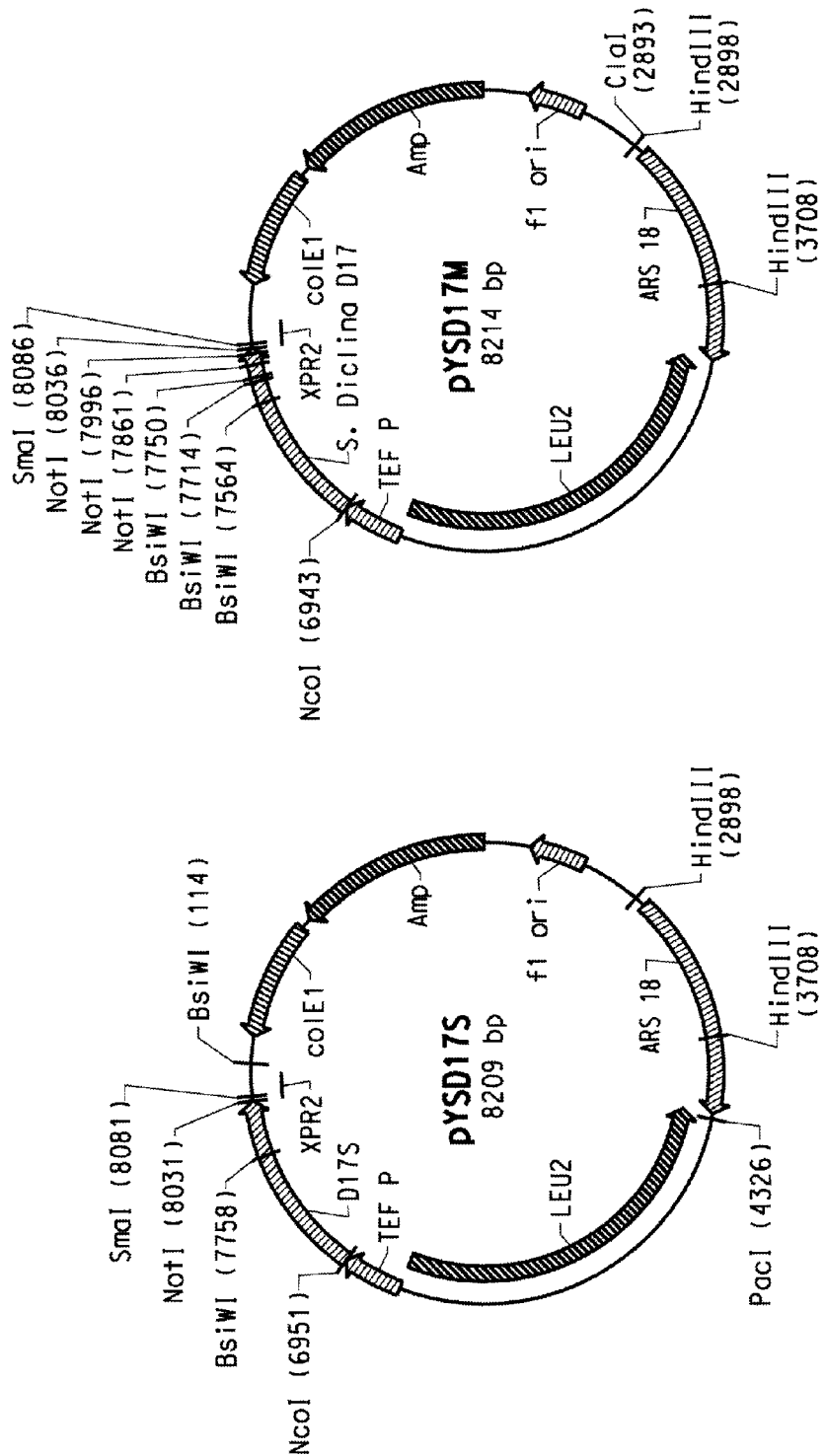
FIG. 10 shows plasmids for expression of the codon-optimized and wildtype Δ17 desaturase genes in *Y. lipolytica*.

As an additional "control" for use in comparative substrate-feeding trials with the wildtype and codon-optimized Δ17 desaturases, the AT-rich PacI site in pYSD17 (described in Example 2) was eliminated by site-directed mutagenesis using YL53 (SEQ ID NO:120) and YL54 (SEQ ID NO:121) as primers to generate pYSD17M (FIG. 10B).

Example 6

Synthesis of a Codon-Optimized High Affinity PUFA Elongase Gene

The high affinity PUFA elongase gene from M. alpina (SEQ ID NO:5) is 957 bp in length (GenBank #AX464731; WO 00/12720). A codon-optimized high affinity PUFA elongase gene was designed, based on the M. alpina DNA sequence, according to the Yarrowia codon usage pattern, the consensus sequence around the 'ATG' translation initiation codon, and the general rules of RNA stability (Guhaniyogi & Brewer, supra). In addition to modifying the translation initiation site, 94 bp of the 957 bp coding region (corresponding to 85 codons) were also codon-optimized. A comparison between this codon-optimized gene (SEQ ID NO:91) and the full-length wildtype sequence from M. alpina (SEQ ID NO:5) is shown in FIG. 11, wherein nucleotides in bold text correspond to nucleotides that were modified in the codon-optimized gene. None of the modifications in the codon-optimized gene changed the amino acid sequence of the encoded protein (SEQ ID NO:6).

Figure 12:
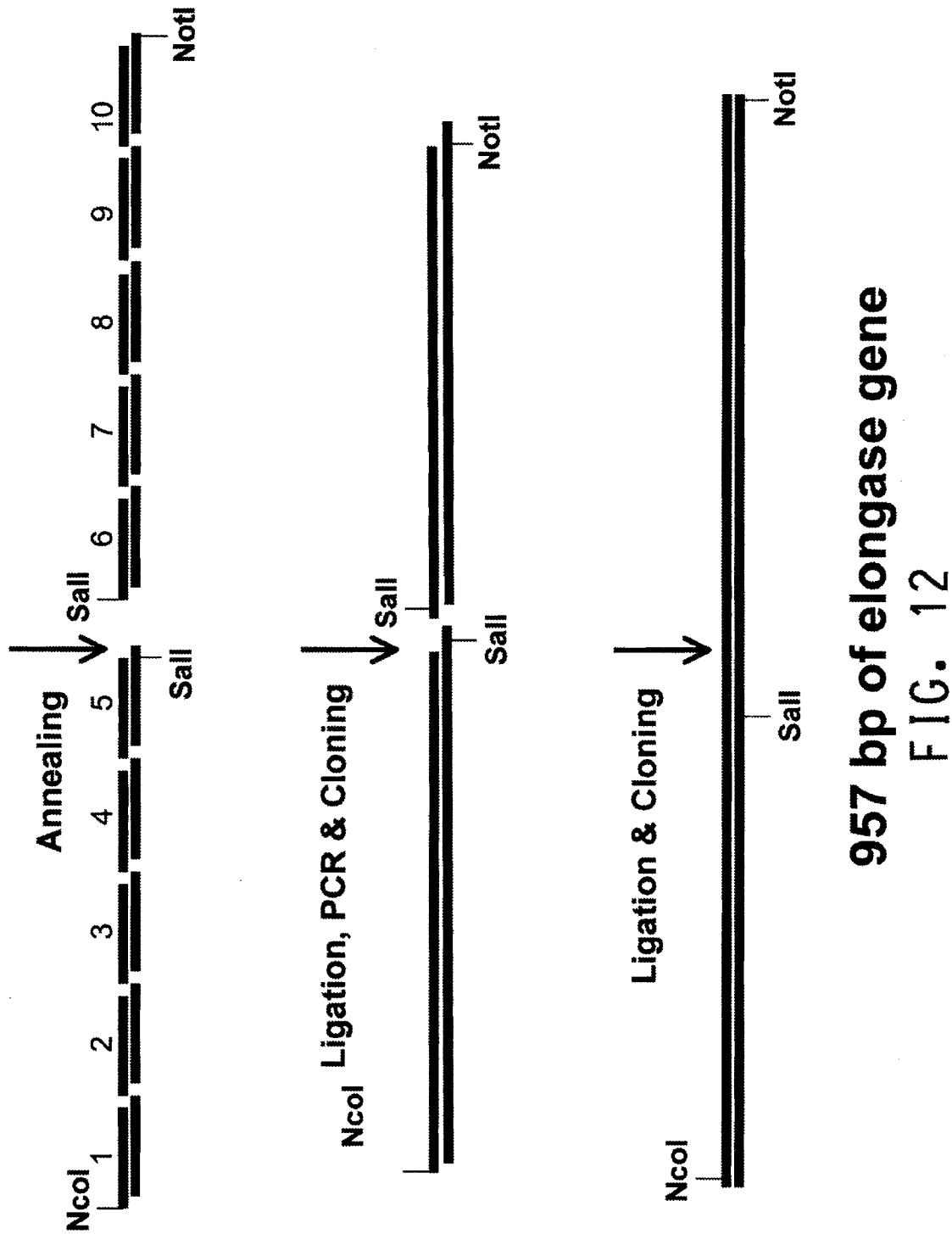
FIG. 12 illustrates the strategy utilized for in vitro synthesis of the codon-optimized elongase gene.

The methodology utilized to synthesize the high affinity elongase gene is shown in FIG. 12. Specifically, ten pairs of oligonucleotides were designed to extend along the length of the M. alpina high affinity elongase coding region (i.e., EL-1A, EL-1B, EL-2A, EL-2B, EL-3A, EL-3B, EL-4A, EL-4B, EL-5A, EL-5B, EL-6A, EL-6B, EL-7A, EL-7B, EL-8A, EL-8B, EL-9A, EL-9B, EL-10A and EL-10B, corresponding to SEQ ID NOs:92-111). Each pair of sense (A) and anti-sense (B) oligonucleotides were complementary, with the exception of a 4 bp overhang at the 5'-end.

Following the methodology of Example 4, 100 ng of each oligonucleotide was phosphorylated with T4 polynucleotide kinase. Then, each pair of sense and anti-sense oligonucleotides was mixed and annealed. Thus, EL-1A (SEQ ID NO:92) was annealed to EL1-1B (SEQ ID NO:93) to produce the double-stranded product "EL-1AB", EL-2A (SEQ ID NO:94) was annealed to EL-2B (SEQ ID NO:95) to produce the double-stranded product "EL-2AB", etc.

Two separate pools of annealed, double-stranded oligonucleotides were then ligated together, as shown below:

Pool 1: comprised EL-1AB, EL-2AB, EL-3AB, EL-4AB and EL-5AB; and

Pool 2: comprised EL-6AB, EL-7AB, EL-8AB, EL-9AB and EL-10AB.

Each pool of annealed oligonucleotides was ligated overnight in a volume of 20 μl with 10 U of T4 DNA ligase at 16° C.

The product of each ligation reaction was then amplified by PCR. Specifically, using the ligated "Pool 1" mixture (i.e., EL-1AB, EL-2AB, EL-3AB, EL-4AB and EL-5AB) as template, and oligonucleotides EL-1 (SEQ ID NO:112) and EL-5R (SEQ ID NO:113) as primers, the first portion of the codon-optimized elongase gene was amplified by PCR. The PCR amplification was carried out in a 50 μl reaction mixture, as described in Example 4. Amplification was carried out as follows: initial denaturation at 95° C. for 3 min, followed by 35 cycles of the following: 95° C. for 1 min, 56° C. for 30 sec, 72° C. for 1 min. A final extension cycle of 72° C. for 10 min was carried out, followed by reaction termination at 4° C. The 500 bp PCR fragment was subcloned into the pGEM-T easy vector (Promega) to generate pTEL(1-5).

Using the ligated "Pool 2" mixture (i.e., EL-6AB, EL-7AB, EL-8AB, EL-9AB and EL-10AB) as template, and oligonucleotides EL-6 (SEQ ID NO:114) and EL-10R (SEQ ID NO:115) as primers, the second portion of the codon-optimized elongase gene was amplified similarly by PCR and subcloned into the pGEM-T easy vector to generate pTEL(6-10).

E. coli cells was transformed separately with pTEL(1-5) and pTEL(6-10) and the plasmid DNA from ampicillin resistant transformants was purified and digested with the appropriate restriction endonucleases to liberate the 500 bp NcoI/SalI fragment of pTEL(1-5) and the 470 bp SalI/NotI fragment of pTEL(6-10). These fragments were then mixed and ligated to NcoI/NotI digested pY5-13 to generate pELS-1.

DNA sequence analysis of the pELS-1 insert identified the presence of a single 'C' to 'T' base substitution at position +65 (wherein the 'A' of the 'ATG' translation codon was designated as +1) that resulted in an amino acid change from Thr (ACC) to Ser (AGC). This mutation was corrected subsequently by site-directed mutagenesis using oligonucleotides EL-M1 (SEQ ID NO: 116) and EL-M2 (SEQ ID NO: 117) as primers to generate pELS (FIG. 13A).

Example 7

Transformation of Yarrowia lipolytica with Codon-Optimized Δ6 Desaturase, Δ17 Desaturase and High Affinity PUFA Elongase Genes Plasmids containing the wildtype and codon-optimized Δ6 desaturase, Δ17 desaturase and high affinity PUFA elongase genes were transformed separately into Y. lipolytica ATCC #76982 according to the methodology described in Example 2. Using this technique, transformants were obtained that contained the following plasmids:

TABLE 5

Summary Of Plasmids In Transformant Yarrowia lipolytica

| Plasmid | Description |
| --- | --- |
| pYSD6--from Example 2 | wildtype Δ6 desaturase |
| pYD6S-from Example 4 | codon-optimized Δ6 desaturase |
| pYSD17-from Example 2 | wildtype Δ17 desaturase |
| pYSD17M-from Example 5 | wildtype Δ17 desaturase, minus AT-rich PacI site |
| pYSD17S-from Example 5 | codon-optimized Δ17 desaturase |
| pY58-from Example 2 | wildtype elongase |
| pELS-from Example 6 | codon-optimized elongase |

Example 8

Analysis of Conversion Efficiency of the Codon-Optimized Δ6 and Δ17 Desaturases and High Affinity Elongase in Yarrowia lipolytica Following comparison of the conversion efficiency of the wildtype and codon-optimized Δ6 desaturase, Δ17 desaturase and high affinity elongase, respectively, it was determined that codon-optimization improved the percent substrate conversion of LA to GLA (Δ6 desaturase) by approximately 40%, ARA to EPA by about 2-fold (Δ17 desaturase) and GLA to DGLA (elongase) by about 57% in Y. lipolytica.

Percent Substrate Conversion with the Codon-Optimized Δ6 Desaturase

Δ6 desaturase converts LA to GLA and/or ALA to STA (see FIG. 1). In order to compare the conversion efficiency of the wildtype and codon-optimized Δ6 desaturase genes, the percent substrate conversion ([product]/[substrate+product])*100) was determined in Yarrowia lipolytica containing each alternate plasmid construct (i.e., pYSD6 or pYD6S). Specifically, Yarrowia lipolytica containing either pYSD6 or pYD6S were grown from single colonies in 3 mL minimal media, subcultured in minimal media containing 10 μg of LA and subjected to lipid analysis as described in Example 2.

The results of the experiments indicated that Yarrowia strains containing pYSD6 converted ~30% substrate LA to GLA (FIG. 14A), while those containing pYD6S converted ~42% LA to GLA (FIG. 14B). On this basis, Yarrowia containing the codon-optimized Δ6 desaturase gene converted approximately 40% more LA than the wild type M. alpina Δ6 desaturase gene in Y. lipolytica.

Percent Substrate Conversion with the Codon-Optimized Δ17 Desaturase

Δ17 desaturase converts DGLA to ETA and/or ARA to EPA (see FIG. 1). In order to compare the conversion efficiency of the wildtype and codon-optimized Δ17 desaturase genes, the percent substrate conversion was determined in Yarrowia lipolytica containing pYSD17, pYSD17M and pYSD17S. Each transformant was grown from single colonies in 3 mL minimal media, subcultured in minimal media containing 10 μg of ARA and subjected to lipid analysis as described in Example 2.

The results of the ARA feeding experiments showed that Yarrowia strains with control plasmids pYSD17 or pYSD17M converted about 23% of intracellular ARA to EPA (FIG. 15A), while those containing the codon-optimized Δ17 desaturase gene on pYSD17S converted about 45% of intracellular ARA to EPA (FIG. 15B). Thus, Yarrowia containing the codon-optimized Δ17 desaturase gene converted about 2-fold more ARA than the strains containing the wild type S. diclina gene.

Percent Substrate Conversion with the Codon-Optimized Elongase

The high affinity PUFA elongase of M. alpina is primarily responsible for catalyzing the conversion of GLA to DGLA (see FIG. 1; WO 00/12720). In order to compare the conversion efficiency of the wildtype and codon-optimized elongase genes, the percent substrate conversion was determined in Yarrowia lipolytica containing pY58 and pELS. Transformants were grown from single colonies in 3 mL minimal media, subcultured into minimal media containing 10 μg of GLA and subjected to lipid analysis as described in Example 2.

Results of the GLA feeding experiment indicated that Yarrowia lipolytica containing pY58 converted ~30% substrate GLA to DGLA (FIG. 16A), while those containing pELS converted ~47% GLA to DGLA (FIG. 16B). On this basis, the codon-optimized elongase gene converted approximately 57% more GLA than the wild type M. alpina elongase gene in Y. lipolytica.

SEQUENCE LISTING

<160> NUMBER OF SEQ ID NOS: 122

<210> SEQ ID NO 1
<211> LENGTH: 1374
<212> TYPE: DNA
<213> ORGANISM: Mortierella alpina AF465281

<400> SEQUENCE: 1

```
atggctgctg ctcccagtgt gaggacgttt actcgggccg aggttttgaa tgccgaggct      60
ctgaatgagg caagaaggga tgccgaggca cccttcttga tgatcatcga acaaggtg      120
tacgatgtcc gcgagttcgt ccctgatcat cccggtggaa gtgtgattct cacgcacgtt     180
ggcaaggacg gcactgacgt ctttgacact tttcaccccg aggctgcttg ggagactctt     240
gccaactttt acgttggtga tattgacgag agcgaccgcg atatcaagaa tgatgacttt     300
gcggccgagt ccgcaagct gcgtaccttg ttccagtctc ttggttacta cgattcttcc      360
aaggcatact acgccttcaa ggtctcgttc aacctctgca tctggggttt gtcgacggtc     420
attgtggcca gtggggcca gacctcgacc ctcgccaacg tgctctcggc tgcgcttttg      480
ggtctgttct ggcagcagtg cggatggttg gctcacgact ttttgcatca ccaggtcttc     540
caggaccgtt tctggggtga tcttttcggc gccttcttgg aggtgtctg ccagggcttc      600
tcgtcctcgt ggtggaagga caagcacaac actcaccacg ccgcccccaa cgtccacggc     660
gaggatcccg acattgacac ccaccctctg ttgacctgga gtgagcatgc gttggagatg     720
ttctcggatg tcccagatga ggagctgacc cgcatgtggt cgcgtttcat ggtcctgaac     780
cagacctggt tttacttccc cattctctcg tttgcccgtc tctcctggtg cctccagtcc     840
attctctttg tgctgcctaa cggtcaggcc acaagccct cgggcgcgcg tgtgcccatc       900
tcgttggtcg agcagctgtc gcttgcgatg cactggacct ggtacctcgc caccatgttc     960
ctgttcatca aggatcccgt caacatgctg gtgtacttt tggtgtcgca ggcggtgtgc     1020
ggaaacttgt tggcgatcgt gttctcgctc aaccacaacg gtatgcctgt gatctcgaag     1080
gaggaggcgg tcgatatgga tttcttcacg aagcagatca tcacgggtcg tgatgtccac     1140
ccgggtctat ttgccaactg gttcacgggt ggattgaact atcagatcga gcaccacttg     1200
ttcccttcga tgcctcgcca aacttttca agatccagc ctgctgtcga gaccctgtgc      1260
aaaaagtaca atgtccgata ccacaccacc ggtatgatcg agggaactgc agaggtcttt    1320
agccgtctga cgaggtctc caaggctacc tccaagatgg gtaaggcgca gtaa            1374
```

<210> SEQ ID NO 2
<211> LENGTH: 457
<212> TYPE: PRT
<213> ORGANISM: Mortierella alpina AF465281

<400> SEQUENCE: 2

```
Met Ala Ala Ala Pro Ser Val Arg Thr Phe Thr Arg Ala Glu Val Leu
 1               5                  10                  15

Asn Ala Glu Ala Leu Asn Glu Gly Lys Lys Asp Ala Glu Ala Pro Phe
             20                  25                  30

Leu Met Ile Ile Asp Asn Lys Val Tyr Asp Val Arg Glu Phe Val Pro
         35                  40                  45

Asp His Pro Gly Gly Ser Val Ile Leu Thr His Val Gly Lys Asp Gly
     50                  55                  60

Thr Asp Val Phe Asp Thr Phe His Pro Glu Ala Ala Trp Glu Thr Leu
```

```
                65                  70                  75                  80
Ala Asn Phe Tyr Val Gly Asp Ile Asp Glu Ser Asp Arg Asp Ile Lys
                    85                  90                  95

Asn Asp Asp Phe Ala Ala Glu Val Arg Lys Leu Arg Thr Leu Phe Gln
                100                 105                 110

Ser Leu Gly Tyr Tyr Asp Ser Ser Lys Ala Tyr Tyr Ala Phe Lys Val
                115                 120                 125

Ser Phe Asn Leu Cys Ile Trp Gly Leu Ser Thr Val Ile Val Ala Lys
            130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
                180                 185                 190

Leu Gly Gly Val Cys Gln Gly Phe Ser Ser Trp Trp Lys Asp Lys
                195                 200                 205

His Asn Thr His His Ala Ala Pro Asn Val His Gly Glu Asp Pro Asp
            210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
                275                 280                 285

Gln Ala His Lys Pro Ser Gly Ala Arg Val Pro Ile Ser Leu Val Glu
            290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
            355                 360                 365

Phe Thr Lys Gln Ile Ile Thr Gly Arg Asp Val His Pro Gly Leu Phe
            370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
                420                 425                 430

Ile Glu Gly Thr Ala Glu Val Phe Ser Arg Leu Asn Glu Val Ser Lys
            435                 440                 445

Ala Thr Ser Lys Met Gly Lys Ala Gln
    450                 455

<210> SEQ ID NO 3
<211> LENGTH: 1077
<212> TYPE: DNA
<213> ORGANISM: Saprolegnia diclina (ATCC #56851)
```

<400> SEQUENCE: 3

```
atgactgagg ataagacgaa ggtcgagttc ccgacgctca cggagctcaa gcactcgatc    60
ccgaacgcgt gctttgagtc gaacctcggc ctctcgctct actacacggc ccgcgcgatc   120
ttcaacgcgt cggcctcggc ggcgctgctc tacgcggcgc gctcgacgcc gttcattgcc   180
gataacgttc tgctccacgc gctcgtttgc gccacctaca tctacgtgca gggcgtcatc   240
ttctggggct tcttcacggt cggccacgac tgcggccact cggccttctc gcgctaccac   300
agcgtcaact ttatcatcgg ctgcatcatg cactctgcga ttttgacgcc gttcgagagc   360
tggcgcgtga cgcaccgcca ccaccacaag aacacgggca acattgataa ggacgagatc   420
ttttacccgc accggtcggt caaggacctc caggacgtgc gccaatgggt ctacacgctc   480
ggcggtgcgt ggtttgtcta cttgaaggtc gggtatgccc cgcgcacgat gagccacttt   540
gacccgtggg acccgctcct ccttcgccgc gcgtcggccg tcatcgtgtc gctcggcgtc   600
tgggccgcct tcttcgccgc gtacgcgtac ctcacatact cgctcggctt tgccgtcatg   660
ggcctctact actatgcgcc gctctttgtc tttgcttcgt tcctcgtcat tacgaccttc   720
ttgcaccaca acgacgaagc gacgccgtgg tacgcgact cggagtggac gtacgtcaag   780
ggcaacctct cgagcgtcga ccgctcgtac ggcgcgttcg tggacaacct gagccaccac   840
attggcacgc accaggtcca ccacttgttc ccgatcattc cgcactacaa gctcaacgaa   900
gccaccaagc actttgcggc cgcgtacccg cacctcgtgc gcaggaacga cgagcccatc   960
atcacggcct tcttcaagac cgcgcacctc tttgtcaact acggcgctgt gcccgagacg  1020
gcgcagatct tcacgctcaa agagtcggcc gcggccgcca aggccaagtc ggactaa     1077
```

<210> SEQ ID NO 4
<211> LENGTH: 358
<212> TYPE: PRT
<213> ORGANISM: Saprolegnia diclina (ATCC #56851)

<400> SEQUENCE: 4

```
Met Ala Glu Asp Lys Thr Lys Val Glu Phe Pro Thr Leu Thr Glu Leu
1               5                   10                  15

Lys His Ser Ile Pro Asn Ala Cys Phe Glu Ser Asn Leu Gly Leu Ser
            20                  25                  30

Leu Tyr Tyr Thr Ala Arg Ala Ile Phe Asn Ala Ser Ala Ser Ala Ala
        35                  40                  45

Leu Leu Tyr Ala Ala Arg Ser Thr Pro Phe Ile Ala Asp Asn Val Leu
    50                  55                  60

Leu His Ala Leu Val Cys Ala Thr Tyr Ile Tyr Val Gln Gly Val Ile
65                  70                  75                  80

Phe Trp Gly Phe Phe Thr Val Gly His Asp Cys Gly His Ser Ala Phe
                85                  90                  95

Ser Arg Tyr His Ser Val Asn Phe Ile Ile Gly Cys Ile Met His Ser
            100                 105                 110

Ala Ile Leu Thr Pro Phe Glu Ser Trp Arg Val Thr His Arg His
        115                 120                 125

His Lys Asn Thr Gly Asn Ile Asp Lys Asp Glu Ile Phe Tyr Pro His
    130                 135                 140

Arg Ser Val Lys Asp Leu Gln Asp Val Arg Gln Trp Val Tyr Thr Leu
145                 150                 155                 160

Gly Gly Ala Trp Phe Val Tyr Leu Lys Val Gly Tyr Ala Pro Arg Thr
                165                 170                 175
```

Met Ser His Phe Asp Pro Trp Asp Pro Leu Leu Leu Arg Arg Ala Ser
            180                 185                 190

Ala Val Ile Val Ser Leu Gly Val Trp Ala Ala Phe Phe Ala Ala Tyr
        195                 200                 205

Ala Tyr Leu Thr Tyr Ser Leu Gly Phe Ala Val Met Gly Leu Tyr Tyr
        210                 215                 220

Tyr Ala Pro Leu Phe Val Phe Ala Ser Phe Leu Val Ile Thr Thr Phe
225                 230                 235                 240

Leu His His Asn Asp Glu Ala Thr Pro Trp Tyr Gly Asp Ser Glu Trp
            245                 250                 255

Thr Tyr Val Lys Gly Asn Leu Ser Ser Val Asp Arg Ser Tyr Gly Ala
        260                 265                 270

Phe Val Asp Asn Leu Ser His His Ile Gly Thr His Gln Val His His
        275                 280                 285

Leu Phe Pro Ile Ile Pro His Tyr Lys Leu Asn Glu Ala Thr Lys His
        290                 295                 300

Phe Ala Ala Ala Tyr Pro His Leu Val Arg Arg Asn Asp Glu Pro Ile
305                 310                 315                 320

Ile Thr Ala Phe Phe Lys Thr Ala His Leu Phe Val Asn Tyr Gly Ala
                325                 330                 335

Val Pro Glu Thr Ala Gln Ile Phe Thr Leu Lys Glu Ser Ala Ala Ala
            340                 345                 350

Ala Lys Ala Lys Ser Asp
        355

<210> SEQ ID NO 5
<211> LENGTH: 957
<212> TYPE: DNA
<213> ORGANISM: Mortierella alpina AX464731

<400> SEQUENCE: 5
atggagtcga ttgcgccatt cctcccatca aagatgccgc aagatctgtt tatggaccttt    60
gccaccgcta tcggtgtccg ggccgcgccc tatgtcgatc ctctcgaggc cgcgctggtg   120
gcccaggccg agaagtacat ccccacgatt gtccatcaca cgcgtgggtt cctggtcgcg   180
gtggagtcgc ctttggcccg tgagctgccg ttgatgaacc cgttccacgt gctgttgatc   240
gtgctcgctt atttggtcac ggtctttgtg ggcatgcaga tcatgaagaa ctttgagcgg   300
ttcgaggtca agacgttttc gctcctgcac aactttttgtc tggtctcgat cagcgcctac   360
atgtgcggtg ggatcctgta cgaggcttat caggccaact atggactgtt tgagaacgct   420
gctgatcata cctttcaaggg tcttcctatg gccaagatga tctggctctt ctacttctcc   480
aagatcatgg agtttgtcga caccatgatc atggtcctca gaagaacaa ccgccagatc   540
tccttcttgc acgtttacca ccacagctcc atcttcacca tctggtggtt ggtcaccttt   600
gttgcaccca acggtgaagc ctacttctct gctgcgttga actcgttcat ccatgtgatc   660
atgtacggct actacttctt gtcggccttg ggcttcaagc aggtgtcgtt catcaagttc   720
tacatcacgc gctcgcagat gacacagttc tgcatgatgt cggtccagtc ttcctgggac   780
atgtacgcca tgaaggtcct tggccgcccc ggatacccct tcttcatcac ggctctgctt   840
tggttctaca tgtggaccat gctcggtctc ttctacaact tttacagaaa gaacgccaag   900
ttggccaagc aggccaaggc cgacgctgcc aaggagaagg caaggaagtt gcagtaa      957

<210> SEQ ID NO 6

<211> LENGTH: 318
<212> TYPE: PRT
<213> ORGANISM: Mortierella alpina AX464731

<400> SEQUENCE: 6

```
Met Glu Ser Ile Ala Pro Phe Leu Pro Ser Lys Met Pro Gln Asp Leu
1               5                   10                  15

Phe Met Asp Leu Ala Thr Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Glu Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
    290                 295                 300

Ala Lys Ala Asp Ala Ala Lys Glu Lys Ala Arg Lys Leu Gln
305                 310                 315
```

<210> SEQ ID NO 7
<211> LENGTH: 19
<212> TYPE: DNA
<213> ORGANISM: Artificial Sequence
<220> FEATURE:
<223> OTHER INFORMATION: Primer TEF5'

<400> SEQUENCE: 7
agagaccggg ttggcggcg                                                19

```
<210> SEQ ID NO 8
<211> LENGTH: 30
<212> TYPE: DNA
<213> ORGANISM: Artificial Sequence
<220> FEATURE:
<223> OTHER INFORMATION: Primer TEF3'

<400> SEQUENCE: 8
ttggatcctt tgaatgattc ttatactcag                              30

<210> SEQ ID NO 9
<211> LENGTH: 29
<212> TYPE: DNA
<213> ORGANISM: Artificial Sequence
<220> FEATURE:
<223> OTHER INFORMATION: Primer XPR5'

<400> SEQUENCE: 9
tttccgcggc ccgagattcc ggcctcttc                               29

<210> SEQ ID NO 10
<211> LENGTH: 31
<212> TYPE: DNA
<213> ORGANISM: Artificial Sequence
<220> FEATURE:
<223> OTHER INFORMATION: Primer XPR3'

<400> SEQUENCE: 10
tttccgcgga cacaatatct ggtcaaattt c                            31

<210> SEQ ID NO 11
<211> LENGTH: 30
<212> TYPE: DNA
<213> ORGANISM: Artificial Sequence
<220> FEATURE:
<223> OTHER INFORMATION: Primer YL1

<400> SEQUENCE: 11
cagtgccaaa agccaaggca ctgagctcgt                              30

<210> SEQ ID NO 12
<211> LENGTH: 31
<212> TYPE: DNA
<213> ORGANISM: Artificial Sequence
<220> FEATURE:
<223> OTHER INFORMATION: Primer YL2

<400> SEQUENCE: 12
gacgagctca gtgccttggc ttttggcact g                            31

<210> SEQ ID NO 13
<211> LENGTH: 36
<212> TYPE: DNA
<213> ORGANISM: Artificial Sequence
<220> FEATURE:
<223> OTHER INFORMATION: Primer YL3

<400> SEQUENCE: 13
gtataagaat cattcaccat ggatccacta gttcta                       36

<210> SEQ ID NO 14
<211> LENGTH: 36
<212> TYPE: DNA
<213> ORGANISM: Artificial Sequence
<220> FEATURE:
<223> OTHER INFORMATION: Primer YL4
```

<400> SEQUENCE: 14
tagaactagt ggatccatgg tgaatgattc ttatac                                   36

<210> SEQ ID NO 15
<211> LENGTH: 36
<212> TYPE: DNA
<213> ORGANISM: Artificial Sequence
<220> FEATURE:
<223> OTHER INFORMATION: Primer YL23

<400> SEQUENCE: 15
atggatccac tagttaatta actagagcgg ccgcca                                   36

<210> SEQ ID NO 16
<211> LENGTH: 36
<212> TYPE: DNA
<213> ORGANISM: Artificial Sequence
<220> FEATURE:
<223> OTHER INFORMATION: Primer YL24

<400> SEQUENCE: 16
tggcggccgc tctagttaat taactagtgg atccat                                   36

<210> SEQ ID NO 17
<211> LENGTH: 39
<212> TYPE: DNA
<213> ORGANISM: Artificial Sequence
<220> FEATURE:
<223> OTHER INFORMATION: Primer YL5

<400> SEQUENCE: 17
cccccctcga ggtcgatggt gtcgataagc ttgatatcg                                39

<210> SEQ ID NO 18
<211> LENGTH: 39
<212> TYPE: DNA
<213> ORGANISM: Artificial Sequence
<220> FEATURE:
<223> OTHER INFORMATION: Primer YL6

<400> SEQUENCE: 18
cgatatcaag cttatcgaca ccatcgacct cgaggggggg                               39

<210> SEQ ID NO 19
<211> LENGTH: 35
<212> TYPE: DNA
<213> ORGANISM: Artificial Sequence
<220> FEATURE:
<223> OTHER INFORMATION: Primer YL9

<400> SEQUENCE: 19
tggtaaataa atgatgtcga ctcaggcgac gacgg                                    35

<210> SEQ ID NO 20
<211> LENGTH: 35
<212> TYPE: DNA
<213> ORGANISM: Artificial Sequence
<220> FEATURE:
<223> OTHER INFORMATION: Primer YL10

<400> SEQUENCE: 20
ccgtcgtcgc ctgagtcgac atcatttatt tacca                                    35

<210> SEQ ID NO 21
<211> LENGTH: 37

```
<212> TYPE: DNA
<213> ORGANISM: Artificial Sequence
<220> FEATURE:
<223> OTHER INFORMATION: Primer YL7

<400> SEQUENCE: 21
caaccgattt cgacagttaa ttaataattt gaatcga                              37

<210> SEQ ID NO 22
<211> LENGTH: 37
<212> TYPE: DNA
<213> ORGANISM: Artificial Sequence
<220> FEATURE:
<223> OTHER INFORMATION: Primer YL8

<400> SEQUENCE: 22
tcgattcaaa ttattaatta actgtcgaaa tcggttg                              37

<210> SEQ ID NO 23
<211> LENGTH: 33
<212> TYPE: DNA
<213> ORGANISM: Artificial Sequence
<220> FEATURE:
<223> OTHER INFORMATION: Primer YL61

<400> SEQUENCE: 23
acaattccac acaacgtacg agccggaagc ata                                  33

<210> SEQ ID NO 24
<211> LENGTH: 33
<212> TYPE: DNA
<213> ORGANISM: Artificial Sequence
<220> FEATURE:
<223> OTHER INFORMATION: Primer YL62

<400> SEQUENCE: 24
tatgcttccg gctcgtacgt tgtgtggaat tgt                                  33

<210> SEQ ID NO 25
<211> LENGTH: 1374
<212> TYPE: DNA
<213> ORGANISM: Mortierella alpina

<400> SEQUENCE: 25
atggctgccg ctccctctgt gcgaaccttt acccgagccg aggttctgaa cgctgaggct     60
ctgaacgagg gcaagaagga cgctgaggct cccttcctga tgatcatcga caacaaggtg    120
tacgacgtcc gagagttcgt ccctgaccat cctggaggct ccgtgattct cacccacgtt    180
ggcaaggacg gcaccgacgt ctttgacacc tttcatcccg aggctgcttg ggagactctc    240
gccaacttct acgttggaga cattgacgag tccgaccgag acatcaagaa cgatgacttt    300
gccgctgagg tccgaaagct gcgaaccctg ttccagtctc tcggctacta cgactcctct    360
aaggcctact acgccttcaa ggtctccttc aacctctgca tctggggact gtccaccgtc    420
attgtggcca gtggggtca gacctccacc ctcgccaacg tgctctctgc tgccctgctc    480
ggcctgttct ggcagcagtg cggatggctg gctcacgact ttctgcacca ccaggtcttc    540
caggaccgat ctgggggtga tctcttcgga gccttctggg aggtgtctg ccagggcttc    600
tcctcttcct ggtggaagga caagcacaac actcaccatg ccgctcccaa cgtgcatggc    660
gaggatcctg acattgacac ccaccctctc ctgacctggt ccgagcacgc tctggagatg    720
ttctccgacg tccccgatga ggagctgacc cgaatgtggt ctcgattcat ggtcctgaac    780
```

```
cagacctggt tctacttccc cattctctcc ttcgctcgac tgtcttggtg cctccagtcc    840
attctctttg tgctgcccaa cggtcaggct cacaagccct ccggagctcg agtgcccatc    900
tccctggtcg agcagctgtc cctcgccatg cactggacct ggtacctcgc taccatgttc    960
ctgttcatca aggatcctgt caacatgctc gtgtacttcc tggtgtctca ggctgtgtgc   1020
ggaaacctgc tcgccatcgt gttctccctc aaccacaacg gtatgcctgt gatctccaag   1080
gaggaggctg tcgacatgga tttctttacc aagcagatca tcactggtcg agatgtccat   1140
cctggactgt tcgccaactg gttcaccggt ggcctgaact accagatcga gcatacctg    1200 ttcccttcca tgcctcgaca caacttctcc aagatccagc tgccgtcga ccctgtgc     1260 aagaagtaca acgtccgata ccacaccact ggtatgatcg agggaactgc cgaggtcttc   1320
tcccgactga acgaggtctc caaggccacc tccaagatgg gcaaggctca gtaa         1374
```

<210> SEQ ID NO 26
<211> LENGTH: 89
<212> TYPE: DNA
<213> ORGANISM: Artificial Sequence
<220> FEATURE:
<223> OTHER INFORMATION: Primer D6-1A

<400> SEQUENCE: 26

```
ccatggctgc cgctccctct gtgcgaacct ttacccgagc cgaggttctg aacgctgagg    60
ctctgaacga gggcaagaag gacgctgag                                      89
```

<210> SEQ ID NO 27
<211> LENGTH: 91
<212> TYPE: DNA
<213> ORGANISM: Artificial Sequence
<220> FEATURE:
<223> OTHER INFORMATION: Primer D6-1B

<400> SEQUENCE: 27

```
gagcctcagc gtccttcttg ccctcgttca gagcctcagc gttcagaacc tcggctcggg    60
taaaggttcg cacagaggga gcggcagcca t                                   91
```

<210> SEQ ID NO 28
<211> LENGTH: 92
<212> TYPE: DNA
<213> ORGANISM: Artificial Sequence
<220> FEATURE:
<223> OTHER INFORMATION: Primer D6-2A

<400> SEQUENCE: 28

```
gctcccttcc tgatgatcat cgacaacaag gtgtacgacg tccgagagtt cgtccctgac    60
catcctggag gctccgtgat tctcacccac gt                                  92
```

<210> SEQ ID NO 29
<211> LENGTH: 92
<212> TYPE: DNA
<213> ORGANISM: Artificial Sequence
<220> FEATURE:
<223> OTHER INFORMATION: Primer D6-2B

<400> SEQUENCE: 29

```
gccaacgtgg gtgagaatca cggagcctcc aggatggtca gggacgaact ctcggacgtc    60
gtacaccttg ttgtcgatga tcatcaggaa gg                                  92
```

<210> SEQ ID NO 30
<211> LENGTH: 90

```
<212> TYPE: DNA
<213> ORGANISM: Artificial Sequence
<220> FEATURE:
<223> OTHER INFORMATION: Primer D6-3A

<400> SEQUENCE: 30
tggcaaggac ggcaccgacg tctttgacac ctttcatccc gaggctgctt gggagactct      60
cgccaacttc tacgttggag acattgacga                                       90

<210> SEQ ID NO 31
<211> LENGTH: 90
<212> TYPE: DNA
<213> ORGANISM: Artificial Sequence
<220> FEATURE:
<223> OTHER INFORMATION: Primer D6-3B

<400> SEQUENCE: 31
ggactcgtca atgtctccaa cgtagaagtt ggcgagagtc tcccaagcag cctcgggatg      60
aaaggtgtca aagacgtcgg tgccgtcctt                                       90

<210> SEQ ID NO 32
<211> LENGTH: 100
<212> TYPE: DNA
<213> ORGANISM: Artificial Sequence
<220> FEATURE:
<223> OTHER INFORMATION: Primer D6-4A

<400> SEQUENCE: 32
gtccgaccga gacatcaaga acgatgactt tgccgctgag gtccgaaagc tgcgaaccct      60
gttccagtct ctcggctact acgactcctc taaggcctac                           100

<210> SEQ ID NO 33
<211> LENGTH: 100
<212> TYPE: DNA
<213> ORGANISM: Artificial Sequence
<220> FEATURE:
<223> OTHER INFORMATION: Primer D6-4B

<400> SEQUENCE: 33
cgtagtaggc cttagaggag tcgtagtagc cgagagactg aacagggtt cgcagctttc       60 ggacctcagc ggcaaagtca tcgttcttga tgtctcggtc                           100

<210> SEQ ID NO 34
<211> LENGTH: 101
<212> TYPE: DNA
<213> ORGANISM: Artificial Sequence
<220> FEATURE:
<223> OTHER INFORMATION: Primer D6-5A

<400> SEQUENCE: 34
ctaaggccta ctacgccttc aaggtctcct tcaacctctg catctgggga ctgtccaccg      60
tcattgtggc caagtggggt cagacctcca ccctcgccaa c                         101

<210> SEQ ID NO 35
<211> LENGTH: 101
<212> TYPE: DNA
<213> ORGANISM: Artificial Sequence
<220> FEATURE:
<223> OTHER INFORMATION: Primer D6-5B

<400> SEQUENCE: 35
gcacgttggc gagggtggag gtctgacccc acttggccac aatgacggtg gacagtcccc      60
```
agatgcagag gttgaaggag accttgaagg cgtagtaggc c        101

<210> SEQ ID NO 36
<211> LENGTH: 104
<212> TYPE: DNA
<213> ORGANISM: Artificial Sequence
<220> FEATURE:
<223> OTHER INFORMATION: Primer D6-6A

<400> SEQUENCE: 36
gtgctctctg ctgccctgct cggcctgttc tggcagcagt gcggatggct ggctcacgac        60
tttctgcacc accaggtctt ccaggaccga ttctggggtg atct        104

<210> SEQ ID NO 37
<211> LENGTH: 104
<212> TYPE: DNA
<213> ORGANISM: Artificial Sequence
<220> FEATURE:
<223> OTHER INFORMATION: Primer D6-6B

<400> SEQUENCE: 37
gaagagatca cccagaatc ggtcctggaa gacctggtgg tgcagaaagt cgtgagccag        60
ccatccgcac tgctgccaga acaggccgag cagggcagca gaga        104

<210> SEQ ID NO 38
<211> LENGTH: 105
<212> TYPE: DNA
<213> ORGANISM: Artificial Sequence
<220> FEATURE:
<223> OTHER INFORMATION: Primer D6-7A

<400> SEQUENCE: 38
cttcggagcc ttcctgggag gtgtctgcca gggcttctcc tcttcctggt ggaaggacaa        60
gcacaacact caccatgccg ctcccaacgt gcatggcgag gatcc        105

<210> SEQ ID NO 39
<211> LENGTH: 103
<212> TYPE: DNA
<213> ORGANISM: Artificial Sequence
<220> FEATURE:
<223> OTHER INFORMATION: Primer D6-7B

<400> SEQUENCE: 39
caggatcctc gccatgcacg ttgggagcgg catggtgagt gttgtgcttg tccttccacc        60
aggaagagga gaagccctgg cagacacctc ccaggaaggc tcc        103

<210> SEQ ID NO 40
<211> LENGTH: 106
<212> TYPE: DNA
<213> ORGANISM: Artificial Sequence
<220> FEATURE:
<223> OTHER INFORMATION: Primer D6-8A

<400> SEQUENCE: 40
gaggatcctg acattgacac ccaccctctc ctgacctggt ccgagcacgc tctggagatg        60
ttctccgacg tccccgatga ggagctgacc cgaatgtggt ctcgat        106

<210> SEQ ID NO 41
<211> LENGTH: 108
<212> TYPE: DNA
<213> ORGANISM: Artificial Sequence
<220> FEATURE:
<223> OTHER INFORMATION: Primer D6-8B

<400> SEQUENCE: 41
atgaatcgag accacattcg ggtcagctcc tcatcgggga cgtcggagaa catctccaga    60
gcgtgctcgg accaggtcag gagagggtgg gtgtcaatgt caggatcc    108

<210> SEQ ID NO 42
<211> LENGTH: 106
<212> TYPE: DNA
<213> ORGANISM: Artificial Sequence
<220> FEATURE:
<223> OTHER INFORMATION: Primer D6-9A

<400> SEQUENCE: 42
tcatggtcct gaaccagacc tggttctact tccccattct ctccttcgct cgactgtctt    60
ggtgcctcca gtccattctc tttgtgctgc ccaacggtca ggctca    106

<210> SEQ ID NO 43
<211> LENGTH: 106
<212> TYPE: DNA
<213> ORGANISM: Artificial Sequence
<220> FEATURE:
<223> OTHER INFORMATION: Primer D6-9B

<400> SEQUENCE: 43
cttgtgagcc tgaccgttgg gcagcacaaa gagaatggac tggaggcacc aagacagtcg    60
agcgaaggag agaatgggga agtagaacca ggtctggttc aggacc    106

<210> SEQ ID NO 44
<211> LENGTH: 105
<212> TYPE: DNA
<213> ORGANISM: Artificial Sequence
<220> FEATURE:
<223> OTHER INFORMATION: Primer D6-10A

<400> SEQUENCE: 44
caagccctcc ggagctcgag tgcccatctc cctggtcgag cagctgtccc tcgccatgca    60
ctggacctgg tacctcgcta ccatgttcct gttcatcaag gatcc    105

<210> SEQ ID NO 45
<211> LENGTH: 103
<212> TYPE: DNA
<213> ORGANISM: Artificial Sequence
<220> FEATURE:
<223> OTHER INFORMATION: Primer D6-10B

<400> SEQUENCE: 45
caggatcctt gatgaacagg aacatggtag cgaggtacca ggtccagtgc atggcgaggg    60
acagctgctc gaccagggag atgggcactc gagctccgga ggg    103

<210> SEQ ID NO 46
<211> LENGTH: 104
<212> TYPE: DNA
<213> ORGANISM: Artificial Sequence
<220> FEATURE:
<223> OTHER INFORMATION: Primer D6-11A

<400> SEQUENCE: 46
aggatcctgt caacatgctc gtgtacttcc tggtgtctca ggctgtgtgc ggaaacctgc    60
tcgccatcgt gttctccctc aaccacaacg gtatgcctgt gatc    104

<210> SEQ ID NO 47

<210> SEQ ID NO 47
<211> LENGTH: 106
<212> TYPE: DNA
<213> ORGANISM: Artificial Sequence
<220> FEATURE:
<223> OTHER INFORMATION: Primer D6-11B

<400> SEQUENCE: 47
tggagatcac aggcataccg ttgtggttga gggagaacac gatggcgagc aggtttccgc    60
acacagcctg agacaccagg aagtacacga gcatgttgac aggatc                 106

<210> SEQ ID NO 48
<211> LENGTH: 105
<212> TYPE: DNA
<213> ORGANISM: Artificial Sequence
<220> FEATURE:
<223> OTHER INFORMATION: Primer D6-12A

<400> SEQUENCE: 48
tccaaggagg aggctgtcga catggatttc tttaccaagc agatcatcac tggtcgagat    60
gtccatcctg gactgttcgc caactggttc accggtggcc tgaac                  105

<210> SEQ ID NO 49
<211> LENGTH: 105
<212> TYPE: DNA
<213> ORGANISM: Artificial Sequence
<220> FEATURE:
<223> OTHER INFORMATION: Primer D6-12B

<400> SEQUENCE: 49
ggtagttcag gccaccggtg aaccagttgg cgaacagtcc aggatggaca tctcgaccag    60
tgatgatctg cttggtaaag aaatccatgt cgacagcctc ctcct                  105

<210> SEQ ID NO 50
<211> LENGTH: 102
<212> TYPE: DNA
<213> ORGANISM: Artificial Sequence
<220> FEATURE:
<223> OTHER INFORMATION: Primer D6-13A

<400> SEQUENCE: 50
taccagatcg agcatcacct gttcccttcc atgcctcgac acaacttctc caagatccag    60
cctgccgtcg agaccctgtg caagaagtac aacgtccgat ac                     102

<210> SEQ ID NO 51
<211> LENGTH: 102
<212> TYPE: DNA
<213> ORGANISM: Artificial Sequence
<220> FEATURE:
<223> OTHER INFORMATION: Primer D6-13B

<400> SEQUENCE: 51
tgtggtatcg gacgttgtac ttcttgcaca gggtctcgac ggcaggctgg atcttggaga    60
agttgtgtcg aggcatggaa gggaacaggt gatgctcgat ct                     102

<210> SEQ ID NO 52
<211> LENGTH: 97
<212> TYPE: DNA
<213> ORGANISM: Artificial Sequence
<220> FEATURE:
<223> OTHER INFORMATION: Primer D6-14A

<400> SEQUENCE: 52
cacaccactg gtatgatcga gggaactgcc gaggtcttct cccgactgaa cgaggtctcc    60
aaggccacct ccaagatggg caaggctcag taagcgg         97

<210> SEQ ID NO 53
<211> LENGTH: 97
<212> TYPE: DNA
<213> ORGANISM: Artificial Sequence
<220> FEATURE:
<223> OTHER INFORMATION: Primer D6-14B

<400> SEQUENCE: 53
gcggccgctt actgagcctt gcccatcttg gaggtggcct tgagacctc gttcagtcgg         60 gagaagacct cggcagttcc ctcgatcata ccagtgg         97

<210> SEQ ID NO 54
<211> LENGTH: 21
<212> TYPE: DNA
<213> ORGANISM: Artificial Sequence
<220> FEATURE:
<223> OTHER INFORMATION: Primer D6-1

<400> SEQUENCE: 54
ccatggctgc cgctccctct g         21

<210> SEQ ID NO 55
<211> LENGTH: 20
<212> TYPE: DNA
<213> ORGANISM: Artificial Sequence
<220> FEATURE:
<223> OTHER INFORMATION: Primer D6-4R

<400> SEQUENCE: 55
cgtagtaggc cttagaggag         20

<210> SEQ ID NO 56
<211> LENGTH: 20
<212> TYPE: DNA
<213> ORGANISM: Artificial Sequence
<220> FEATURE:
<223> OTHER INFORMATION: Primer D6-5

<400> SEQUENCE: 56
ctaaggccta ctacgccttc         20

<210> SEQ ID NO 57
<211> LENGTH: 20
<212> TYPE: DNA
<213> ORGANISM: Artificial Sequence
<220> FEATURE:
<223> OTHER INFORMATION: Primer D6-7R

<400> SEQUENCE: 57
caggatcctc gccatgcacg         20

<210> SEQ ID NO 58
<211> LENGTH: 21
<212> TYPE: DNA
<213> ORGANISM: Artificial Sequence
<220> FEATURE:
<223> OTHER INFORMATION: Primer D6-8

<400> SEQUENCE: 58
gaggatcctg acattgacac c         21

<210> SEQ ID NO 59

```
<211> LENGTH: 20
<212> TYPE: DNA
<213> ORGANISM: Artificial Sequence
<220> FEATURE:
<223> OTHER INFORMATION: Primer D6-10R

<400> SEQUENCE: 59
caggatcctt gatgaacagg                                               20

<210> SEQ ID NO 60
<211> LENGTH: 21
<212> TYPE: DNA
<213> ORGANISM: Artificial Sequence
<220> FEATURE:
<223> OTHER INFORMATION: Primer D6-11

<400> SEQUENCE: 60
aggatcctgt caacatgctc g                                             21

<210> SEQ ID NO 61
<211> LENGTH: 27
<212> TYPE: DNA
<213> ORGANISM: Artificial Sequence
<220> FEATURE:
<223> OTHER INFORMATION: Primer D6-14R

<400> SEQUENCE: 61
gcggccgctt actgagcctt gcccatc                                       27

<210> SEQ ID NO 62
<211> LENGTH: 1077
<212> TYPE: DNA
<213> ORGANISM: Saprolegnia diclina

<400> SEQUENCE: 62
atggctgagg ataagaccaa ggtcgagttc cctaccctga ctgagctgaa gcactctatc    60
cctaacgctt gctttgagtc caacctcgga ctctcgctct actacactgc ccgagcgatc   120
ttcaacgcat ctgcctctgc tgctctgctc tacgctgccc gatctactcc cttcattgcc   180
gataacgttc tgctccacgc tctggtttgc gccacctaca tctacgtgca gggtgtcatc   240
ttctggggtt tctttaccgt cggtcacgac tgtggtcact ctgccttctc ccgataccac   300
tccgtcaact tcatcattgg ctgcatcatg cactctgcca ttctgactcc cttcgagtcc   360
tggcgagtga cccaccgaca ccatcacaag aacactggca acattgataa ggacgagatc   420
ttctaccctc atcggtccgt caaggacctc caggacgtgc gacaatgggt ctacaccctc   480
ggaggtgctt ggtttgtcta cctgaaggtc ggatatgctc ctcgaaccat gtcccacttt   540
gaccgctggg accctctcct gcttcgacga gcctccgctg tcatcgtgtc cctcggagtc   600
tgggctgcct tcttcgctgc ctacgcctac ctcacatact cgctcggctt gccgtcatg    660
ggcctctact actatgctcc tctctttgtc tttgcttcgt tcctcgtcat tactaccttc   720
ttgcatcaca cgacgaagc tactccctgg tacggtgact cggagtggac ctacgtcaag   780
ggcaacctga gctccgtcga ccgatcgtac ggagctttcg tggacaacct gtctcaccac   840
attggcaccc accaggtcca tcacttgttc cctatcattc cccactacaa gctcaacgaa   900
gccaccaagc actttgctgc cgcttaccct cacctcgtga gactgtaacga cgagcccatc   960
attactgcct tcttcaagac cgctcacctc tttgtcaact acggagctgt gcccgagact  1020
gctcagattt tcaccctcaa agagtctgcc gctgcagcca aggccaagag cgactaa     1077
```

<210> SEQ ID NO 63
<211> LENGTH: 105
<212> TYPE: DNA
<213> ORGANISM: Artificial Sequence
<220> FEATURE:
<223> OTHER INFORMATION: Primer D17-1A

<400> SEQUENCE: 63
catggctgag gataagacca aggtcgagtt ccctaccctg actgagctga agcactctat    60
ccctaacgct tgctttgagt ccaacctcgg actctcgctc tacta                   105

<210> SEQ ID NO 64
<211> LENGTH: 106
<212> TYPE: DNA
<213> ORGANISM: Artificial Sequence
<220> FEATURE:
<223> OTHER INFORMATION: Primer D17-1B

<400> SEQUENCE: 64
cagtgtagta gagcgagagt ccgaggttgg actcaaagca agcgttaggg atagagtgct    60
tcagctcagt cagggtaggg aactcgacct tggtcttatc ctcagc                  106

<210> SEQ ID NO 65
<211> LENGTH: 106
<212> TYPE: DNA
<213> ORGANISM: Artificial Sequence
<220> FEATURE:
<223> OTHER INFORMATION: Primer D17-2A

<400> SEQUENCE: 65
cactgcccga gcgatcttca acgcatctgc ctctgctgct ctgctctacg ctgcccgatc    60
tactcccttc attgccgata acgttctgct ccacgctctg gtttgc                  106

<210> SEQ ID NO 66
<211> LENGTH: 106
<212> TYPE: DNA
<213> ORGANISM: Artificial Sequence
<220> FEATURE:
<223> OTHER INFORMATION: Primer D17-2B

<400> SEQUENCE: 66
gtggcgcaaa ccagagcgtg gagcagaacg ttatcggcaa tgaagggagt agatcgggca    60
gcgtagagca gagcagcaga ggcagatgcg ttgaagatcg ctcggg                  106

<210> SEQ ID NO 67
<211> LENGTH: 105
<212> TYPE: DNA
<213> ORGANISM: Artificial Sequence
<220> FEATURE:
<223> OTHER INFORMATION: Primer D17-3A

<400> SEQUENCE: 67
gccacctaca tctacgtgca gggtgtcatc ttctggggtt tctttaccgt cggtcacgac    60
tgtggtcact ctgccttctc ccgataccac tccgtcaact tcatc                   105

<210> SEQ ID NO 68
<211> LENGTH: 105
<212> TYPE: DNA
<213> ORGANISM: Artificial Sequence
<220> FEATURE:
<223> OTHER INFORMATION: Primer D17-3B

<400> SEQUENCE: 68
ccaatgatga agttgacgga gtggtatcgg gagaaggcag agtgaccaca gtcgtgaccg    60
acggtaaaga aaccccagaa gatgacaccc tgcacgtaga tgtag                      105

<210> SEQ ID NO 69
<211> LENGTH: 105
<212> TYPE: DNA
<213> ORGANISM: Artificial Sequence
<220> FEATURE:
<223> OTHER INFORMATION: Primer D17-4A

<400> SEQUENCE: 69
attggctgca tcatgcactc tgccattctg actcccttcg agtcctggcg agtgacccac    60
cgacaccatc acaagaacac tggcaacatt gataaggacg agatc                     105

<210> SEQ ID NO 70
<211> LENGTH: 105
<212> TYPE: DNA
<213> ORGANISM: Artificial Sequence
<220> FEATURE:
<223> OTHER INFORMATION: Primer D17-4B

<400> SEQUENCE: 70
tagaagatct cgtccttatc aatgttgcca gtgttcttgt gatggtgtcg gtgggtcact    60
cgccaggact cgaagggagt cagaatggca gagtgcatga tgcag                     105

<210> SEQ ID NO 71
<211> LENGTH: 105
<212> TYPE: DNA
<213> ORGANISM: Artificial Sequence
<220> FEATURE:
<223> OTHER INFORMATION: Primer D17-5A

<400> SEQUENCE: 71
acgagatctt ctaccctcat cggtccgtca aggacctcca ggacgtgcga caatgggtct    60
acaccctcgg aggtgcttgg tttgtctacc tgaaggtcgg atatg                     105

<210> SEQ ID NO 72
<211> LENGTH: 107
<212> TYPE: DNA
<213> ORGANISM: Artificial Sequence
<220> FEATURE:
<223> OTHER INFORMATION: Primer D17-5B

<400> SEQUENCE: 72
aggagcatat ccgaccttca ggtagacaaa ccaagcacct ccgagggtgt agacccattg    60
tcgcacgtcc tggaggtcct tgacggaccg atgagggtag aagatct                   107

<210> SEQ ID NO 73
<211> LENGTH: 105
<212> TYPE: DNA
<213> ORGANISM: Artificial Sequence
<220> FEATURE:
<223> OTHER INFORMATION: Primer D17-6A

<400> SEQUENCE: 73
ctcctcgaac catgtcccac tttgacccct gggaccctct cctgcttcga cgagcctccg    60
ctgtcatcgt gtccctcgga gtctgggctg ccttcttcgc tgcct                     105

<210> SEQ ID NO 74
<211> LENGTH: 106
<212> TYPE: DNA
<213> ORGANISM: Artificial Sequence

```
<220> FEATURE:
<223> OTHER INFORMATION: Primer D17-6B

<400> SEQUENCE: 74
aggcgtaggc agcgaagaag gcagcccaga ctccgaggga cacgatgaca gcggaggctc    60
gtcgaagcag gagagggtcc caggggtcaa agtgggacat ggttcg                  106

<210> SEQ ID NO 75
<211> LENGTH: 104
<212> TYPE: DNA
<213> ORGANISM: Artificial Sequence
<220> FEATURE:
<223> OTHER INFORMATION: Primer D17-7A

<400> SEQUENCE: 75
acgcctacct cacatactcg ctcggctttg ccgtcatggg cctctactac tatgctcctc    60
tctttgtctt tgcttcgttc ctcgtcatta ctaccttctt gcat                    104

<210> SEQ ID NO 76
<211> LENGTH: 103
<212> TYPE: DNA
<213> ORGANISM: Artificial Sequence
<220> FEATURE:
<223> OTHER INFORMATION: Primer D17-7B

<400> SEQUENCE: 76
ttgtgatgca agaaggtagt aatgacgagg aacgaagcaa agacaaagag aggagcatag    60
tagtagaggc ccatgacggc aaagccgagc gagtatgtga ggt                     103

<210> SEQ ID NO 77
<211> LENGTH: 106
<212> TYPE: DNA
<213> ORGANISM: Artificial Sequence
<220> FEATURE:
<223> OTHER INFORMATION: Primer D17-8A

<400> SEQUENCE: 77
cacaacgacg aagctactcc ctggtacggt gactcggagt ggacctacgt caagggcaac    60
ctgagctccg tcgaccgatc gtacggagct tcgtggaca acctgt                   106

<210> SEQ ID NO 78
<211> LENGTH: 106
<212> TYPE: DNA
<213> ORGANISM: Artificial Sequence
<220> FEATURE:
<223> OTHER INFORMATION: Primer D17-8B

<400> SEQUENCE: 78
gtgagacagg ttgtccacga aagctccgta cgatcggtcg acggagctca ggttgccctt    60
gacgtaggtc cactccgagt caccgtacca gggagtagct cgtcg                   106

<210> SEQ ID NO 79
<211> LENGTH: 102
<212> TYPE: DNA
<213> ORGANISM: Artificial Sequence
<220> FEATURE:
<223> OTHER INFORMATION: Primer D17-9A

<400> SEQUENCE: 79
ctcaccacat tggcacccac caggtccatc acttgttccc tatcattccc cactacaagc    60
tcaacgaagc caccaagcac tttgctgccg cttaccctca cc                      102
```

<210> SEQ ID NO 80
<211> LENGTH: 102
<212> TYPE: DNA
<213> ORGANISM: Artificial Sequence
<220> FEATURE:
<223> OTHER INFORMATION: Primer D17-9B

<400> SEQUENCE: 80
cacgaggtga gggtaagcgg cagcaaagtg cttggtggct tcgttgagct tgtagtgggg    60
aatgataggg aacaagtgat ggacctggtg ggtgccaatg tg                      102

<210> SEQ ID NO 81
<211> LENGTH: 76
<212> TYPE: DNA
<213> ORGANISM: Artificial Sequence
<220> FEATURE:
<223> OTHER INFORMATION: Primer D17-10A

<400> SEQUENCE: 81
tcgtgagacg taacgacgag cccatcatta ctgccttctt caagaccgct cacctctttg    60
tcaactacgg agctgt                                                    76

<210> SEQ ID NO 82
<211> LENGTH: 76
<212> TYPE: DNA
<213> ORGANISM: Artificial Sequence
<220> FEATURE:
<223> OTHER INFORMATION: Primer D17-10B

<400> SEQUENCE: 82
cgggcacagc tccgtagttg acaaagaggt gagcggtctt gaagaaggca gtaatgatgg    60
gctcgtcgtt acgtct                                                    76

<210> SEQ ID NO 83
<211> LENGTH: 67
<212> TYPE: DNA
<213> ORGANISM: Artificial Sequence
<220> FEATURE:
<223> OTHER INFORMATION: Primer D17-11A

<400> SEQUENCE: 83
gcccgagact gctcagattt tcaccctcaa agagtctgcc gctgcagcca aggccaagag    60
cgactaa                                                              67

<210> SEQ ID NO 84
<211> LENGTH: 62
<212> TYPE: DNA
<213> ORGANISM: Artificial Sequence
<220> FEATURE:
<223> OTHER INFORMATION: Primer D17-11B

<400> SEQUENCE: 84
ttagtcgctc ttggccttgg ctgcagcggc agactctttg agggtgaaaa tctgagcagt    60
ct                                                                   62

<210> SEQ ID NO 85
<211> LENGTH: 32
<212> TYPE: DNA
<213> ORGANISM: Artificial Sequence
<220> FEATURE:
<223> OTHER INFORMATION: Primer D17-1

<400> SEQUENCE: 85

<210> SEQ ID NO 86
<211> LENGTH: 34
<212> TYPE: DNA
<213> ORGANISM: Artificial Sequence
<220> FEATURE:
<223> OTHER INFORMATION: Primer D17-4R

<400> SEQUENCE: 86
ccctagaaga tctcgtcctt atcaatgttg ccag                        34

<210> SEQ ID NO 87
<211> LENGTH: 27
<212> TYPE: DNA
<213> ORGANISM: Artificial Sequence
<220> FEATURE:
<223> OTHER INFORMATION: Primer D17-5

<400> SEQUENCE: 87
cccacgagat cttctaccct catcggt                                27

<210> SEQ ID NO 88
<211> LENGTH: 24
<212> TYPE: DNA
<213> ORGANISM: Artificial Sequence
<220> FEATURE:
<223> OTHER INFORMATION: Primer D17-8D

<400> SEQUENCE: 88
gaaagctccg tacgatcggt cgac                                   24

<210> SEQ ID NO 89
<211> LENGTH: 24
<212> TYPE: DNA
<213> ORGANISM: Artificial Sequence
<220> FEATURE:
<223> OTHER INFORMATION: Primer D17-8U

<400> SEQUENCE: 89
gtcgaccgat cgtacggagc tttc                                   24

<210> SEQ ID NO 90
<211> LENGTH: 34
<212> TYPE: DNA
<213> ORGANISM: Artificial Sequence
<220> FEATURE:
<223> OTHER INFORMATION: Primer D17-11

<400> SEQUENCE: 90
aaagcggccg cttagtcgct cttggccttg gctg                        34

<210> SEQ ID NO 91
<211> LENGTH: 957
<212> TYPE: DNA
<213> ORGANISM: Mortierella alpina

<400> SEQUENCE: 91

| | |
|---|---|
| atggagtcca ttgctccctt cctgccctcc aagatgcctc aggacctgtt catggacctc | 60 |
| gccaccgcta tcggtgtccg agctgctccc tacgtcgatc ccctggaggc tgccctggtt | 120 |
| gcccaggccg agaagtacat tcccaccatt gtccatcaca ctcgaggctt cctggttgcc | 180 |
| gtggagtctc cctggctcg agagctgcct ctgatgaacc ccttccacgt gctcctgatc | 240 | tttccatggc tgaggataag accaaggtcg ag                          32

```
gtgctcgcct acctggtcac cgtgtttgtg ggtatgcaga tcatgaagaa ctttgaacga      300
ttcgaggtca agaccttctc cctcctgcac aacttctgtc tggtctccat ctccgcctac      360
atgtgcggtg gcatcctgta cgaggcttat caggccaact atggactgtt tgagaacgct      420
gccgatcaca ccttcaaggg tctccctatg ctaagatga tctggctctt ctacttctcc       480
aagatcatgg agtttgtcga caccatgatc atggtcctca agaagaacaa ccgacagatt      540
tcctttctgc acgtgtacca ccactcttcc atcttcacca tctggtggct ggtcaccttc      600
gttgctccca acgtgaagc ctacttctct gctgccctga actccttcat ccacgtcatc       660
atgtacggct actactttct gtctgccctg ggcttcaagc aggtgtcgtt catcaagttc      720
tacatcactc gatcccagat gacccagttc tgcatgatgt ctgtccagtc ttcctgggac      780
atgtacgcca tgaaggtcct tggccgacct ggataccct tcttcatcac cgctctgctc        840
tggttctaca tgtggaccat gctcggtctc ttctacaact tttaccgaaa gaacgccaag      900
ctcgccaagc aggccaaggc tgacgctgcc aaggagaagg ccagaaagct ccagtaa        957

<210> SEQ ID NO 92
<211> LENGTH: 100
<212> TYPE: DNA
<213> ORGANISM: Artificial Sequence
<220> FEATURE:
<223> OTHER INFORMATION: Primer EL-1A

<400> SEQUENCE: 92
ccatggagtc cattgctccc ttcctgccct ccaagatgcc tcaggacctg ttcatggacc       60
tcgccaccgc tatcggtgtc cgagctgctc cctacgtcga                           100

<210> SEQ ID NO 93
<211> LENGTH: 103
<212> TYPE: DNA
<213> ORGANISM: Artificial Sequence
<220> FEATURE:
<223> OTHER INFORMATION: Primer EL-1B

<400> SEQUENCE: 93
ggggatcgac gtagggagca gctcggacac cgatagcggt ggcgaggtcc atgaacaggt       60
cctgaggcat cttggagggc aggaagggag caatggactc cat                       103

<210> SEQ ID NO 94
<211> LENGTH: 101
<212> TYPE: DNA
<213> ORGANISM: Artificial Sequence
<220> FEATURE:
<223> OTHER INFORMATION: Primer EL-2A

<400> SEQUENCE: 94
cccctggagg ctgccctggt tgcccaggcc gagaagtaca ttcccaccat tgtccatcac       60
actcgaggct tcctggttgc cgtggagtct ccctggctc g                          101

<210> SEQ ID NO 95
<211> LENGTH: 101
<212> TYPE: DNA
<213> ORGANISM: Artificial Sequence
<220> FEATURE:
<223> OTHER INFORMATION: Primer EL-2B

<400> SEQUENCE: 95
ctctcgagcc aggggagact ccacggcaac caggaagcct cgagtgtgat ggacaatggt      60
gggaatgtac ttctcggcct gggcaaccag ggcagcctcc a                         101
```

<210> SEQ ID NO 96
<211> LENGTH: 100
<212> TYPE: DNA
<213> ORGANISM: Artificial Sequence
<220> FEATURE:
<223> OTHER INFORMATION: Primer EL-3A

<400> SEQUENCE: 96
agagctgcct ctgatgaacc ccttccacgt gctcctgatc gtgctcgcct acctggtcac    60
cgtgtttgtg ggtatgcaga tcatgaagaa ctttgaacga                         100

<210> SEQ ID NO 97
<211> LENGTH: 100
<212> TYPE: DNA
<213> ORGANISM: Artificial Sequence
<220> FEATURE:
<223> OTHER INFORMATION: Primer EL-3B

<400> SEQUENCE: 97
cgaatcgttc aaagttcttc atgatctgca tacccacaaa cacggtgacc aggtaggcga    60
gcacgatcag gagcacgtgg aaggggttca tcagaggcag                         100

<210> SEQ ID NO 98
<211> LENGTH: 100
<212> TYPE: DNA
<213> ORGANISM: Artificial Sequence
<220> FEATURE:
<223> OTHER INFORMATION: Primer EL-4A

<400> SEQUENCE: 98
ttcgaggtca agaccttctc cctcctgcac aacttctgtc tggtctccat ctccgcctac    60
atgtgcggtg gcatcctgta cgaggcttat caggccaact                         100

<210> SEQ ID NO 99
<211> LENGTH: 100
<212> TYPE: DNA
<213> ORGANISM: Artificial Sequence
<220> FEATURE:
<223> OTHER INFORMATION: Primer EL-4B

<400> SEQUENCE: 99
ccatagttgg cctgataagc ctcgtacagg atgccaccgc acatgtaggc ggagatggag    60
accagacaga agttgtgcag gagggagaag gtcttgacct                         100

<210> SEQ ID NO 100
<211> LENGTH: 101
<212> TYPE: DNA
<213> ORGANISM: Artificial Sequence
<220> FEATURE:
<223> OTHER INFORMATION: Primer EL-5A

<400> SEQUENCE: 100
atggactgtt tgagaacgct gccgatcaca ccttcaaggg tctccctatg gctaagatga    60
tctggctctt ctacttctcc aagatcatgg agtttgtcga c                       101

<210> SEQ ID NO 101
<211> LENGTH: 101
<212> TYPE: DNA
<213> ORGANISM: Artificial Sequence
<220> FEATURE:
<223> OTHER INFORMATION: Primer EL-5B -continued

<400> SEQUENCE: 101
tggtgtcgac aaactccatg atcttggaga agtagaagag ccagatcatc ttagccatag    60
ggagacccct gaaggtgtga tcggcagcgt tctcaaacag t    101

<210> SEQ ID NO 102
<211> LENGTH: 89
<212> TYPE: DNA
<213> ORGANISM: Artificial Sequence
<220> FEATURE:
<223> OTHER INFORMATION: Primer EL-6A

<400> SEQUENCE: 102
accatgatca tggtcctcaa gaagaacaac cgacagattt cctttctgca cgtgtaccac    60
cactcttcca tcttcaccat ctggtggct    89

<210> SEQ ID NO 103
<211> LENGTH: 89
<212> TYPE: DNA
<213> ORGANISM: Artificial Sequence
<220> FEATURE:
<223> OTHER INFORMATION: Primer EL-6B

<400> SEQUENCE: 103
gaccagccac cagatggtga agatggaaga gtggtggtac acgtgcagaa aggaaatctg    60
tcggttgttc ttcttgagga ccatgatca    89

<210> SEQ ID NO 104
<211> LENGTH: 89
<212> TYPE: DNA
<213> ORGANISM: Artificial Sequence
<220> FEATURE:
<223> OTHER INFORMATION: Primer EL-7A

<400> SEQUENCE: 104
ggtcaccttc gttgctccca acggtgaagc ctacttctct gctgccctga actccttcat    60
ccacgtcatc atgtacggct actactttc    89

<210> SEQ ID NO 105
<211> LENGTH: 89
<212> TYPE: DNA
<213> ORGANISM: Artificial Sequence
<220> FEATURE:
<223> OTHER INFORMATION: Primer EL-7B

<400> SEQUENCE: 105
gacagaaagt agtagccgta catgatgacg tggatgaagg agttcagggc agcagagaag    60
taggcttcac cgttgggagc aacgaaggt    89

<210> SEQ ID NO 106
<211> LENGTH: 91
<212> TYPE: DNA
<213> ORGANISM: Artificial Sequence
<220> FEATURE:
<223> OTHER INFORMATION: Primer EL-8A

<400> SEQUENCE: 106
tgtctgccct gggcttcaag caggtgtcgt tcatcaagtt ctacatcact cgatcccaga    60
tgacccagtt ctgcatgatg tctgtccagt c    91

<210> SEQ ID NO 107
<211> LENGTH: 91

<212> TYPE: DNA
<213> ORGANISM: Artificial Sequence
<220> FEATURE:
<223> OTHER INFORMATION: Primer EL-8B

<400> SEQUENCE: 107
ggaagactgg acagacatca tgcagaactg ggtcatctgg gatcgagtga tgtagaactt     60
gatgaacgac acctgcttga agcccagggc a     91

<210> SEQ ID NO 108
<211> LENGTH: 90
<212> TYPE: DNA
<213> ORGANISM: Artificial Sequence
<220> FEATURE:
<223> OTHER INFORMATION: Primer EL-9A

<400> SEQUENCE: 108
ttcctgggac atgtacgcca tgaaggtcct tggccgacct ggataccct tcttcatcac     60 cgctctgctc tggttctaca tgtggaccat     90

<210> SEQ ID NO 109
<211> LENGTH: 90
<212> TYPE: DNA
<213> ORGANISM: Artificial Sequence
<220> FEATURE:
<223> OTHER INFORMATION: Primer EL-9B

<400> SEQUENCE: 109
gagcatggtc cacatgtaga accagagcag agcggtgatg aagaagggt atccaggtcg     60 gccaaggacc ttcatggcgt acatgtccca     90

<210> SEQ ID NO 110
<211> LENGTH: 97
<212> TYPE: DNA
<213> ORGANISM: Artificial Sequence
<220> FEATURE:
<223> OTHER INFORMATION: Primer EL-10A

<400> SEQUENCE: 110
gctcggtctc ttctacaact tttaccgaaa gaacgccaag ctcgccaagc aggccaaggc     60
tgacgctgcc aaggagaagg ccagaaagct ccagtaa     97

<210> SEQ ID NO 111
<211> LENGTH: 94
<212> TYPE: DNA
<213> ORGANISM: Artificial Sequence
<220> FEATURE:
<223> OTHER INFORMATION: Primer EL-10B

<400> SEQUENCE: 111
cttactggag ctttctggcc ttctccttgg cagcgtcagc cttggcctgc ttggcgagct     60
tggcgttctt tcggtaaaag ttgtagaaga gacc     94

<210> SEQ ID NO 112
<211> LENGTH: 27
<212> TYPE: DNA
<213> ORGANISM: Artificial Sequence
<220> FEATURE:
<223> OTHER INFORMATION: Primer EL-1

<400> SEQUENCE: 112
tttccatgga gtccattgct cccttcc     27

<210> SEQ ID NO 113
<211> LENGTH: 23
<212> TYPE: DNA
<213> ORGANISM: Artificial Sequence
<220> FEATURE:
<223> OTHER INFORMATION: Primer EL-5R

<400> SEQUENCE: 113
tggtgtcgac aaactccatg atc                                          23

<210> SEQ ID NO 114
<211> LENGTH: 33
<212> TYPE: DNA
<213> ORGANISM: Artificial Sequence
<220> FEATURE:
<223> OTHER INFORMATION: Primer EL-6

<400> SEQUENCE: 114
tttgtcgaca ccatgatcat ggtcctcaag aag                               33

<210> SEQ ID NO 115
<211> LENGTH: 35
<212> TYPE: DNA
<213> ORGANISM: Artificial Sequence
<220> FEATURE:
<223> OTHER INFORMATION: Primer EL-10R

<400> SEQUENCE: 115
aaagcggccg cttactggag ctttctggcc ttctc                             35

<210> SEQ ID NO 116
<211> LENGTH: 30
<212> TYPE: DNA
<213> ORGANISM: Artificial Sequence
<220> FEATURE:
<223> OTHER INFORMATION: Primer EL-M1

<400> SEQUENCE: 116
tcatggacct cgccaccgct atcggtgtcc                                   30

<210> SEQ ID NO 117
<211> LENGTH: 30
<212> TYPE: DNA
<213> ORGANISM: Artificial Sequence
<220> FEATURE:
<223> OTHER INFORMATION: Primer EL-M2

<400> SEQUENCE: 117
ggacaccgat agcggtggcg aggtccatga                                   30

<210> SEQ ID NO 118
<211> LENGTH: 33
<212> TYPE: DNA
<213> ORGANISM: Artificial Sequence
<220> FEATURE:
<223> OTHER INFORMATION: Primer YL21A

<400> SEQUENCE: 118
tttccatggc tgaggataag acgaaggtcg agt                               33

<210> SEQ ID NO 119
<211> LENGTH: 36
<212> TYPE: DNA
<213> ORGANISM: Artificial Sequence
<220> FEATURE:
<223> OTHER INFORMATION: Primer YL22

```
<400> SEQUENCE: 119
cccttaatta attagtccga cttggccttg gcggcc                              36

<210> SEQ ID NO 120
<211> LENGTH: 36
<212> TYPE: DNA
<213> ORGANISM: Artificial Sequence
<220> FEATURE:
<223> OTHER INFORMATION: Primer YL53

<400> SEQUENCE: 120
gccaagtcgg actaagctgc taactagagc ggccgc                              36

<210> SEQ ID NO 121
<211> LENGTH: 36
<212> TYPE: DNA
<213> ORGANISM: Artificial Sequence
<220> FEATURE:
<223> OTHER INFORMATION: Primer YL54

<400> SEQUENCE: 121
gcggccgctc tagttagcag cttagtccga cttggc                              36

<210> SEQ ID NO 122
<211> LENGTH: 10
<212> TYPE: DNA
<213> ORGANISM: Yarrowia lipolytica
<220> FEATURE:
<221> NAME/KEY: misc_feature
<222> LOCATION: (8)..(8)
<223> OTHER INFORMATION: n is a, c, g, or t

<400> SEQUENCE: 122 mammatgnhs                                                           10
```

What is claimed is:

1. An isolated nucleic acid molecule comprising a *Yarrowia* translation initiation site as set forth in SEQ ID NO:122, wherein:
   (a) said isolated nucleic acid molecule comprising a *Yarrowia* translation initiation site is comprised within a chimeric gene capable of being expressed in *Yarrowia*; and,
   (b) the fifth, sixth and seventh nucleotides of SEQ ID NO:122 encode a methionine that corresponds to the first amino acid of the protein encoded by the chimeric gene.

* * * * *